(12) United States Patent
Li et al.

(10) Patent No.: US 12,053,443 B2
(45) Date of Patent: Aug. 6, 2024

(54) AMINO-ARYL-BENZAMIDE COMPOUNDS AND METHODS OF USE THEREOF

(71) Applicant: HEPANOVA, INC., Gaithersburg, MD (US)

(72) Inventors: Ke Li, Shanghai (CN); Belle Xiaohong Wang, Germantown, MD (US); Yongmei Li, New York, NY (US); Qiong Li, Irvine, CA (US)

(73) Assignee: Hepanova, Inc., Irvine, CA (US)

( * ) Notice: Subject to any disclaimer, the term of this patent is extended or adjusted under 35 U.S.C. 154(b) by 228 days.

(21) Appl. No.: 17/232,527

(22) Filed: Apr. 16, 2021

(65) Prior Publication Data

US 2021/0338610 A1    Nov. 4, 2021

Related U.S. Application Data

(63) Continuation of application No. 15/971,496, filed on May 4, 2018, now Pat. No. 11,000,491.

(60) Provisional application No. 62/539,036, filed on Jul. 31, 2017, provisional application No. 62/502,385, filed on May 5, 2017.

(51) Int. Cl.
*A61K 31/18* (2006.01)
*A61K 31/17* (2006.01)
*A61P 1/16* (2006.01)

(52) U.S. Cl.
CPC .............. *A61K 31/18* (2013.01); *A61K 31/17* (2013.01); *A61P 1/16* (2018.01)

(58) Field of Classification Search
CPC combination set(s) only.
See application file for complete search history.

(56) References Cited

U.S. PATENT DOCUMENTS

| 4,044,049 A | 8/1977 | Ruyle et al. |
| 7,358,376 B2 | 4/2008 | Baxter et al. |
| 8,658,181 B2 | 2/2014 | Hsu et al. |
| 11,000,491 B2 | 5/2021 | Li et al. |
| 2009/0270418 A1 | 10/2009 | Sloss et al. |
| 2015/0290154 A1 | 10/2015 | Roberts et al. |

FOREIGN PATENT DOCUMENTS

| EP | 2598142 | 12/2015 |
| WO | WO 03/037886 | 5/2003 |
| WO | WO 2007/025575 | 3/2007 |
| WO | WO 2013/147649 | 10/2013 |
| WO | WO 2016/210289 | 12/2016 |

OTHER PUBLICATIONS

Kawamura, J Clin Invest, 2022, 132, 11 (Year: 2022).*
Moslehi et al., J of Clinical and Translational Hepatology, 2018, 6, 332-338 (Year: 2018).*
Creativebiolabs, 2023 (Year: 2023).*
Beraza et al. "Pharmacological IKK2 inhibitions blocks liver steatosis and initiation of non-alcoholic steatohepatitis," Gut, 2008, vol. 57, pp. 655-663.
Christopher et al. "The discovery of 2-amino-3,5-diarylbenzamide inhibitors of IKK-α and IKK-62 kinases," Bioorganic & Medicinal Chemistry Letters, Jul. 2007, vol. 17, No. 14, pp. 3972-3977.
International Search Report and Written Opinion for International (PCT) Patent Application No. PCT/US18/31072, dated Aug. 24, 2018 7 pages.
International Preliminary Report on Patentability for International (PCT) Patent Application No. PCT/US2018/031072, dated Nov. 14, 2019 6 pages.
Extended Search Report for European Patent Application No. 18793826.1, dated Dec. 3, 2020 6 pages.
Official Action with English Translation for Taiwan Patent Application No. 107115339, dated Jan. 7, 2019 22 pages.
Official Action for U.S. Appl. No. 15/971,496, dated Dec. 12, 2018 9 pages Restriction Requirement.
Official Action for U.S. Appl. No. 15/971,496, dated Apr. 12, 2019 17 pages.
Official Action for U.S. Appl. No. 15/971,496, dated Nov. 1, 2019 17 pages.
Notice of Allowance for U.S. Appl. No. 15/971,496, dated Jan. 28, 2021 9 pages.
Notice of Allowance with English Translation for China Patent Application No. 201810427371.6, dated Jun. 1, 2021 4 pages.
Official Action with English Translation for Taiwan Patent Application No. 107115339, dated Mar. 29, 2021 12 pages.
Official Action for European Patent Application No. 18793826.1, dated Sep. 20, 2021 5 pages.
Official Action with English Translation for Taiwan Patent Application No. 107115339, dated Aug. 9, 2021 6 pages.
Christopher et al. "Discovery of 6-Aryl-7-alkoxyisoquinoline Inhibitors of IkB Kinase-β (Ikk-β)," Journal of Medicinal Chemistry, 2009, vol. 52, No. 9, pp. 3098-3102.
Jue et al. "IkB kinase-beta inhibitor attenuates hepatic fibrosis in mice," World Journal of Gastroenterology, Dec. 2011, vol. 17, No. 37, pp. 5203-5213.
Li et al. "Hepatitis C virus infection activates an innate pathway involving IKK-α in lipogenesis and viral assembly," Nature Medicine, Jun. 2013, vol. 19, No. 6, pp. 722-729.
Extended Search Report for European Patent Application No. 23163130.0, dated Sep. 22, 2023 10 pages.

* cited by examiner

*Primary Examiner* — Umamaheswari Ramachandran
(74) *Attorney, Agent, or Firm* — Sheridan Ross P.C.

(57) ABSTRACT

A method for the treatment and/or reduction of nonalcoholic fatty liver disease (NAFLD) and nonalcoholic steatohepatitis (NASH) is disclosed. The method uses active amino-aryl-benzamide compounds and methods for the preparation thereof.

18 Claims, 73 Drawing Sheets

Formula I

Formula II

Formula III

Formula IV

Fig. 5A
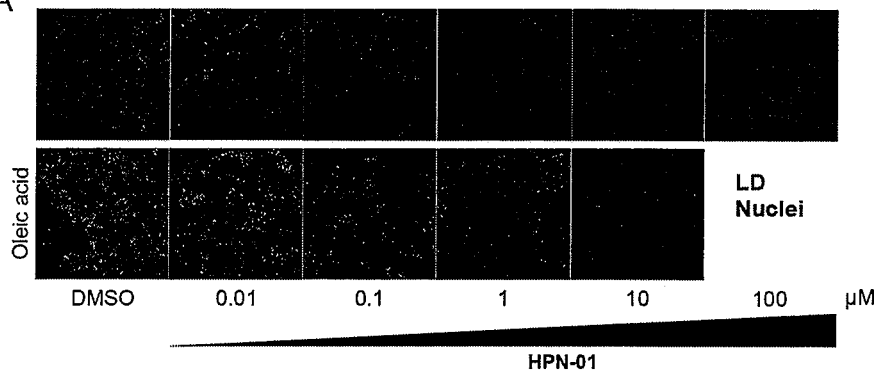
Fig. 5B
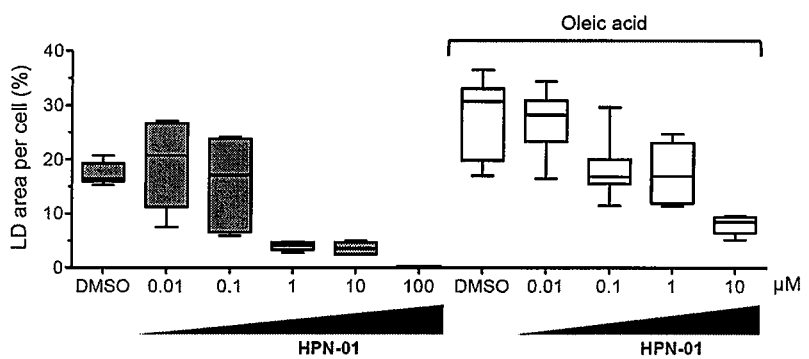
Fig. 5C
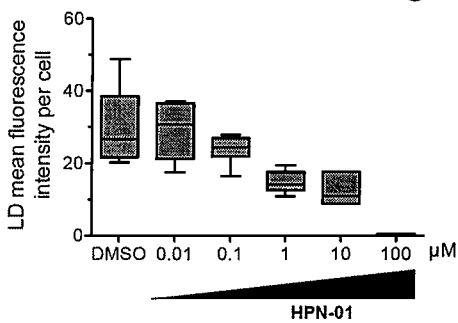
Fig. 5D
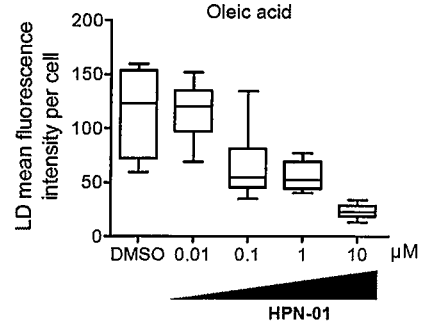
Figure 5

Elemental Composition Report

Single Mass Analysis
Tolerance = 5.0 PPM    /    DBE: min = -1.5, max = 50.0
Element prediction: Off
Number of isotope peaks used for i-FIT = 3

Monoisotopic Mass, Even Electron Ions
156 formula(e) evaluated with 4 results within limits (up to 50 closest results for each mass)
Elements Used:
C: 1-30    H: 1-30    N: 0-3    O: 0-3    S: 0-1    Cl: 0-1

| | | | | | | |
|---|---|---|---|---|---|---|
| Minimum: | | | | | -1.5 | |
| Maximum: | | 5.0 | | 5.0 | 50.0 | |
| Mass | Calc. Mass | mDa | PPM | DBE | i-FIT | |
| Formula | | | | | | |
| 400.0528 | 400.0529 | -0.1 | -0.2 | 22.5 | | n/a |
| C27 H11 N O Cl | | | | | | |
| | 400.0523 | 0.5 | 1.2 | 13.5 | | n/a |
| C19 H15 N3 O3 S Cl | | | | | | |
| | 400.0511 | 1.7 | 4.2 | 27.5 | | n/a |
| C28 H6 N3 O | | | | | | |
| | 400.0545 | -1.7 | -4.2 | 22.5 | | n/a |
| C25 H10 N3 O S | | | | | | |

SIPI                                                                Q-Tof micro
HPN-01                                                              YA019
Q16-0256HR 3 (0.056) AM (Cen,4, 80.00, Ar,5000.0,423.03,1.00); Sm (Mn, 2x3.00); Sb (1,5.00 ); Cm (3:20)

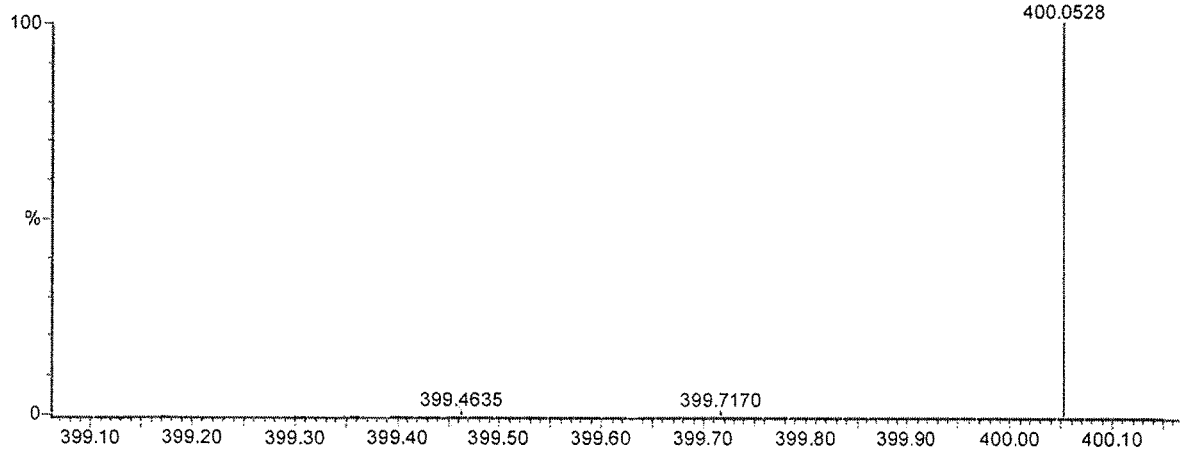

Figure 26

Formula IV

| Compound No. | Structures | | | | Molecular Formula | MW |
|---|---|---|---|---|---|---|
| | R1 | R2 | R3 | R4 | | |
| HPN-01101 | (styryl) | (4-sulfamoylphenyl) | H | H | C21H19N3O3S | 393.46 |
| HPN-01102 | (3-chlorostyryl) | (4-sulfamoylphenyl) | H | H | C21H18ClN3O3S | 427.9 |

Fig. 36 Cont'd

| Compound No. | Structures | | | | Molecular Formula | MW |
|---|---|---|---|---|---|---|
| | R1 | R2 | R3 | R4 | | |
| HPN-01103 | 3-Br-phenyl vinyl | 4-(SO2NH2)phenyl | H | H | C21H18BrN3O3S | 472.36 |
| HPN-01104 | 3-F-phenyl vinyl | 4-(SO2NH2)phenyl | H | H | C21H18FN3O3S | 411.45 |
| HPN-01105 | 4-OAc-phenyl vinyl | 4-(SO2NH2)phenyl | H | H | C21H16ClN3O3S | 451.5 |
| HPN-01106 | 4-NHAc-phenyl vinyl | 4-(SO2NH2)phenyl | H | H | C21H16ClN3O3S | 450.51 |
| HPN-01107 | 4-Cl-phenyl vinyl | 4-(SO2NH2)phenyl | H | H | C21H18ClN3O3S | 427.9 |
| HPN-01108 | 2-Cl-phenyl vinyl | 4-(SO2NH2)phenyl | H | H | C21H18ClN3O3S | 427.9 |

Fig. 36 Cont'd

| Compound No. | Structures | | | | Molecular Formula | MW |
|---|---|---|---|---|---|---|
| | R1 | R2 | R3 | R4 | | |
| HPN-01109 | 4-Br-styryl | 4-sulfamoylphenyl | H | H | C21H18BrN3O3S | 472.35 |
| HPN-01110 | 3-acetoxy-styryl | 4-sulfamoylphenyl | H | H | C23H21N3O5S | 451.5 |
| HPN-01111 | 3-(butyryloxy)styryl | 4-sulfamoylphenyl | H | H | C25H25N3O5S | 481.56 |
| HPN-01112 | 3-butyramido-styryl | 4-sulfamoylphenyl | H | H | C25H26N4O4S | 478.57 |
| HPN-01113 | (E)-2-carboxyvinyl | 4-sulfamoylphenyl | H | H | C16H15N3O5S | 361.37 |
| HPN-01114 | (E)-2-(methoxycarbonyl)vinyl | 4-sulfamoylphenyl | H | H | C17H17N3O5S | 375.4 |

Fig. 36 Cont'd

| Compound No. | Structures | | | | Molecular Formula | MW |
|---|---|---|---|---|---|---|
| | R1 | R2 | R3 | R4 | | |
| HPN-01115 | (ethyl acrylate) | 4-sulfamoylphenyl | H | H | C18H19N3O5S | 389.43 |
| HPN-01116 | (isopropyl acrylate) | 4-sulfamoylphenyl | H | H | C19H21N3O5S | 403.45 |
| HPN-01117 | (butyl acrylate) | 4-sulfamoylphenyl | H | H | C20H23N3O5S | 417.48 |
| HPN-01118 | (heptyl acrylate) | 4-sulfamoylphenyl | H | H | C23H29N3O5S | 459.56 |
| HPN-01119 | (decyl acrylate) | 4-sulfamoylphenyl | H | H | C26H35N3O5S | 501.64 |
| HPN-01120 | (benzyl acrylate) | 4-sulfamoylphenyl | H | H | C23H21N3O5S | 451.5 |

Fig. 36 Cont'd

| Compound No. | Structures | | | | Molecular Formula | MW |
|---|---|---|---|---|---|---|
| | R1 | R2 | R3 | R4 | | |
| HPN-01121 | (acrylate with HOOC-phenyl) | phenyl-SO2-NH2 | H | H | C23H20N4O6S | 480.5 |
| HPN-01122 | (acrylate with HO-phenyl) | phenyl-SO2-NH2 | H | H | C22H20N4O5S | 452.49 |
| HPN-01123 | (acrylate with phenethyl) | phenyl-SO2-NH2 | H | H | C24H23N3O5S | 465.52 |
| HPN-01124 | (acrylate with furfuryl) | phenyl-SO2-NH2 | H | H | C21H19N3O6S | 441.46 |
| HPN-01125 | (acrylamide with phenyl) | phenyl-SO2-NH2 | H | H | C22H20N4O4S | 436.49 |
| HPN-01126 | (acrylamide with tolyl) | phenyl-SO2-NH2 | H | H | C23H22N4O4S | 450.51 |

Fig. 36 Cont'd

| Compound No. | Structures | | | | Molecular Formula | MW |
|---|---|---|---|---|---|---|
| | R1 | R2 | R3 | R4 | | |
| HPN-01127 | (cinnamamide with 3-methylphenyl) | 4-sulfamoylphenyl | H | H | C23H22N4O4S | 450.51 |
| HPN-01128 | (cinnamamide with 4-methoxyphenyl) | 4-sulfamoylphenyl | H | H | C23H22N4O5S | 466.51 |
| HPN-01129 | (cinnamamide with 4-ethoxyphenyl) | 4-sulfamoylphenyl | H | H | C24H24N4O5S | 480.54 |
| HPN-01130 | (cinnamamide with 4-chlorophenyl) | 4-sulfamoylphenyl | H | H | C22H19ClN4O4S | 470.93 |
| HPN-01131 | (cinnamamide with benzyl) | 4-sulfamoylphenyl | H | H | C23H22N4O4S | 450.51 |
| HPN-01132 | (cinnamamide with 4-fluorophenethyl) | 4-sulfamoylphenyl | H | H | C24H23FN4O4S | 482.53 |

Fig. 36 Cont'd

| Compound No. | Structures | | | | Molecular Formula | MW |
|---|---|---|---|---|---|---|
| | R1 | R2 | R3 | R4 | | |
| HPN-01133 | (E)-N-cyclohexyl acrylamide group | 4-sulfamoylphenyl | H | H | C22H26N4O4S | 442.53 |
| HPN-01201 | propargyl alcohol (HOCH2-C≡C-) | 4-sulfamoylphenyl | H | H | C16H15N3O4S | 345.37 |
| HPN-01202 | phenylethynyl | 4-sulfamoylphenyl | H | H | C21H16FN3O3S | 409.44 |
| HPN-01203 | (4-fluorophenyl)ethynyl | 4-sulfamoylphenyl | H | H | C21H17N3O3S | 391.45 |
| HPN-01204 | (4-methoxyphenyl)ethynyl | 4-sulfamoylphenyl | H | H | C22H19N3O4S | 421.47 |
| HPN-01205 | (4-chlorophenyl)ethynyl | 4-sulfamoylphenyl | H | H | C21H16ClN3O3S | 425.89 |

Fig. 36 Cont'd

| Compound No. | Structures | | | | Molecular Formula | MW |
|---|---|---|---|---|---|---|
| | R1 | R2 | R3 | R4 | | |
| HPN-01206 | 3-Cl-phenyl-C≡C- | 4-(H2N-SO2)-phenyl | H | H | C21H16ClN3O3S | 470.34 |
| HPN-01207 | 4-Br-phenyl-C≡C- | 4-(H2N-SO2)-phenyl | H | H | C21H16BrN3O3S | 470.34 |
| HPN-01208 | 3-Br-phenyl-C≡C- | 4-(H2N-SO2)-phenyl | H | H | C21H16BrN3O3S | 470.34 |
| HPN-01209 | (CH3)3Si-C≡C- | 4-(H2N-SO2)-phenyl | H | H | C18H21N3O3SSi | 387.53 |
| HPN-01210 | 2-Cl-benzoyloxy-CH2-C≡C- | 4-(H2N-SO2)-phenyl | H | H | C23H18BrN3O5S | 483.92 |
| HPN-01211 | 2-Br-benzoyloxy-CH2-C≡C- | 4-(H2N-SO2)-phenyl | H | H | C23H18BrN3O5S | 528.38 |

Fig. 36 Cont'd

| Compound No. | Structures | | | | | Molecular Formula | MW |
|---|---|---|---|---|---|---|---|
| | R1 | R2 | R3 | R4 | | | |
| HPN-01212 | 2-methylbenzoate propargyl | 4-sulfamoylphenyl | H | H | | C24H21N3O5S | 463.51 |
| HPN-01213 | 2-fluorobenzoate propargyl | 4-sulfamoylphenyl | H | H | | C23H18FN3O5S | 467.41 |
| HPN-01214 | 4-methylbenzoate propargyl | 4-sulfamoylphenyl | H | H | | C24H21N3O5S | 463.51 |
| HPN-01215 | 3-methylbenzoate propargyl | 4-sulfamoylphenyl | H | H | | C24H21N3O5S | 463.51 |
| HPN-01216 | 3-methoxybenzoate propargyl | 4-sulfamoylphenyl | H | H | | C24H21N3O6S | 479.51 |
| HPN-01217 | 2-methoxybenzoate propargyl | 4-sulfamoylphenyl | H | H | | C23H18N3O6S | 479.51 |

Fig. 36 Cont'd

| Compound No | Structures | | | | Molecular Formula | MW |
|---|---|---|---|---|---|---|
| | R1 | R2 | R3 | R4 | | |
| HPN-01218 | 4-phenoxybenzoate propargyl ester | 4-aminosulfonylphenyl | H | H | C24H21N3O6S | 479.51 |
| HPN-01219 | 3-hydroxybenzoate propargyl ester | 4-aminosulfonylphenyl | H | H | C23H19N3O6S | 465.48 |
| HPN-01220 | 4-hydroxybenzoate propargyl ester | 4-aminosulfonylphenyl | H | H | C23H19N3O6S | 465.48 |
| HPN-01221 | picolinate propargyl ester | 4-aminosulfonylphenyl | H | H | C22H18N4O5S | 450.47 |
| HPN-01222 | pyrrole-2-carboxylate propargyl ester | 4-aminosulfonylphenyl | H | H | C21H18N4O5S | 438.46 |
| HPN-01223 | acetate propargyl ester | 4-aminosulfonylphenyl | H | H | C18H17N3O5S | 387.41 |

Fig. 36 Cont'd

| Compound No. | Structures | | | | Molecular Formula | MW |
|---|---|---|---|---|---|---|
| | R1 | R2 | R3 | R4 | | |
| HPN-01224 | (propargyl ester) | phenyl-SO2NH2 | H | H | C20H21N3O5S | 415.46 |
| HPN-01301 | (phenyl methyl ester) | phenyl-SO2NH2 | H | H | C21H19N3O5S | 425.46 |
| HPN-01302 | (phenyl ethyl ester) | phenyl-SO2NH2 | H | H | C22H21N3O5S | 439.48 |
| HPN-01303 | (phenyl isopropyl ester) | phenyl-SO2NH2 | H | H | C23H23N3O5S | 453.51 |
| HPN-01304 | (phenyl acetate) | phenyl-SO2NH2 | H | H | C21H19N3O5S | 425.46 |
| HPN-01305 | (phenyl propanoate) | phenyl-SO2NH2 | H | H | C22H21N3O5S | 455.48 |

Fig. 36 Cont'd

| Compound No. | Structures | | | | Molecular Formula | MW |
|---|---|---|---|---|---|---|
| | R1 | R2 | R3 | R4 | | |
| HPN-01306 | phenyl butyrate ester | 4-sulfamoylphenyl | H | H | C23H23N3O5S | 453.51 |
| HPN-01307 | 6-chloropyridin-3-yl | 4-sulfamoylphenyl | H | H | C18H15ClN4O3S | 402.85 |
| HPN-01308 | 5-chloropyridin-2-yl | 4-sulfamoylphenyl | H | H | C18H15ClN4O3S | 402.85 |
| HPN-01309 | 4-chloro-1H-pyrrol-2-yl | 4-sulfamoylphenyl | H | H | C17H15ClN4O3S | 390.84 |
| HPN-01310 | 5-chloro-1H-pyrrol-3-yl | 4-sulfamoylphenyl | H | H | C17H15ClN4O3S | 390.84 |
| HPN-01311 | 5-bromo-1H-pyrrol-3-yl | 4-sulfamoylphenyl | H | H | C17H15BrN4O3S | 435.29 |

Fig. 36 Cont'd

| Compound No. | Structures | | | | Molecular Formula | MW |
|---|---|---|---|---|---|---|
| | R1 | R2 | R3 | R4 | | |
| HPN-01312 | 4-Cl-phenyl-NH- | 4-sulfamoylphenyl | H | H | C19H17ClN4O3S | 416.88 |
| HPN-01313 | 4-Cl-phenyl-O- | 4-sulfamoylphenyl | H | H | C19H16ClN3O4S | 417.87 |
| HPN-01314 | 4-Cl-phenyl-S- | 4-sulfamoylphenyl | H | H | C19H17ClN4O3S | 433.93 |
| HPN-01315 | 3-Cl-phenyl-NH- | 4-sulfamoylphenyl | H | H | C19H17ClN4O3S | 416.88 |
| HPN-01316 | 3-Cl-phenyl-O- | 4-sulfamoylphenyl | H | H | C19H16ClN3O4S | 417.87 |
| HPN-01317 | 3-HOOC-phenyl-NH- | 4-sulfamoylphenyl | H | H | C20H18N4O6S2? | 426.45 |

Fig. 36 Cont'd

| Compound No. | Structures | | | | Molecular Formula | MW |
|---|---|---|---|---|---|---|
| | R1 | R2 | R3 | R4 | | |
| HPN-01318 | 3-HOOC-phenoxy | 4-(H2N-SO2)-phenyl | H | H | C20H17N3O6S | 427.43 |
| HPN-01319 | 3-MeOOC-phenyl-NH | 4-(H2N-SO2)-phenyl | H | H | C21H20N4O5S | 440.47 |
| HPN-01320 | 3-MeOOC-phenoxy | 4-(H2N-SO2)-phenyl | H | H | C21H19N3O6S | 441.46 |
| HPN-01321 | 3-Br-cyclopentyl | 4-(H2N-SO2)-phenyl | H | H | C18H20BrN3O3S | 438.34 |
| HPN-01322 | 4-Br-cyclohexyl | 4-(H2N-SO2)-phenyl | H | H | C19H22BrN3O3S | 452.37 |
| HPN-01401 | 4-Cl-phenyl | 4-(H2N-SO2)-phenoxy | H | H | C19H16ClN3O4S | 417.87 |

Fig. 36 Cont'd

| Compound No. | Structures | | | | Molecular Formula | MW |
|---|---|---|---|---|---|---|
| | R1 | R2 | R3 | R4 | | |
| HPN-01402 | 4-Cl-phenyl | 4-sulfamoylphenyl-NH- | H | H | C19H17ClN4O3S | 416.88 |
| HPN-01403 | 4-Cl-phenyl | 4-sulfamoylphenyl-S- | H | H | C19H16ClN3O3S2 | 433.93 |
| HPN-01404 | 4-Br-phenyl | 4-sulfamoylphenyl-NH- | H | H | C19H17BrN4O3S | 461.33 |
| HPN-01405 | 4-Cl-phenyl | 4-(phosphonooxy)phenyl | H | H | C19H16ClN2O5P | 418.77 |
| HPN-01406 | 4-Cl-phenyl | 4-ureidophenyl | H | H | C20H17ClN4O2 | 380.83 |
| HPN-01407 | 4-Cl-phenyl | 4-acetamidophenyl | H | H | C21H18ClN3O2 | 379.84 |

Fig. 36 Cont'd

| Compound No. | Structures | | | | Molecular Formula | MW |
|---|---|---|---|---|---|---|
| | R1 | R2 | R3 | R4 | | |
| HPN-01408 | 4-Cl-phenyl | 4-(propanethioamido)phenyl | H | H | C22H20ClN3O2 | 393.87 |
| HPN-01409 | 4-Cl-phenyl | 4-(butanethioamido)phenyl | H | H | C23H22ClN3O2 | 407.89 |
| HPN-01410 | 4-Cl-phenyl | 4-(1H-1,2,4-triazol-3-yl)phenyl | H | H | C20H15ClN6O2 | 406.83 |
| HPN-01411 | 4-Cl-phenyl | 4-(N-propylsulfamoyl)phenyl | H | H | C22H22ClN3O4S | 459.95 |
| HPN-01412 | 4-Cl-phenyl | 4-sulfamoylphenoxy | H | H | C19H16ClN3O5S2? | 417.87 |
| HPN-01413 | 4-Cl-phenyl | 4-sulfamoylphenylamino | H | H | C19H17ClN4O3S | 416.88 |

Fig. 36 Cont'd

| Compound No. | Structures | | | | Molecular Formula | MW |
|---|---|---|---|---|---|---|
| | R1 | R2 | R3 | R4 | | |
| HPN-01414 | 4-Cl-phenyl | 4-(H2N-SO2)-phenyl-S- | H | H | C19H15ClN3O3S2 | 433.93 |
| HPN-01415 | 4-Br-phenyl | 4-(H2N-SO2)-phenyl-O- | H | H | C19H16BrN3O4S | 462.32 |
| HPN-01416 | 4-Br-phenyl | 4-(HO)(HO)P(O)-O-phenyl | H | H | C19H16BrN2O5P | 463.22 |
| HPN-01417 | 4-Cl-phenyl | 4-(H2N-C(NH)-NH)-phenyl | H | H | C20H18ClN5O | 379.84 |
| HPN-01418 | 4-Cl-phenyl | 4-(H2N-C(S)-NH)-phenyl | H | H | C20H17ClN4OS | 396.89 |
| HPN-01419 | 4-Cl-phenyl | 4-(HO-CH2-C(S)-NH)-phenyl | H | H | C21H18ClN3O3 | 395.84 |

Fig. 36 Cont'd
| Compound No. | Structures | | | | Molecular Formula | MW |
|---|---|---|---|---|---|---|
| | R1 | R2 | R3 | R4 | | |
| HPN-01420 | 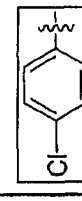 4-Cl-phenyl | 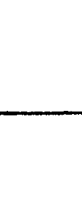 phenyl-imidazolone | H | H | C22H17ClN4O2 | 404.85 |
| HPN-01421 |  4-Cl-phenyl | 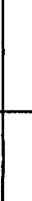 phenyl-pyrazole | H | H | C21H16ClN5O | 389.84 |
| HPN-01422 | 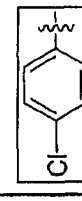 4-Cl-phenyl |  sulfonamide-ethanol | H | H | C21H20ClN3O5S | 461.92 |
| HPN-01423 | 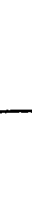 4-Cl-phenyl |  | H | H | C21H20ClN3O4S | 445.92 |
| HPN-01424 | 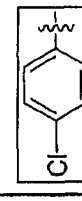 4-Cl-phenyl |  | H | H | C20H18ClN3O4S | 431.89 |
| HPN-01425 | 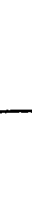 4-Cl-phenyl |  | H | H | C21H21ClN4O3S | 444.93 |

Fig. 36 Cont'd

| Compound No. | Structures | | | | Molecular Formula | MW |
|---|---|---|---|---|---|---|
| | R1 | R2 | R3 | R4 | | |
| HPN-01426 | 4-Cl-phenyl | 4-(H2NSO2)-benzyl-NH- | H | H | C20H19ClN4O3S | 430.91 |
| HPN-01427 | 4-Cl-phenyl | 4-(H2N)-piperazine-sulfonyl | H | H | C17H20ClN5O3S | 409.89 |
| HPN-01428 | 4-Cl-phenyl | 6-(H2NSO2)-pyridin-3-yl | H | H | C18H15ClN4O3S | 402.85 |
| HPN-01429 | 4-Cl-phenyl | 4-(pyridin-3-yl-NHC(O)NH)-phenyl | H | H | C25H20ClN5O2 | 457.92 |
| HPN-01430 | 4-Cl-phenyl | 4-(iPr-NHC(O)NH)-phenyl | H | H | C23H23ClN4O2 | 422.91 |
| HPN-01501 | 4-Cl-phenyl | 4-(H2NSO2)-phenyl | acetyl | H | C21H18ClN3O4S | 443.9 |

Fig. 36 Cont'd

| Compound No. | Structures | | | | Molecular Formula | MW |
|---|---|---|---|---|---|---|
| | R1 | R2 | R3 | R4 | | |
| HPN-01502 | 4-Cl-phenyl | 4-sulfonamide phenyl | -C(O)CH2OH | H | C21H18ClN3O5S | 459.9 |
| HPN-01503 | 4-Cl-phenyl | 4-sulfonamide phenyl | -C(O)-cyclopropyl | H | C23H20ClN3O4S | 469.94 |
| HPN-01504 | 4-Cl-phenyl | 4-sulfonamide phenyl | -C(O)CH2NH2 | H | C21H19ClN4O4S | 458.92 |
| HPN-01505 | 4-Cl-phenyl | urea-phenyl | -C(O)CH3 | H | C21H16ClN4O3? | 407.83 |
| HPN-01506 | 4-Cl-phenyl | urea-phenyl | -C(O)CH2OH | H | C22H19ClN4O4 | 438.86 |
| HPN-01513 | 4-Br-phenyl | 4-sulfonamide phenyl | -C(O)CH2CH2OH | H | C22H20BrN3O5S | 518.38 |

Fig. 36 Cont'd

| Compound No. | Structures | | | | Molecular Formula | MW |
|---|---|---|---|---|---|---|
| | R1 | R2 | R3 | R4 | | |
| HPN-01514 | 4-Br-phenyl | 4-sulfonamide-phenyl | -C(O)CH2CH2CH2NH2 | H | C22H21BrN4O4S | 517.4 |
| HPN-01515 | 4-Cl-phenyl | 4-sulfonamide-phenyl | -C(O)CH2CH2CH2CH3 | H | C23H22ClN3O4S | 487.96 |
| HPN-01516 | 4-Cl-phenyl | 4-sulfonamide-phenyl | -C(O)CH2CH2CH2OH | H | C22H20ClN3O5S | 473.93 |
| HPN-01517 | 4-Cl-phenyl | 4-sulfonamide-phenyl | -C(O)CH2CH2NH2 | H | C21H19ClN4O4S2 | 472.94 |
| HPN-01518 | 4-Cl-phenyl | 4-(NH2C(O)NH)-phenyl | -C(O)CH2CH2CH2NH2 | H | C22H20ClN5O3 | 453.88 |
| HPN-01519 | 4-Cl-phenyl | 4-(NH2C(O)NH)-phenyl | -C(O)CH2CH2CH2CH3 | H | C24H23ClN4O3 | 450.92 |

Fig. 36 Cont'd

| Compound No. | Structures | | | | Molecular Formula | MW |
|---|---|---|---|---|---|---|
| | R1 | R2 | R3 | R4 | | |
| HPN-01520 | 4-Cl-phenyl | 4-(NH2C(O)NH)-phenyl | -C(O)CH2CH2OH | H | C22H19ClN4O4 2? | 452.89 |
| HPN-01525 | 4-Br-phenyl | 4-(H2NSO2)-phenyl | -C(O)-cyclopropyl | H | C23H20BrN3O4S | 514.39 |
| HPN-01526 | 4-Br-phenyl | 4-(NH2C(O)NH)-phenyl | -C(O)CH2CH2NH2 | H | C23H21BrN4O4 | 497.34 |
| HPN-01527 | 4-Br-phenyl | 4-(H2NSO2)-phenyl | -C(O)CH2NH2 | H | C21H19BrN4O4S | 503.37 |
| HPN-01529 | 4-Cl-phenyl | 4-(H2NSO2)-phenyl | -C(O)-3-pyridyl | H | C25H19ClN4O4S | 506.96 |
| HPN-01530 | 4-Cl-phenyl | 4-(H2NSO2)-phenyl | -C(O)CH2CH2NH2 | H | C22H21ClN4O4S | 472.94 |

Fig. 36 Cont'd

| Compound No. | Structures | | | | Molecular Formula | MW |
|---|---|---|---|---|---|---|
| | R1 | R2 | R3 | R4 | | |
| HPN-01531 | 4-Cl-phenyl | 4-(SO2NH2)-phenyl | CH2CH2CH2OH | H | C21H20ClN3O4S | 445.92 |
| HPN-01532 | 4-Cl-phenyl | 4-(SO2NH2)-phenyl | CH2-(3-Cl-phenyl) | H | C26H21Cl2N3O3S | 526.43 |
| HPN-01533 | 4-Cl-phenyl | 4-(SO2NH2)-phenyl | n-butyl | H | C23H24ClN3O3S | 457.97 |
| HPN-01534 | 4-Cl-phenyl | 4-(SO2NH2)-phenyl | CH2CH2-phenyl | H | C27H24ClN3O3S | 506.02 |
| HPN-01601 | 4-Cl-phenyl | 4-(SO2NH2)-phenyl | H | (substituent) | C20H18ClN3O3S | 415.89 |
| HPN-01602 | 4-Br-phenyl | 4-(SO2NH2)-phenyl | H | (substituent) | C20H18BrN3O3S | 460.34 |

Fig. 36 Cont'd

| Compound No. | Structures | | | | Molecular Formula | MW |
|---|---|---|---|---|---|---|
| | R1 | R2 | R3 | R4 | | |
| HPN-01603 | 4-Cl-phenyl | 4-sulfamoyl-phenyl | H | butyl (branched) | C22H22ClN3O3S | 443.95 |
| HPN-01604 | 4-Br-phenyl | 4-sulfamoyl-phenyl | H | butyl (branched) | C22H22BrN3O3S | 488.4 |
| HPN-01605 | 4-Cl-phenyl | 4-sulfamoyl-phenyl | H | cyclopropylmethyl | C22H20ClN3O3S | 441.93 |
| HPN-01606 | 4-Br-phenyl | 4-sulfamoyl-phenyl | H | cyclopropylmethyl | C22H20BrN3O3S | 486.38 |
| HPN-01607 | 4-Cl-phenyl | 4-sulfamoyl-phenyl | H | hydroxypropyl | C21H20ClN3O4S | 445.92 |
| HPN-01608 | 4-Br-phenyl | 4-sulfamoyl-phenyl | H | hydroxypropyl | C21H20BrN3O4S | 490.37 |

Fig. 36 Cont'd

| Compound No. | Structures | | | | Molecular Formula | MW |
|---|---|---|---|---|---|---|
| | R1 | R2 | R3 | R4 | | |
| HPN-01609 | 4-Cl-phenyl | 4-SO2NH2-phenyl | | | C20H14ClN3O4S | 427.86 |
| HPN-01610 | 4-Br-phenyl | 4-SO2NH2-phenyl | | | C20H14BrN3O4S | 472.31 |
| HPN-01611 | 4-Cl-phenyl | 4-SO2NH2-phenyl | H | phenyl | C25H20ClN3O3S | 477.96 |
| HPN-01612 | 4-Br-phenyl | 4-SO2NH2-phenyl | H | phenyl | C25H20BrN3O3S | 522.42 |
| HPN-01613 | 4-Cl-phenyl | 4-SO2NH2-phenyl | H | 3-F-phenyl | C25H19ClFN3O3S | 495.95 |
| HPN-01614 | 4-Br-phenyl | 4-SO2NH2-phenyl | H | 3-F-phenyl | C25H19BrFN3O3S | 540.41 |

Fig. 36 Cont'd

| Compound No. | Structures | | | | Molecular Formula | MW |
|---|---|---|---|---|---|---|
| | R1 | R2 | R3 | R4 | | |
| HPN-01615 | 4-Cl-phenyl | 4-(SO2NH2)-phenyl | H | 3,4-diF-phenyl | C25H18ClF2N3O3S | 513.94 |
| HPN-01616 | 4-Br-phenyl | 4-(SO2NH2)-phenyl | H | 3,4-diF-phenyl | C25H18BrF2N3O3S | 558.4 |
| HPN-01617 | 4-Cl-phenyl | 4-(SO2NH2)-phenyl | H | 3,4-diOH-phenyl | C25H20ClN3O5S | 509.96 |
| HPN-01618 | 4-Br-phenyl | 4-(SO2NH2)-phenyl | H | 3,4-diOH-phenyl | C25H20BrN3O5S | 554.41 |
| HPN-01619 | 4-Cl-phenyl | 4-(SO2NH2)-phenyl | H | 3-OMe-phenyl | C26H22ClN3O4S | 507.99 |
| HPN-01620 | 4-Br-phenyl | 4-(SO2NH2)-phenyl | H | 3-OMe-phenyl | C26H22BrN3O4S | 552.44 |

Fig. 36 Cont'd

| Compound No. | Structures | | | | Molecular Formula | MW |
|---|---|---|---|---|---|---|
| | R1 | R2 | R3 | R4 | | |
| HPN-01621 | 4-Cl-phenyl | 4-(SO2NH2)-phenyl | H | piperidine-NH | C22H23ClN4O2S | 442.96 |
| HPN-01622 | 4-Br-phenyl | 4-(SO2NH2)-phenyl | H | piperidine-NH | C22H23BrN4O2S | 487.41 |
| HPN-01623 | 4-Cl-phenyl | 4-(SO2NH2)-phenyl | H | piperidine-N-C(O)NH2 | C23H24ClN5O3S | 585.99 |
| HPN-01624 | 4-Br-phenyl | 4-(SO2NH2)-phenyl | H | piperidine-N-C(O)NH2 | C23H24BrN5O3S | 487.42 |
| HPN-01625 | 4-Cl-phenyl | 4-(SO2NH2)-phenyl | H | pyridyl | C24H19ClN4O3S | 478.95 |
| HPN-01626 | 4-Cl-phenyl | 4-(SO2NH2)-phenyl | H | pyrrole | C23H19ClN4O3S | 466.94 |

Fig. 36 Cont'd

| Compound No. | Structures | | | | Molecular Formula | MW |
|---|---|---|---|---|---|---|
| | R1 | R2 | R3 | R4 | | |
| HPN-01627 | 4-Cl-phenyl | 4-sulfamoylphenyl | H | thiophen-3-yl | C23H18ClN3O3S2 | 483.99 |
| HPN-01628 | 4-Cl-phenyl | 4-sulfamoylphenyl | H | 1H-pyrrol-3-yl | C23H19ClN4O3S | 466.94 |
| HPN-01629 | 4-Cl-phenyl | 4-sulfamoylphenyl | H | (1H-pyrrol-2-yl)methyl | C24H21ClN4O3S | 480.97 |
| HPN-01630 | 4-Cl-phenyl | 4-sulfamoylphenyl | H | pyridin-3-ylmethyl | C25H21ClN4O3S | 492.98 |

AMINO-ARYL-BENZAMIDE COMPOUNDS AND METHODS OF USE THEREOF

CROSS REFERENCE TO RELATED APPLICATIONS

This application is a continuation of U.S. patent application Ser. No. 15/971,496, filed May 4, 2018; which claims the benefit of U.S. Provisional Patent Application No. 62/502,385, filed May 5, 2017; and U.S. Provisional Patent Application No. 62/539,036, filed Jul. 31, 2017; the disclosures of each of which are incorporated herein by reference.

FIELD OF THE INVENTION

The present invention relates to amino-aryl-benzamide compounds and preparation methods thereof. The present invention further relates to the treatment and/or reduction of nonalcoholic fatty liver disease (NAFLD) and nonalcoholic steatohepatitis (NASH) using such compositions.

BACKGROUND OF THE INVENTION

Nonalcoholic fatty liver disease (NAFLD) is the most common chronic liver disease in the world and its incidence is increasing due to a close association with obesity and insulin resistance. NAFLD represents a spectrum of liver disease that includes simple steatosis (triacylglycerol (TAG) infiltration in >5 percent of hepatocytes), fatty infiltration plus inflammation, and hepatocellular ballooning degeneration (nonalcoholic steatohepatitis, NASH), progressing to liver fibrosis and ultimately cirrhosis (Hardy et al., 2016 *Annual Reviews of Pathology*). Among those with NAFLD, around 25 percent will progress to the more severe form of NASH, which is a major health issue due to its association with increased cardiovascular mortality, type 2 diabetes, and significant risk of end-stage liver disease, including fibrosis, cirrhosis and hepatocellular carcinoma (HCC) (Targher et al., 2010 *NEJM*). 5-25 percent of NASH patients will develop cirrhosis within 7 years, and 4-27 percent of patients will ultimately develop liver cancer. Indeed, NASH is associated with a greater than 10-fold increased risk of liver-related death, and a doubling of cardiovascular risk (Ekstedt et al., 2006 *Hepatology*).

In the US, between 30 and 40 percent of adults have NAFLD (Spengler and Loomba, 2015 *Mayo Clinic Proceedings*), and the prevalence of this condition is rising, possibly due to the increasing number of Americans with obesity (*National Digestive Diseases Information Clearinghouse, NIDDK*). A recent prospective cohort study using ultrasound and liver biopsy approaches suggested the prevalence of NAFLD in asymptomatic middle-aged patients to be 46.0 percent and the prevalence of NASH to be 12.2 percent (Williams et al., 2011 *Gastroenterology*). As the incidence of cirrhosis due to chronic viral hepatitis decreases, NAFLD/NASH is poised to become the primary indication for liver transplantation globally (Charlton et al., 2011 *Gastroenterology*).

Until recently, the sequential "two-hit hypothesis" has been widely accepted to explain the pathogenesis of NAFLD/NASH. Indeed, the combined effects of various biochemical and immunological processes ("multiple parallel hits") are attributed to the development of NAFLD/NASH. Sequentially, hepatic steatosis is induced by an early stress response through which lipotoxic free fatty acids (FFAs) are partitioned into relatively stable TAG stores. Lipotoxicity develops when adaptive mechanisms that mitigate the deleterious effects of fatty acid in the liver are overwhelmed, leading to the generation of reactive oxygen species (ROS), ER stress, and cellular dysfunction. Subsequently, cellular damage triggers a mixture of immune-mediated hepatocellular injury and cell death pathways. Once these persist, hepatic stellate cells (HSCs) are activated, leading to collagen deposition and hepatic fibrogenesis (Hardy et al., 2016 *Annual Reviews of Pathology*). Eventually, these events cause cirrhosis that may result in liver failure and HCC (Richardson et al., 2007 *Gastroenterology*).

The main focuses for NAFLD/NASH treatments are reversing hepatic steatosis, as well as reducing progression to advanced fibrosis, cirrhosis and its sequelae, including HCC, metabolic diseases and cardiovascular diseases. At present, there are no approved pharmacological therapies for NAFLD/NASH. The only treatment option is weight loss, associated with lifestyle modifications. However, such treatment methods require a great deal of commitment, and compliance can be difficult. Thus, there is a pressing need to develop novel and effective therapeutics for this devastating human disease. The present invention addresses this need.

SUMMARY

The present disclosure provides a method of treating nonalcoholic fatty liver disease (NAFLD) in a subject, the method comprising administering to the subject a therapeutically effective amount of a compound selected from the group consisting of a compound of Formula I, Formula II, Formula III, Formula IV, or a prodrug, therapeutically active metabolite, hydrate, solvate, or pharmaceutically acceptable salt thereof, wherein, Formula I is:

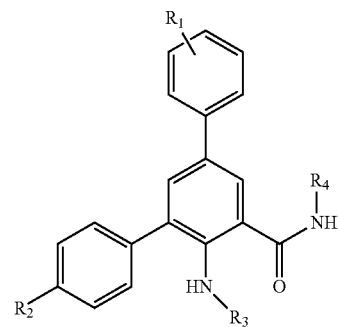

wherein R1 is a halogen, R2 is a sulfoxide group, and R3 and R4 are independently hydrogen or lower alkyl;

wherein Formula II is:

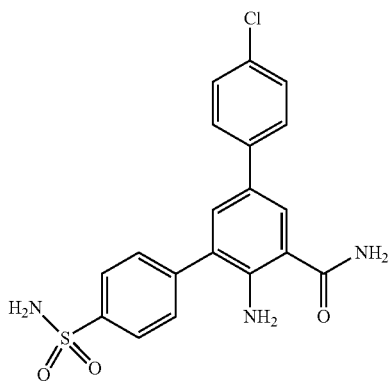 [SMILES: NC(=O)c1cc(-c2ccc(Cl)cc2)cc(-c2ccc(S(N)(=O)=O)cc2)c1N]

and Formula III is:

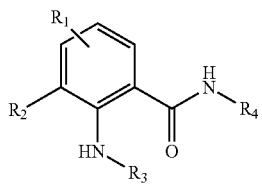

wherein:
$R_1$ is —CHCHR$_5$; —CHCHCO$_2$R$_5$; —CHCHCONHR$_5$; -phenyl; -phenyl-R$_5$; —CCR$_5$; —CC—CH$_2$R$_5$; —OR$_5$; —SR$_5$; or —NHR$_5$;
$R_2$ is —C$_6$H$_5$—R$_6$; —OC$_6$H$_5$—R$_6$; —SC$_6$H$_5$—R$_6$; —NHC$_6$H$_5$—R$_6$; —OC$_{1-6}$ alkyl-C$_6$H$_4$—R$_6$; —NHC$_{1-6}$ alkyl-C$_6$H$_4$—R$_6$; piperazine-R$_6$; or pyridine-R$_6$;
$R_3$ is H; —C$_{1-6}$ alkyl optionally substituted with —OH, —NH$_2$, phenyl, or halogen; —CO-pyridine; —CO—CH$_2$CH$_2$NH$_2$; or —CO—C$_{1-6}$ alkyl optionally substituted with —OH or —NH$_2$;
$R_4$ is H; —OCH$_3$; -piperidine; -piperidine-CONH$_2$; -pyridine; -pyrrole; -thiophene; —C$_{1-6}$ alkyl optionally substituted with —OH; -pyridine; -piperidine; -pyrrole; -thiophene; or -phenyl optionally substituted with halogen or hydroxy;
or, $R_3$ and $R_4$ together form uracil;
$R_5$ is halogen; —COOH; C$_{1-6}$ cycloalkyl; —CH$_2$C$_6$H$_5$; —CH$_2$CH$_2$C$_6$H$_5$; —CH$_2$CH$_2$C$_6$H$_5$—F; CH$_2$C$_6$H$_5$—COOH; —CH$_2$C$_6$H$_5$—OH; —CH$_2$-furan; —Si(CH$_2$)$_3$; —CH$_2$CO$_2$CH$_3$; —CH$_2$CO$_2$(CH$_2$)$_2$CH$_3$; or —CH$_2$CO$_2$C$_6$H$_5$—Cl; or
—C$_{1-10}$ alkyl optionally substituted with halogen or —OH; or
—C$_{1-10}$ cycloalkyl optionally substituted with halogen or —OH; or
-phenyl optionally substituted with halogen, —OH, —CH$_3$, —C$_{1-10}$ alkyl, OCO—C$_{1-4}$ alkyl, —NHCOMe, —NHCO(CH$_2$)$_2$CH$_3$, —COOH, —OC$_{1-10}$ alkyl, or —CO$_2$—C$_{1-4}$ alkyl; or
-pyridine optionally substituted with halogen, —OH, —CH$_3$, —C$_{1-10}$ alkyl, OCO—C$_{1-4}$ alkyl, —NHCOMe, —NHCO(CH$_2$)$_2$CH$_3$, —COOH, —OC$_{1-10}$ alkyl, or —CO$_2$—C$_{1-4}$ alkyl; or
-pyrrole optionally substituted with halogen, —OH, —CH$_3$, —C$_{1-10}$ alkyl, OCO—C$_{1-4}$ alkyl, —NHCOMe, —NHCO(CH$_2$)$_2$CH$_3$, —COOH, —OC$_{1-10}$ alkyl, or —CO$_2$—C$_{1-4}$ alkyl;

$R_6$ is —SO$_2$NH$_2$; —OPO(OH)$_2$; —NH$_2$; —NHCONH$_2$; —NHCOCH$_3$; —NHCSCH$_3$; —NHCSCH$_2$CH$_3$; —NHCS(CH$_2$)$_2$CH$_3$; tetrazole; —SO$_2$NH(CH$_2$)$_2$CH$_3$; —NHC(NH)NH$_2$; —NHCSNH$_2$; —NHCSCH$_2$OH; triazole; oxoimidazol; —SO$_2$NHCH$_2$CH$_2$OH; —NHCONH—C$_{1-6}$ alkyl; or —NHCONH-pyridine;

and wherein Formula IV is:

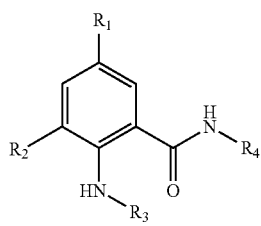

wherein R1 is selected from the groups listed in Table 1;

TABLE 1

| Formula IV, R1 Options |
|---|
| 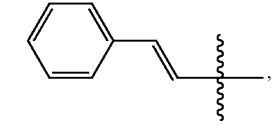 |
| 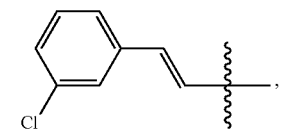 [SMILES: */C=C/c1cccc(Cl)c1] |
| 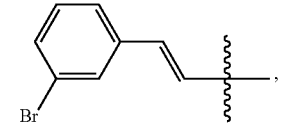 |
| 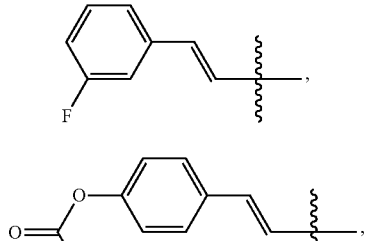 |
| 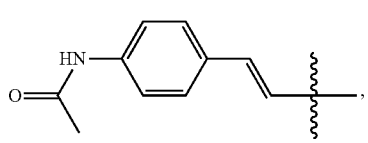 [SMILES: */C=C/c1ccc(NC(C)=O)cc1] |
| 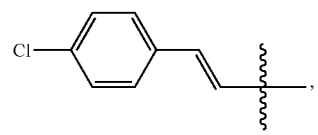 [SMILES: */C=C/c1ccc(Cl)cc1] |

TABLE 1-continued
Formula IV, R1 Options
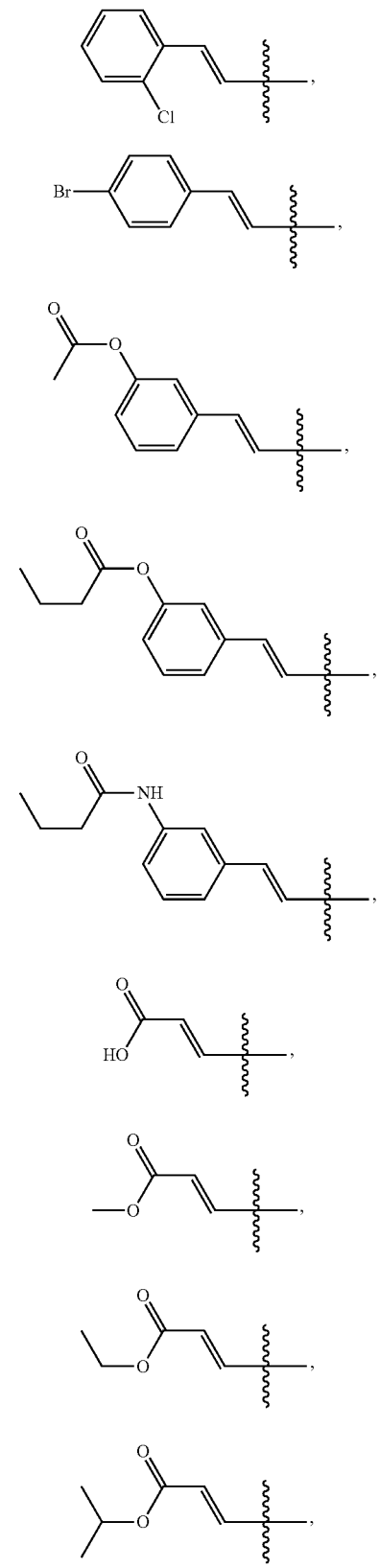
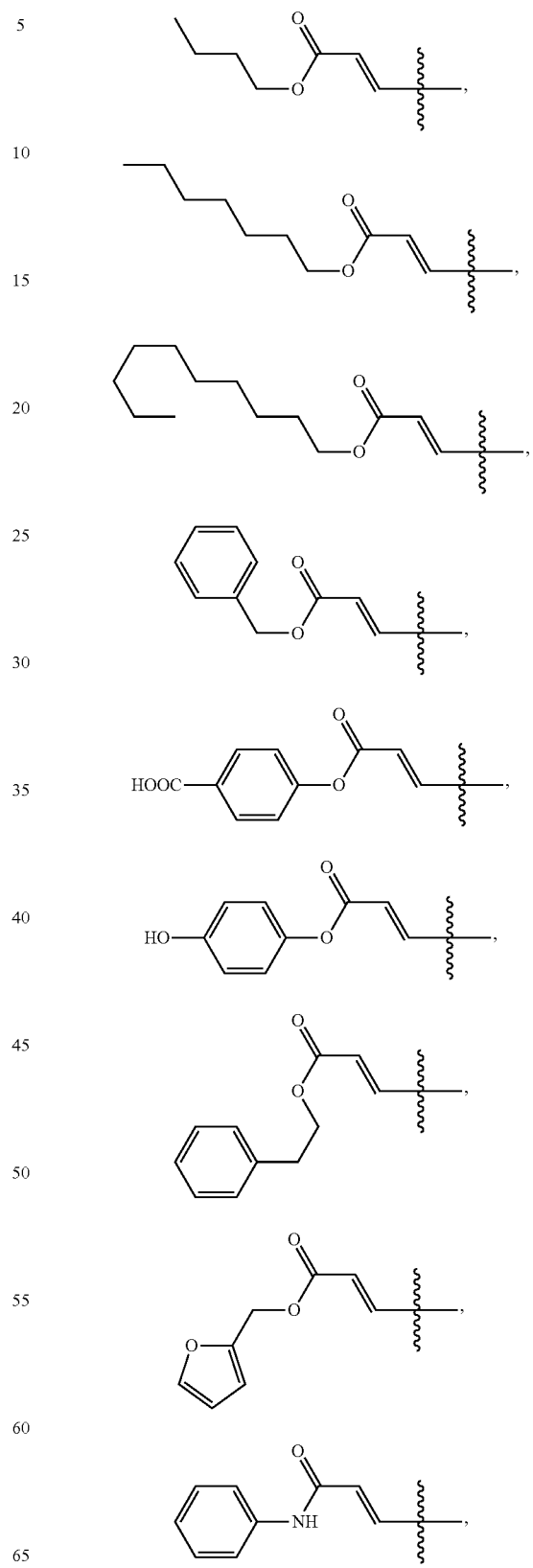

TABLE 1-continued

Formula IV, R1 Options (Structures shown: various R1 substituent options including N-aryl/alkyl acrylamides and aryl/alkyl alkynes)

TABLE 1-continued
Formula IV, R1 Options
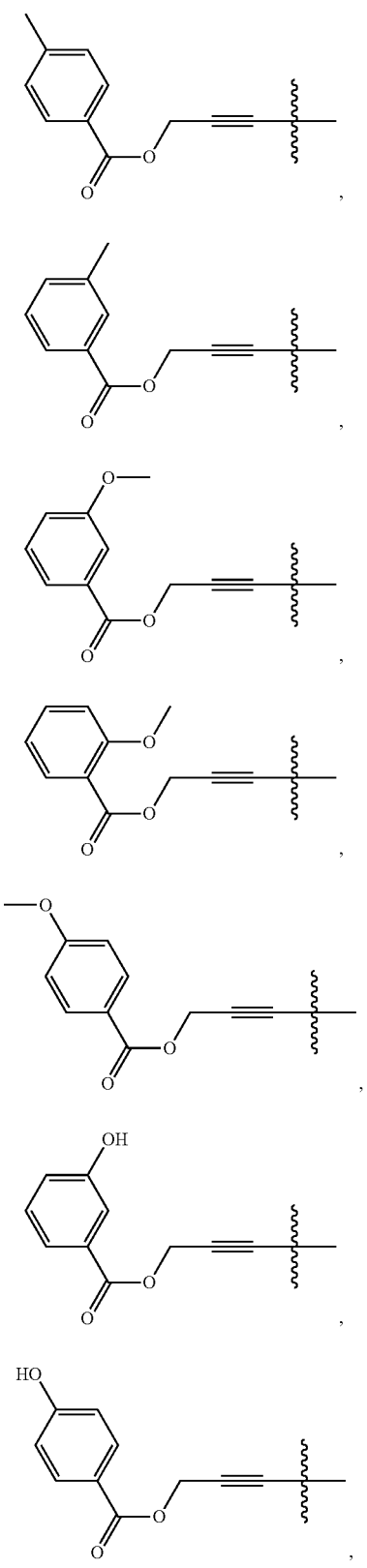
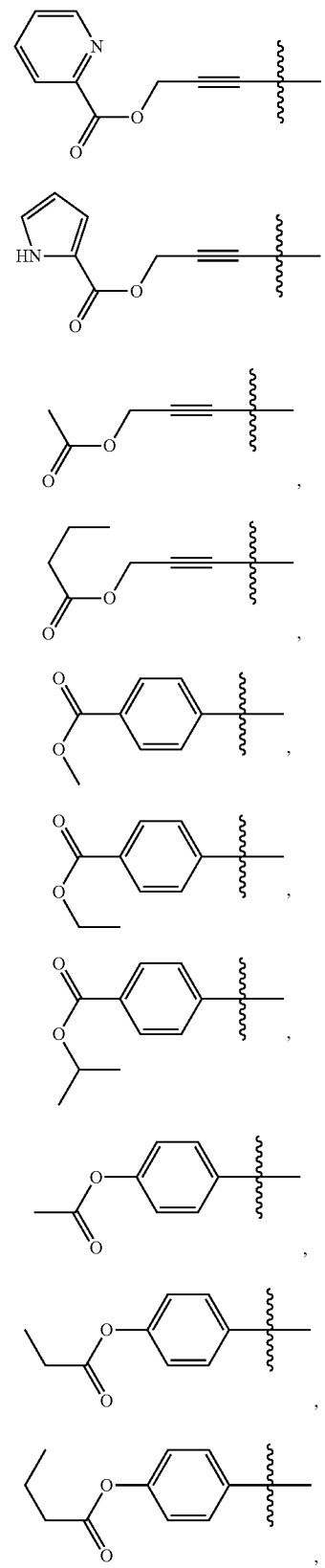

TABLE 1-continued
Formula IV, R1 Options
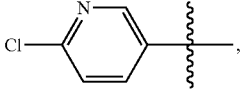,
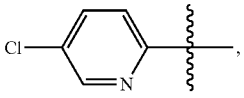,
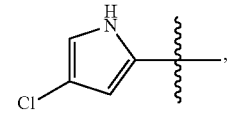 [SMILES: *c1cc(Cl)c[nH]1],
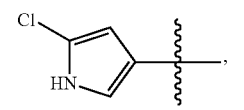 [SMILES: *c1c[nH]c(Cl)c1],
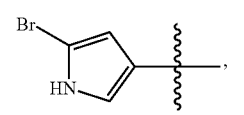,
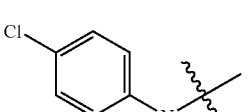,
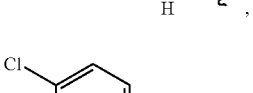,
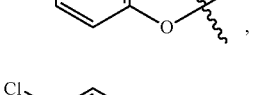,
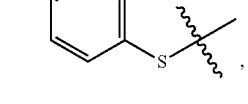,
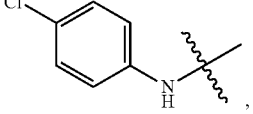,
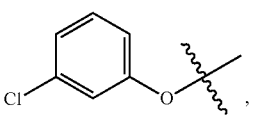 [SMILES: *Oc1cccc(Cl)c1],
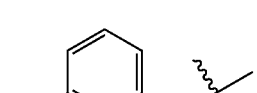,
TABLE 1-continued
Formula IV, R1 Options
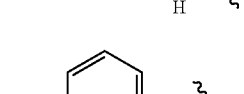,
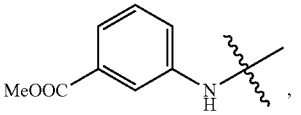,
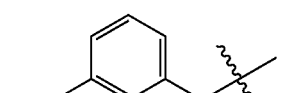,
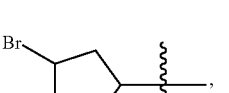,
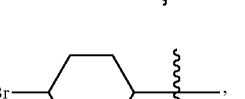,
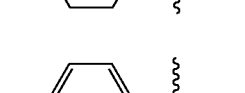
wherein R2 is selected from the groups listed in Table 2;
TABLE 2
Formula IV, R2 Options
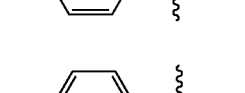,
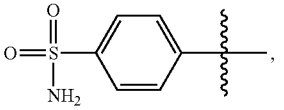 [SMILES: *c1ccc(S(N)(=O)=O)cc1],
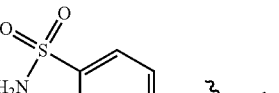,
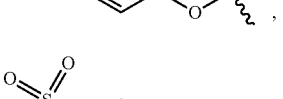, TABLE 2-continued
Formula IV, R2 Options
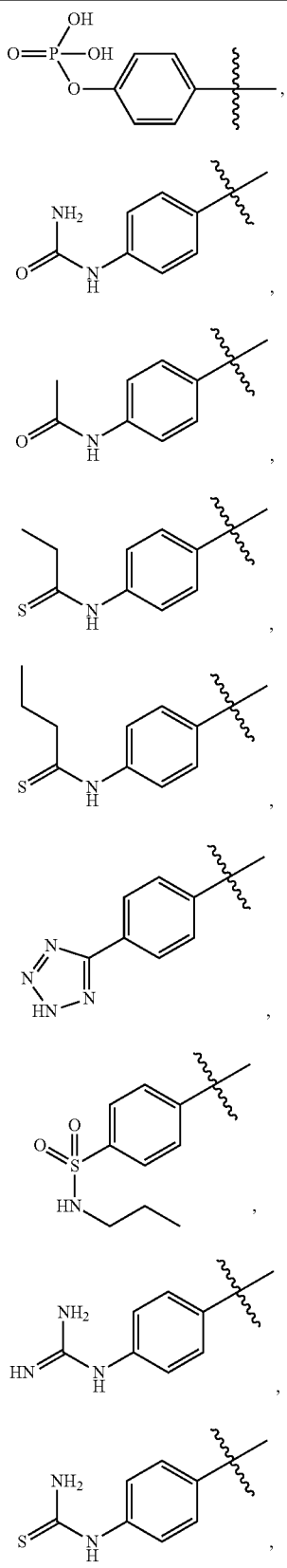
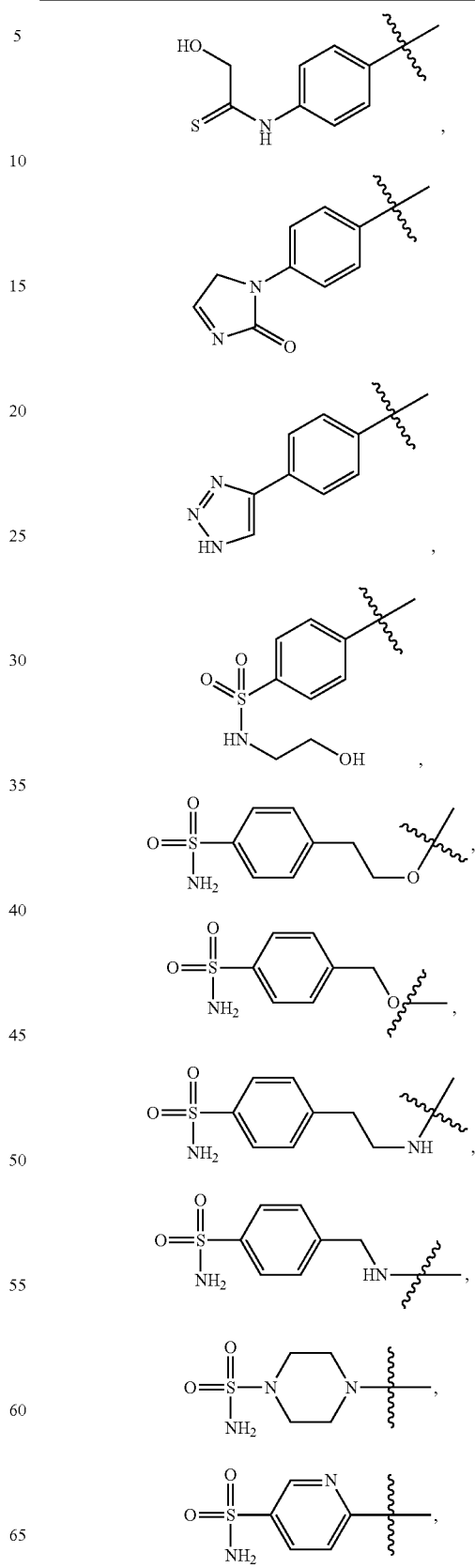

TABLE 2-continued
Formula IV, R2 Options
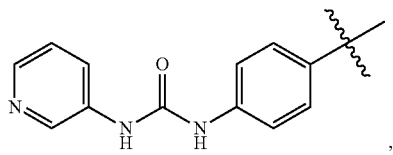
,
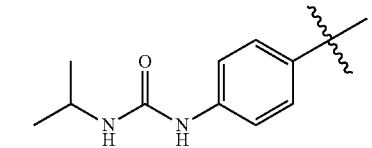
,
wherein R3 is selected from the groups listed in Table 3;
TABLE 3
Formula IV, R3 Options
H,
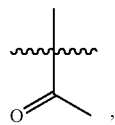 [SMILES: *C(C)=O]
,
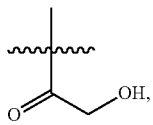
,
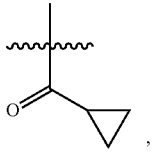 [SMILES: *C(=O)C1CC1]
,
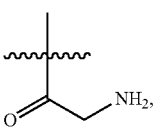
,
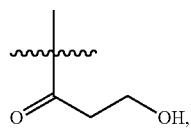
,
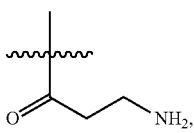
,
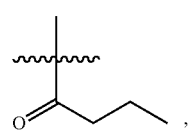 [SMILES: *C(=O)CCC]
,
TABLE 3-continued
Formula IV, R3 Options
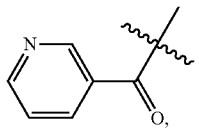 [SMILES: *C(=O)c1cccnc1]
,
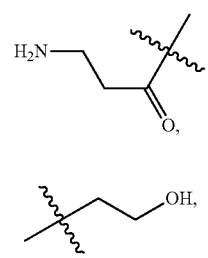
,
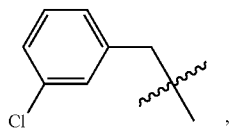 [SMILES: *Cc1cccc(Cl)c1]
,
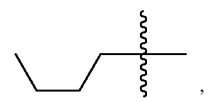
,
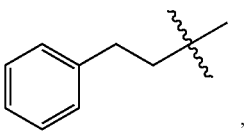 [SMILES: *CCc1ccccc1]
,
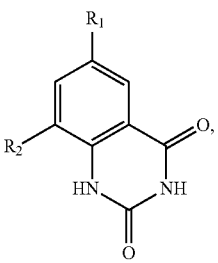
and
wherein R4 is selected from the groups listed in Table 4.
TABLE 4
Formula IV, R4 Options
H, ,
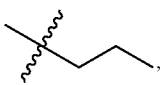, 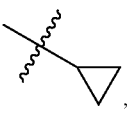, TABLE 4-continued Formula IV, R4 Options

[Chemical structures showing R4 options including: propanol chain with OH; quinazolinedione with R1 and R2 substituents; phenyl; 3-fluorophenyl; 3,4-difluorophenyl; 3,4-dihydroxyphenyl; 3-methoxyphenyl; piperidine-NH; piperidine-carboxamide; pyridine; pyrroline; thiophene; pyrrole-NH; pyrrole-methyl-NH; pyridylmethyl]

In a further embodiment of the invention, the NAFLD comprises a condition selected from the group consisting of fatty infiltration plus inflammation, nonalcoholic steatohepatitis (NASH), liver fibrosis, cirrhosis, and combinations thereof.

In a further embodiment of the invention, the compound is administered in a dose of between about 1 mg/kg to about 100 mg/kg body weight of the subject/day.

In a further embodiment of the invention, the compound is administered once per day.

In a further embodiment of the invention, R1 is chloride.

In a further embodiment of the invention, R2 is $SO_2NH_2$.

In a further embodiment of the invention, R3 is hydrogen.

In a further embodiment of the invention, R4 is hydrogen.

In a further embodiment of the invention, the method comprises using a compound of Formula I, or a prodrug, therapeutically active metabolite, hydrate, solvate, or pharmaceutically acceptable salt thereof.

In a further embodiment of the invention, the method comprises using a compound of Formula II, or a prodrug, therapeutically active metabolite, hydrate, solvate, or pharmaceutically acceptable salt thereof.

In a further embodiment of the invention, the method comprises using a compound of Formula III, or a prodrug, therapeutically active metabolite, hydrate, solvate, or pharmaceutically acceptable salt thereof.

In a further embodiment of the invention, the method comprises using a compound of Formula IV, or a prodrug, therapeutically active metabolite, hydrate, solvate, or pharmaceutically acceptable salt thereof.

In a further embodiment of the invention, the method comprises using a compound selected from the group consisting of HPN-01101-01133; HPN-01201-01224; HPN-01301-01322; HPN-01401-01430; HPN-01501-01506; HPN-01513-01520; HPN-01525-01527; HPN-01529-01534; HPN-01601-01630 and prodrugs, therapeutically active metabolites, hydrates, solvates, and pharmaceutically acceptable salts thereof.

One embodiment of the invention is a compound of Formula I, Formula II, Formula III, Formula IV or a prodrug, therapeutically active metabolite, hydrate, solvate, or pharmaceutically acceptable salt thereof, for use in treating liver disease. In certain embodiments, the disease being treated is nonalcoholic fatty liver disease (NAFLD) in a subject.

One embodiment of the invention is a kit for treating NAFLD, the kit comprising a compound of Formula I, Formula II, Formula III, Formula IV or a prodrug, therapeutically active metabolite, hydrate, solvate, or pharmaceutically acceptable salt thereof, and instructions for administering the compound to a subject having, or at risk for, NAFLD, or a related condition, such as, fatty deposit-related inflammation, non-alcoholic steatohepatitis (NASH), liver fibrosis, cirrhosis, or combinations thereof.

One embodiment of the invention is a compound of Formula III, Formula IV, or a prodrug, therapeutically active metabolite, hydrate, solvate, or pharmaceutically acceptable salt thereof, wherein the compound is not Formula II.

One embodiment of the invention is a pharmaceutical composition comprising a compound of Formula III, Formula IV, or a prodrug, therapeutically active metabolite, hydrate, solvate, or pharmaceutically acceptable salt thereof, wherein the compound is not Formula II.

One embodiment of the invention is use of a compound of Formula III, Formula IV, or a prodrug, therapeutically active metabolite, hydrate, solvate, or pharmaceutically acceptable salt thereof, wherein the compound is not Formula II, or a pharmaceutical composition of the disclosure, in the preparation of a medicament for treating a subject having, or at risk for, NAFLD, or a related condition, such as, fatty deposit-related inflammation, non-alcoholic steatohepatitis (NASH), liver fibrosis, cirrhosis, or combinations thereof.

BRIEF DESCRIPTION OF THE FIGURES

FIGS. 5A-5D. Effect of HPN-01 on hepatocellular lipid droplet (LD) biogenesis. Hepatoma cell line Huh7 cells were treated with various amounts of HPN-01 for 24 hours, either in the absence or in the presence of 400 μM oleic acid, which triggers LD formation, after which intracellular LD contents were observed using a Zeiss confocal microscope with fluorescence. FIG. 5A) Fluorescent analysis of untreated (DMSO) or HPN-01-treated cells in the absence (Top panels) and presence (Bottom panels) of oleic acid. Cellular LD contents were stained using BODIPY 493/503 and are shown in green. Blue indicates cell nuclei. FIG. 5B) LD size of treated and untreated (DMSO) cells, in the presence or absence of oleic acid. FIG. 5C) Mean fluorescence intensity of untreated (DMSO) and treated cells in the absence of oleic acid. FIG. 5D) Mean fluorescence intensity of untreated (DMSO) and treated cells in the presence of oleic acid.

FIG. 12A) Body weight change in untreated mice fed a normal chow diet (NCD; circles), untreated mice fed a high fat diet (NFD vehicle; squares), and treated mice fed a high fat diet (HFD HPN-01; triangles) shows that HPN-01 treatment reversed HFD-triggered obesity. FIG. 12B) Post-sacrifice examination of mouse internal organs showed that HPN-01 significantly alleviated visceral fat accumulation (FIG. 12B).

FIG. 13A) Haematoxylin and eosin (H&E) staining of liver tissue sections from mice. FIG. 13B) Mouse liver tissue sections stained with Oil-red-O.

FIG. 16A) Plasma cholesterol levels in untreated and treated mice fed a high fat diet (HFD). FIG. 16B) Plasma triglyceride levels in untreated and treated mice fed a high fat diet (HFD).

FIG. 18A) α-SMA expression levels in mice fed normal cow diet (NCD), and untreated (Vehicle) and treated (HPN-01) mice fed a high fat diet (HFD). FIG. 18B) COL1α expression levels in mice fed normal cow diet (NCD), and untreated (Vehicle) and treated (HPN-01) mice fed a high fat diet (HFD).

FIG. 26. High resolution mass spectrometry of HPN-01.

FIG. 28A) body weight changes in untreated mice fed a normal chow diet (Naïve; gray circles), vehicle-treated mice fed a high fat diet (Vehicle; black squares), telmisartan-treated mice fed a high fat diet (Telmisartan; gray upper arrow triangles), low-dose HPN-01-treated mice fed a high fat diet (HPN-01 5mpk; gray lower arrow triangles), and high-dose HPN-01-treated mice fed a high fat diet (HPN-01 15mpk; black diamonds). FIG. 28B) Daily and cumulative food intake recorded for each study group.

FIG. 30A) serum ALT levels in untreated, vehicle treated, Telmisartan treated, and HPN-01 treated mice. FIG. 30B) serum AST levels in untreated and treated mice. FIG. 30A) serum ALT levels in untreated, vehicle treated, Telmisartan treated, and HPN-01 treated mice.

FIG. 31A) serum TC concentrations in untreated, vehicle treated, Telmisartan treated, and HPN-01 treated mice. FIG. 31B) serum TG concentrations in untreated, vehicle treated, Telmisartan treated, and HPN-01 treated mice.

FIG. 32A) liver TC concentrations in untreated, vehicle treated, Telmisartan treated, and HPN-01 treated mice. FIG. 32B) liver TG concentrations in untreated, vehicle treated, Telmisartan treated, and HPN-01 treated mice.

FIG. 33A) relative TNF-α mRNA levels in livers from untreated, vehicle treated, Telmisartan treated, and HPN-01 treated mice. FIG. 33B) relative MCP-1 mRNA levels in livers from untreated, vehicle treated, Telmisartan treated, and HPN-01 treated mice.

FIG. 34A) relative levels of transforming growth factor beta 1 (TGF-β1) mRNA in livers from untreated, vehicle treated, Telmisartan treated, and HPN-01 treated mice. FIG. 34B) relative levels of collagen type 1 alpha 1 (COL1A1) mRNA in livers from untreated, vehicle treated, Telmisartan treated, and HPN-01 treated mice. FIG. 34C) relative levels of metalloproteinase-1 (TIMP-1) mRNA in livers from untreated, vehicle treated, Telmisartan treated, and HPN-01 treated mice.

DETAILED DESCRIPTION OF THE INVENTION

Figure 1:
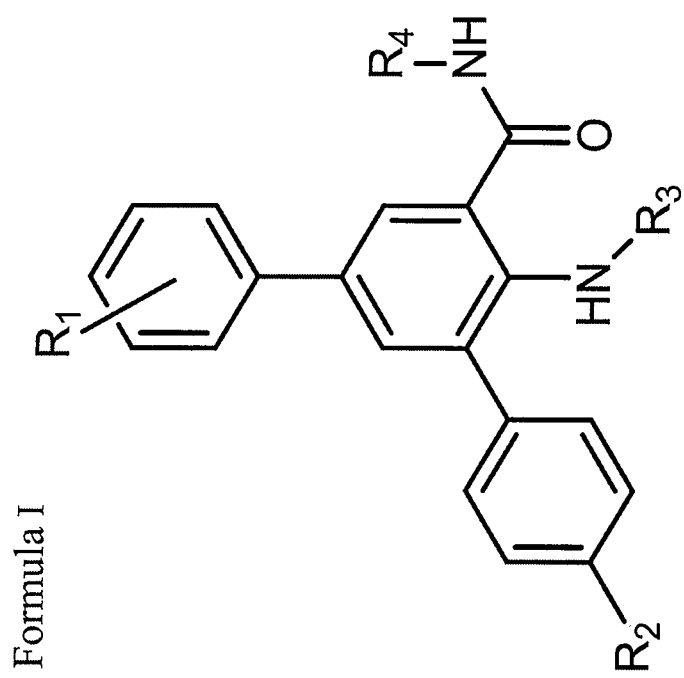
FIG. 1. Formula I. General structure of 2-amino-3,5-diarylbenzamide.

The present invention relates to a novel method for treating non-alcoholic fatty liver disease (NAFLD). More specifically, the present invention relates to a method of treating NAFLD by administering the 2-amino-arylbenzamide compound of the invention disclosed herein. It also relates to treating NAFLD-related conditions, such as, fatty deposit-related inflammation, non-alcoholic steatohepatitis (NASH), liver fibrosis, cirrhosis, and combinations thereof.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. For example, a compound refers to one or more compound molecules. As such, the terms "a", "an", "one or more" and "at least one" can be used interchangeably. Similarly, the terms "comprising", "including" and "having" can be used interchangeably. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed. All publications mentioned herein are incorporated herein by reference to disclose and describe the methods and/or materials in connection with which the publications are cited.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. The following terms and phrases, which are common to the various embodiments disclosed herein, are defined as follows:

The terms "individual", "subject", and "patient" are well-recognized in the art, and are herein used interchangeably to refer to any animal susceptible to developing NAFLD and related conditions. Examples include, but are not limited to, humans and other primates, including non-human primates such as chimpanzees and other apes and monkey species; farm animals such as cattle, sheep, pigs, seals, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms individual, subject, and patient by themselves, do not denote a particular age, sex, race, and the like. Thus, individuals of any age, whether male or female, are intended to be covered by the present disclosure and include, but are not limited to the elderly, adults, children, babies, infants, and toddlers. Likewise, the methods of the present invention can be applied to any race, including, for example, Caucasian (white), African-American (black), Native American, Native Hawaiian, Hispanic, Latino, Asian, and European.

As used herein, a therapeutically effective amount of a compound, disclosed herein, or a derivative or salt thereof, means an amount, that when administered to a subject is sufficient to treat the subject for NAFLD or related conditions such as NASH. Treating, treatment of, and the like, NAFLD, and related symptoms such as NASH, in a subject includes one or more of the following:

1. preventing the development of, or reducing the risk of developing, NAFLD, and/or related conditions such as fatty deposit-related inflammation, non-alcoholic steatohepatitis (NASH), liver fibrosis, cirrhosis, and combinations thereof. As used herein, the phrases preventing the development of, and the like, and reducing the risk of developing, and the like, mean that administration of a compound disclosed herein, or a derivative or salt thereof, results in a failure of the clinical symptoms of NAFLD, and related conditions such as NASH, to develop in a subject. Prior to treatment, the subject may, but need not, exhibit one or more risk factors for developing NAFLD, and related conditions, such as NASH;
2. inhibiting NAFLD, or related conditions such as NASH. As used herein, the terms inhibiting, arresting, and the like, mean stopping the further development of clinical symptoms of NAFLD, or related conditions such as fatty deposit-related inflammation, non-alcoholic steatohepatitis (NASH), liver fibrosis, cirrhosis, and combinations thereof, in a subject already diagnosed with NAFLD, or a related condition; and,
3. reducing NAFLD, or related conditions such as NASH. As used herein, the terms reducing, reversing, alleviating, and the like, mean that administration of a compound disclosed herein, or a derivative or salt thereof, causes a decrease in, or a cessation of, the number, frequency, duration, or severity, of clinical symptoms of NAFLD or a related condition, such as NASH, in an individual diagnosed with NAFLD or a related condition, such as fatty deposit-related inflammation, non-alcoholic steatohepatitis (NASH), liver fibrosis, cirrhosis, and combinations thereof.

It will be understood by those skilled in the art that a "therapeutically effective amount" of a compound disclosed herein, or a derivative or salt thereof, may vary for a particular subject, depending on such factors as the overall health and physical conditions of the subject, the extent of the NAFLD, or related condition such as NASH, the sex of the subject, and the age of the subject. It will be further understood that the "therapeutically effective amount" may fall within a broad range, based on factors such as those disclosed above, that can be determined through routine trials, methods for which are known to those skilled in the art.

As used herein, a compound of Formula I of the invention refers to a chemical compound having the structure shown below and in FIG. 1:

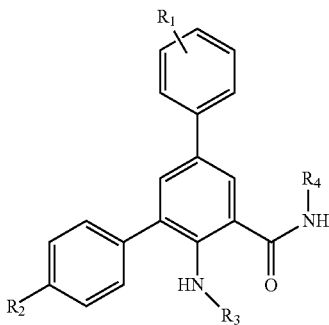

wherein R1 is a halogen, such as chlorine; R2 is a sulfoxide group, such as $SO_2NH_2$; and $R_3$ and $R_4$ are independently hydrogen or lower alkyl. A preferred example of a compound of Formula I is a compound in which $R_1$=Cl, $R_2$=$SO_2NH_2$, $R_3$=H and $R_4$=H, which is also referred to herein as HPN-01, and is shown below and in FIG. 2, and is referred to herein as Formula II:

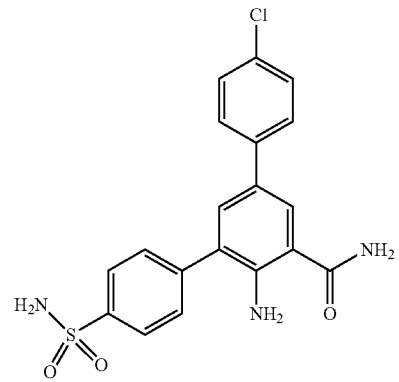 [SMILES: NC(=O)c1cc(-c2ccc(Cl)cc2)cc(-c2ccc(S(N)(=O)=O)cc2)c1N]

As a further example, a second compound of Formula I is a compound having the structure of Formula II, but in which the chlorine atom is replaced with another atom, such as iodine. Methods of making such compounds are illustrated herein and based on the teaching herein are within the skill of the art. Also within the scope of the invention is the use of prodrugs, therapeutically active metabolites, hydrates, solvates, and pharmaceutically acceptable salts of compounds of Formula I and Formula II. As used herein, a prodrug is a compound that, following administration to a subject, is metabolized to pharmacologically active form of the administered compound. The use and production of prodrugs is known to those skilled in the art.

Figure 3:
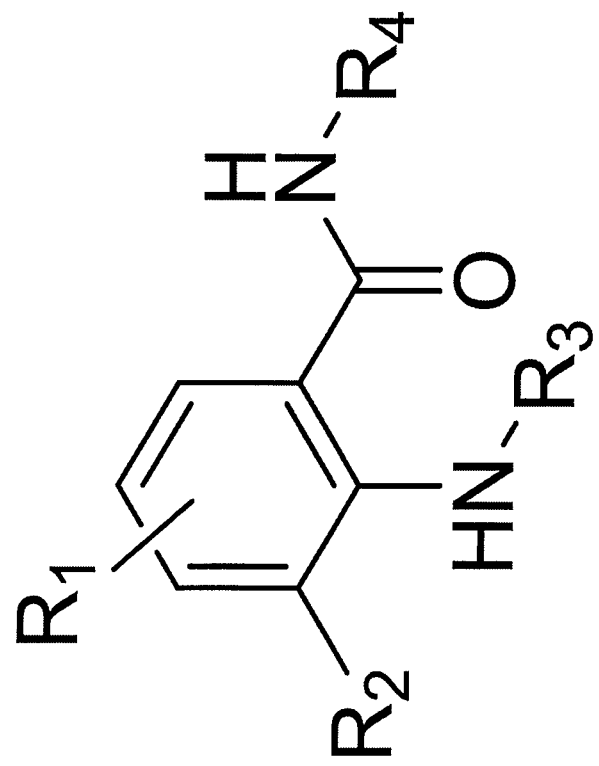
FIG. 3. Formula III.

As used herein, Formula III of the invention refers to a chemical compound having the structure shown below and in FIG. 3,

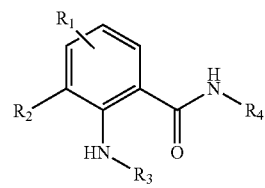

wherein:
$R_1$ is —$CHCHR_5$; —$CHCHCO_2R_5$; —$CHCHCONHR_5$; -phenyl; -phenyl-$R_5$; —$CCR_5$; —CC—$CH_2R_5$; —$OR_5$; —$SR_5$; or —$NHR_5$;
$R_2$ is —$C_6H_5$—$R_6$; —$OC_6H_5$—$R_6$; —$SC_6H_5$—$R_6$; —$NHC_6H_5$—$R_6$; —$OC_{1-6}$ alkyl-$C_6H_4$—$R_6$; —$NHC_{1-6}$ alkyl-$C_6H_4$—$R_6$; piperazine-R6; or pyridine-R6;
$R_3$ is H; —$C_{1-6}$ alkyl optionally substituted with —OH, —$NH_2$, phenyl, or halogen; —CO-pyridine; —CO—$CH_2CH_2NH_2$; or —CO—$C_{1-6}$ alkyl optionally substituted with —OH or —$NH_2$;
$R_4$ is H; —$OCH_3$; -piperidine; -piperidine-$CONH_2$; -pyridine; -pyrrole; -thiophene; —$C_{1-6}$ alkyl optionally substituted with —OH; -pyridine; -piperidine; -pyrrole; or -thiophene; or -phenyl optionally substituted with halogen, or hydroxy;

or, $R_3$ and $R_4$ together form uracil;

$R_5$ is halogen; —COOH; $C_{1-6}$ cycloalkyl; —CH$_2$C$_6$H$_5$; —CH$_2$CH$_2$C$_6$H$_5$; —CH$_2$CH$_2$C$_6$H$_5$—F; CH$_2$C$_6$H$_5$—COOH; —CH$_2$C$_6$H$_5$—OH; —CH$_2$-furan; —Si(CH$_2$)$_3$; —CH$_2$CO$_2$CH$_3$; —CH$_2$CO$_2$(CH$_2$)$_2$CH$_3$; or —CH$_2$CO$_2$C$_6$H$_5$—Cl; or —$C_{1-10}$ alkyl optionally substituted with halogen or —OH; or —$C_{1-10}$ cycloalkyl optionally substituted with halogen —OH; or phenyl optionally substituted with halogen, —OH, —CH$_3$, —C$_{1-10}$ alkyl, OCO—C$_{1-4}$ alkyl, —NHCOMe, —NHCO(CH$_2$)$_2$CH$_3$, —COOH, —OC$_{1-10}$ alkyl, or —CO$_2$—C$_{1-4}$ alkyl; or pyridine optionally substituted with halogen, —OH, —CH$_3$, —C$_{1-10}$ alkyl, OCO—C$_{1-4}$ alkyl, —NHCOMe, —NHCO(CH$_2$)$_2$CH$_3$, —COOH, —OC$_{1-10}$ alkyl, or —CO$_2$—C$_{1-4}$ alkyl; or pyrrole optionally substituted with halogen, —OH, —CH$_3$, —C$_{1-10}$ alkyl, OCO—C$_{1-4}$ alkyl, —NHCOMe, —NHCO(CH$_2$)$_2$CH$_3$, —COOH, —OC$_{1-10}$ alkyl, or —CO$_2$—C$_{1-4}$ alkyl;

$R_6$ is —SO$_2$NH$_2$; —OPO(OH)$_2$; —NH$_2$; —NHCONH$_2$; —NHCOCH$_3$; —NHCSCH$_3$; —NHCSCH$_2$CH$_3$; —NHCS(CH$_2$)$_2$CH$_3$; tetrazole; —SO$_2$NH(CH$_2$)$_2$CH$_3$; —NHC(NH)NH$_2$; —NHCSNH$_2$; —NHCSCH$_2$OH; triazole; oxoimidazol; —SO$_2$NHCH$_2$CH$_2$OH; —NHCONH—C$_{1-6}$ alkyl; or —NHCONH-pyridine.

In various embodiments, Formula III of the invention refers to a chemical compound having the structure shown above, wherein the structure does not include Formula II or alternatively, does not include Formula I.

Figure 4:
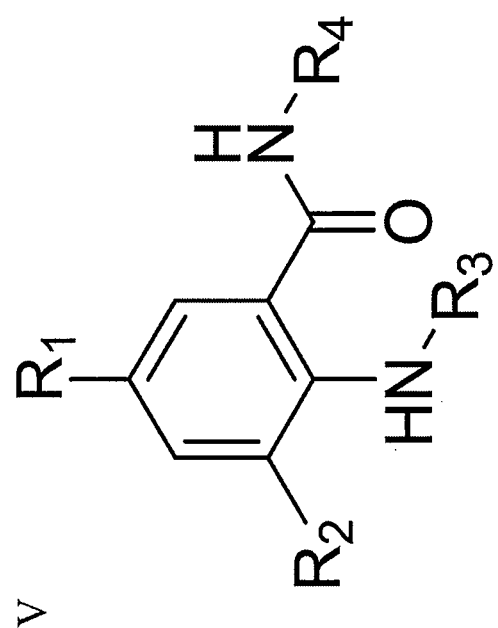
FIG. 4. Formula IV.

As used herein, Formula IV of the invention refers to a chemical compound having the structure shown below and in FIG. 4:

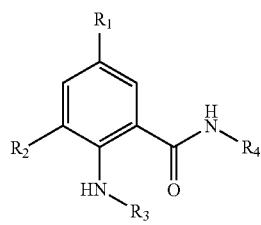

wherein R1 is selected from the groups listed in Table 1; R2 is selected from the groups listed in Table 2; R3 is selected from the groups listed in Table 3; and R4 is selected from the groups listed in Table 4.

TABLE 1

Formula IV, R1 Options

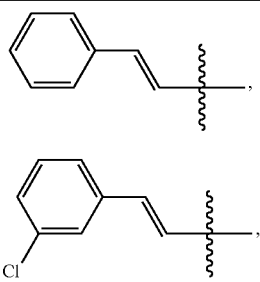

TABLE 1-continued

Formula IV, R1 Options

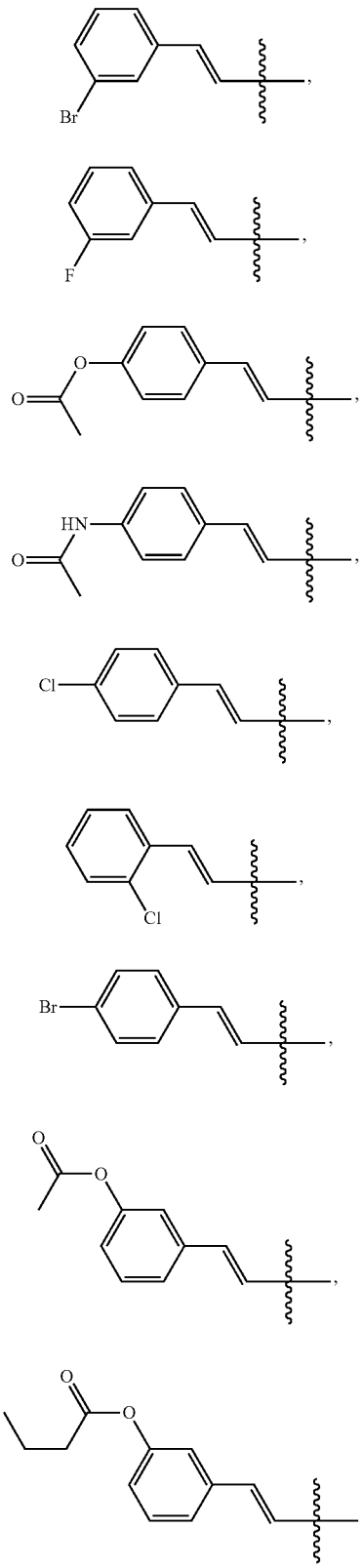

TABLE 1-continued
Formula IV, R1 Options
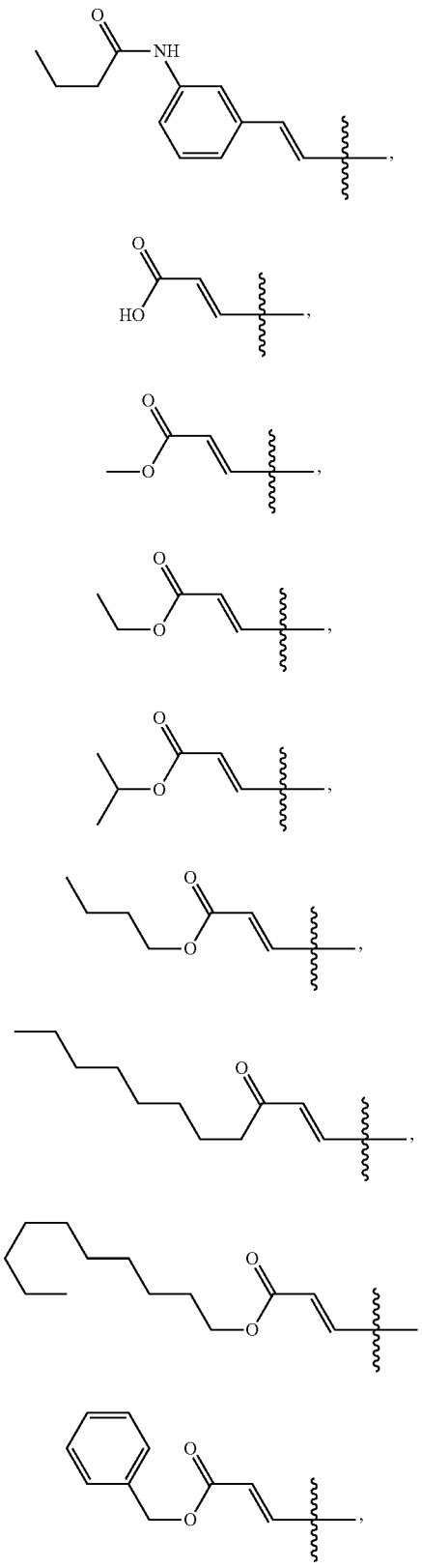
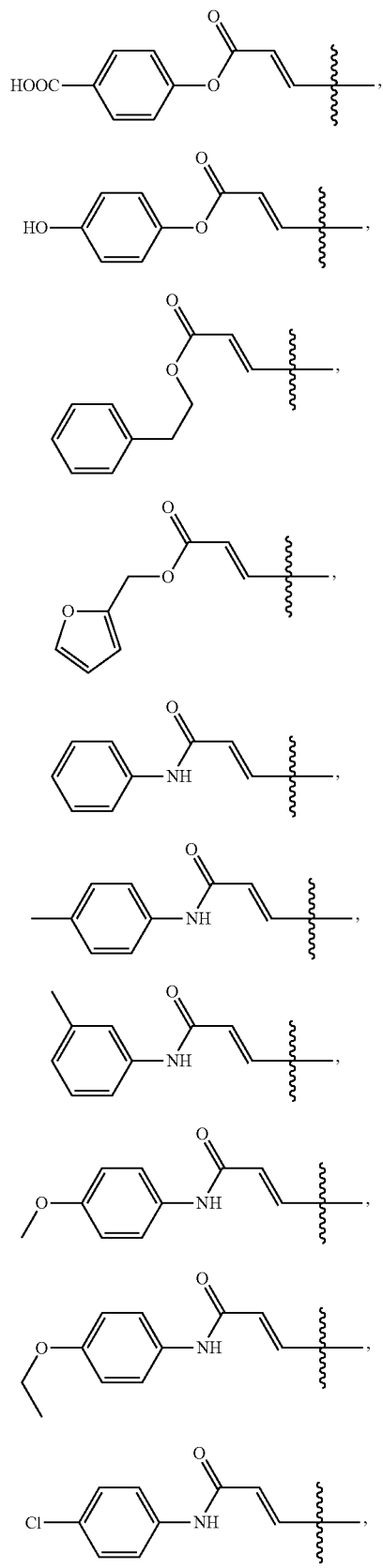

TABLE 1-continued
Formula IV, R1 Options
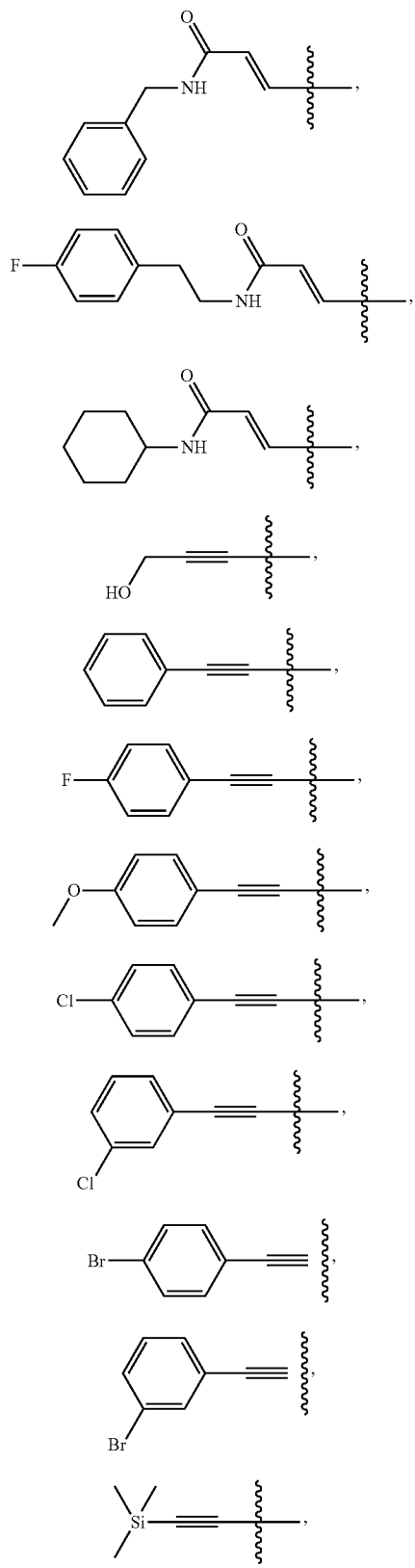
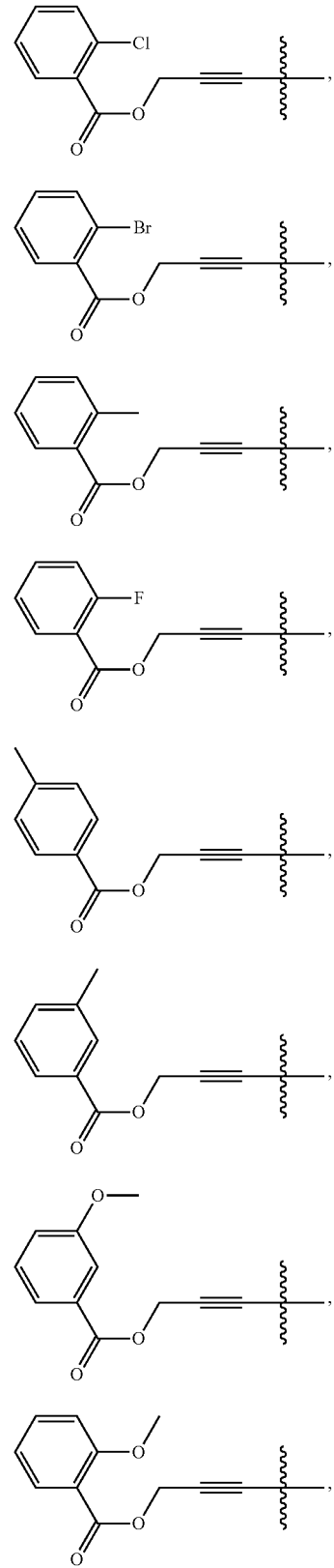

TABLE 1-continued

Formula IV, R1 Options

TABLE 1-continued
Formula IV, R1 Options
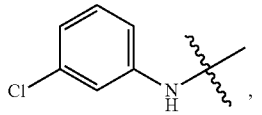 [SMILES: *Nc1cccc(Cl)c1],
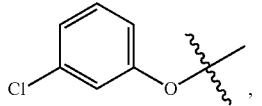 [SMILES: *Oc1cccc(Cl)c1],
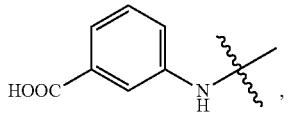,
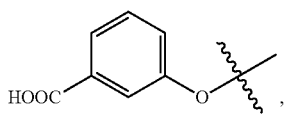 [SMILES: *Oc1cccc(C(=O)O)c1],
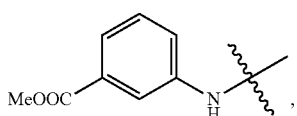,
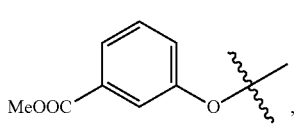 [SMILES: *Oc1cccc(C(=O)OC)c1],
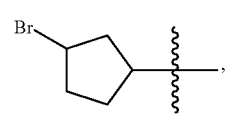,
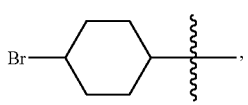,
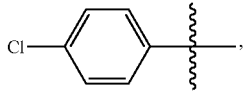,
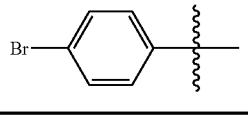,
TABLE 2
Formula IV, R2 Options
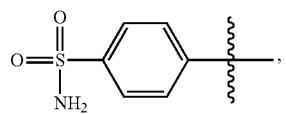 [SMILES: *c1ccc(S(N)(=O)=O)cc1],
TABLE 2-continued
Formula IV, R2 Options
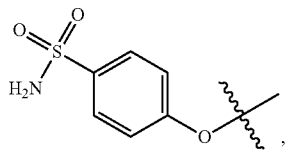,
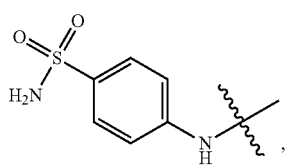 [SMILES: *Nc1ccc(S(N)(=O)=O)cc1],
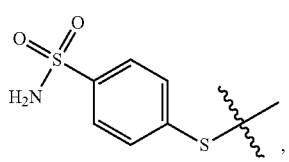,
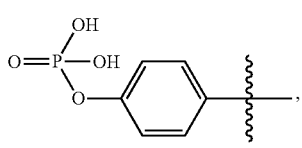 [SMILES: *c1ccc(OP(=O)(O)O)cc1],
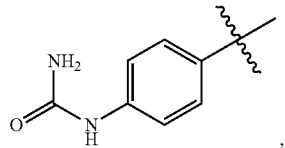 [SMILES: *c1ccc(NC(N)=O)cc1],
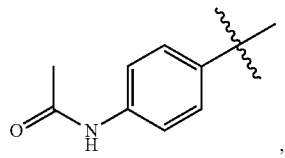 [SMILES: *c1ccc(NC(C)=O)cc1],
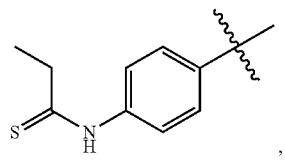 [SMILES: *c1ccc(NC(=S)CC)cc1],
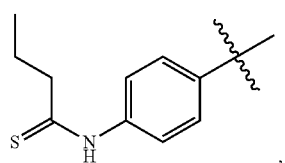 [SMILES: *c1ccc(NC(=S)CCC)cc1],
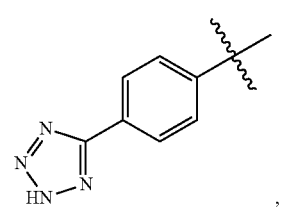 [SMILES: *c1ccc(-c2nn[nH]n2)cc1], TABLE 2-continued
Formula IV, R2 Options
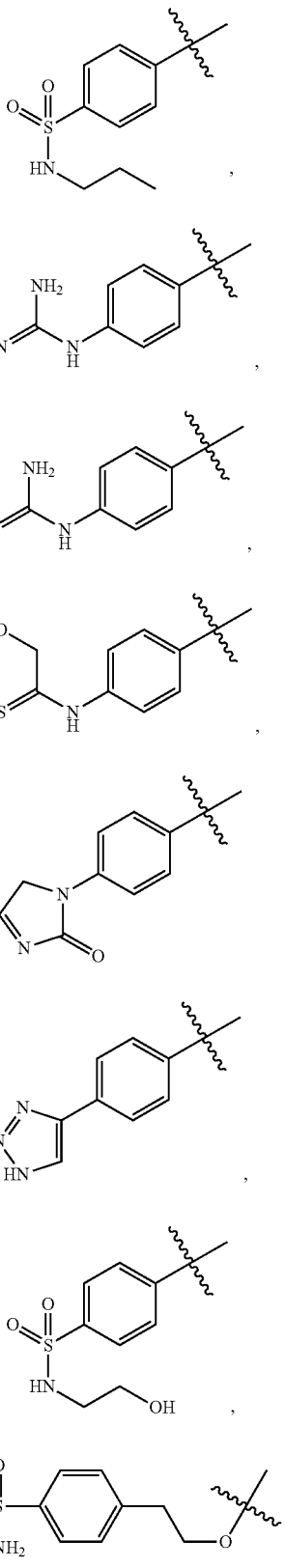
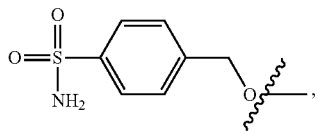
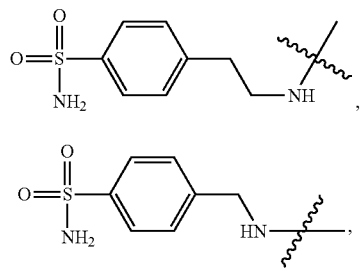
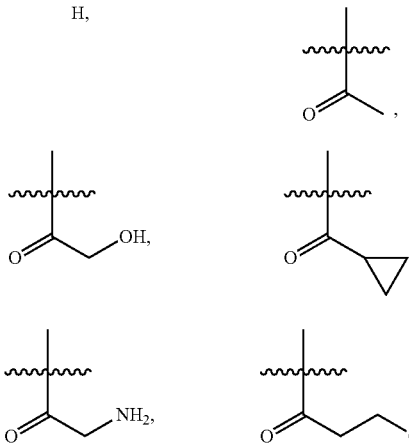
TABLE 3
Formula IV, R3 Options

TABLE 3-continued

Formula IV, R3 Options

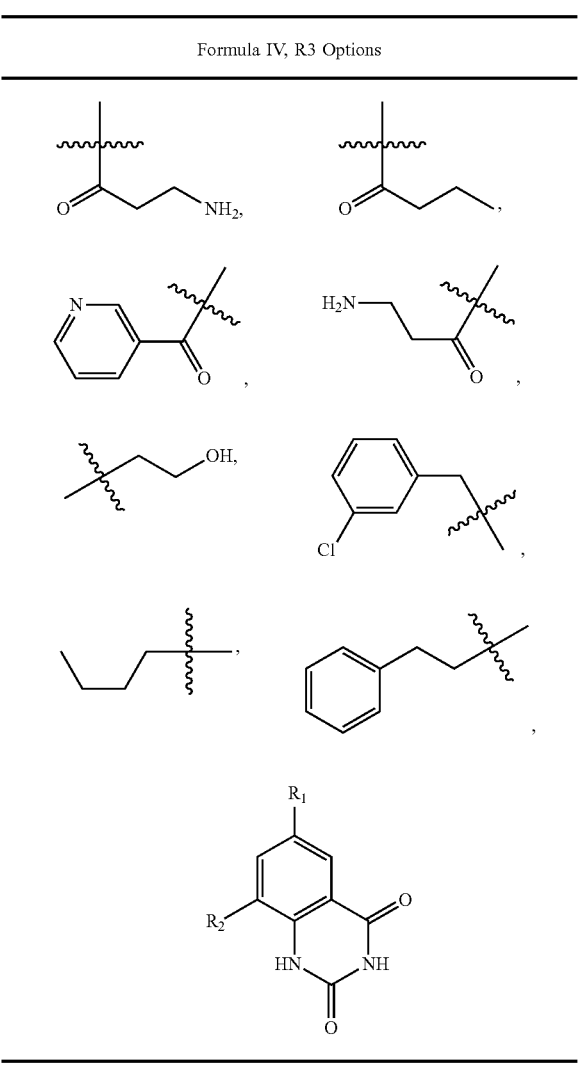

TABLE 4

Formula IV, R4 Options

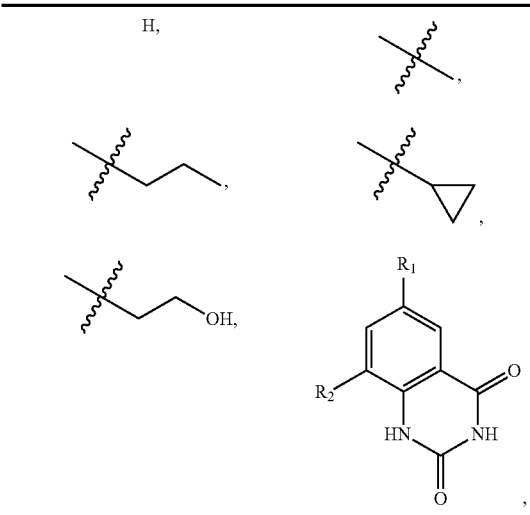

TABLE 4-continued

Formula IV, R4 Options

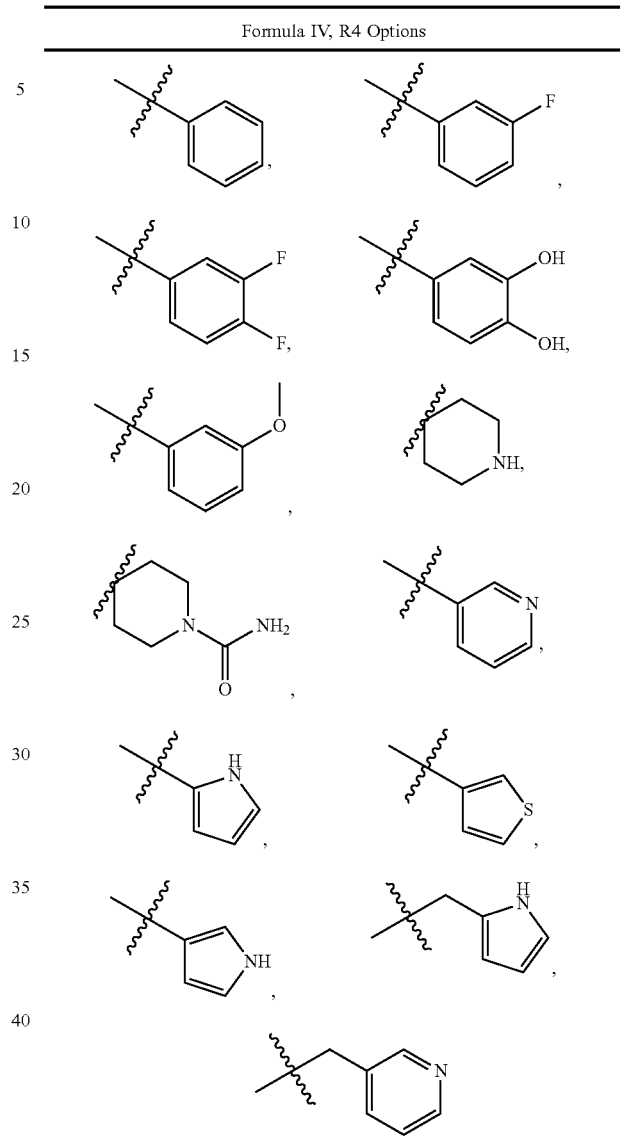

In various embodiments, Formula IV of the invention refers to a chemical compound having the structure shown above, wherein the structure does not include Formula II or alternatively, does not include Formula I.

Preferred embodiments of Formula III are referred to herein as HPN-01101-01133; HPN-01201-01224; HPN-01301-01322; HPN-01401-01430; HPN-01501-01506; HPN-01513-01520; HPN-01525-01527; HPN-01529-01534; HPN-01601-01630 as described below in the Examples. Methods of making compounds of Formula III are illustrated herein and based on the teaching herein are within the skill of the art. Also within the scope of the invention is the use of prodrugs, therapeutically active metabolites, hydrates, solvates, and pharmaceutically acceptable salts of compounds of Formula III.

Compounds of the invention also include stereoisomers, enantiomers, or diastereomers of compounds of Formula I, Formula II, Formula III and Formula IV.

Compounds used in methods of the invention can be formulated in a composition comprising a carrier. "Carriers" as used herein include pharmaceutically acceptable carriers, excipients, or stabilizers which are nontoxic to the cell or mammal being exposed thereto at the dosages and concentrations employed. A "pharmaceutically acceptable carrier" is an excipient that does not interfere with the effectiveness of the biological activity of a compound of the invention. Often the physiologically acceptable carrier is an aqueous pH buffered solution. Examples of physiologically acceptable carriers include buffers such as phosphate, citrate, and other organic acids, Hanks' solution, Ringer's solution, or physiological saline buffer; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

Additional agents, such as flavoring, coloring, sweetening, and/or thickening agents, may be added to compositions of the invention.

Compositions of the invention can be formulated in any suitable form, and, in large part, the form may be determined by the intended mode of administration. Compositions can be in the form of a solid, semi-solid or liquid. Examples of forms useful for practicing methods of the invention include, but are not limited to, tablets, capsules, powders, troches, lozenges, suspensions, gels, pastes, slurries, liquid compositions soft-gel capsules, and syrups. Preferably the compositions are produced in a unit dosage form suitable for administration of a precise dose.

The dose administered to a subject in a method of the invention can be any dose suitable for treating, preventing, inhibiting, and/or reducing NAFLD or a related condition. In conjunction with the present disclosure, those skilled in the art are capable of identifying a dose appropriate for the chosen formulation and method of delivery. In certain embodiments, the dose is in a range of between 0.01 mg/kg to about 100 mg/kg.

Compounds and compositions of the invention can be administered by any route suitable for the subject being treated. Such routes of administration include, but are not limited to, injection, including intravenous, intraperitoneal, intramuscular, and subcutaneous injection, oral administration, transmucosal administration, transdermal administration, topical administration, nasal administration, ocular administration, or via suppository.

One embodiment of the present invention is a method of treating non-alcoholic fatty liver disease (NAFLD) in a subject, the method comprising administering to the subject a therapeutically effective amount of a compound of Formula I, Formula II, Formula III, Formula IV, or a prodrug, therapeutically active metabolite, hydrate, solvate, or pharmaceutically acceptable salt thereof. In certain embodiments, the subject is at risk for developing NAFLD. In certain embodiments, the subject exhibits a form of NAFLD comprising fatty deposit-related inflammation, non-alcoholic steatohepatitis (NASH), liver fibrosis, cirrhosis, or combinations thereof.

In certain embodiments, the compound is administered as a composition comprising a pharmaceutically acceptable carrier. In certain embodiments, the compound is administered once in a 24-hour period. In certain embodiments, the compound is administered more than once in a 24-hour period. In certain embodiments, the compound is administered every 1 hour, every 2 hours, every 3 hours, every four hours, every 6 hours, or every 12 hours. In certain embodiments, the compound is administered continuously.

A further embodiment of the invention is a compound of Formula I, Formula II, Formula III, Formula IV, or a prodrug, therapeutically active metabolite, hydrate, solvate, or pharmaceutically acceptable salt thereof for use in treating nonalcoholic fatty liver disease (NAFLD) in a subject.

One embodiment of the invention is a kit for treating NAFLD, or a related condition, such as, fatty deposit-related inflammation, non-alcoholic steatohepatitis (NASH), liver fibrosis, cirrhosis, or combinations thereof, the kit comprising a compound of Formula I, Formula II, Formula III, Formula IV, or a prodrug, therapeutically active metabolite, hydrate, solvate, or pharmaceutically acceptable salt thereof, and instructions for administering the compound to a subject having, or at risk for, NAFLD, or a related condition, such as, fatty deposit-related inflammation, non-alcoholic steatohepatitis (NASH), liver fibrosis, cirrhosis, or combinations thereof, wherein the formulation of the compound, derivative thereof, or salt thereof, is suitable for administration to a subject for administration to a subject having NAFLD, or a related condition, such as, fatty deposit-related inflammation, non-alcoholic steatohepatitis (NASH), liver fibrosis, cirrhosis, or combinations thereof.

Other embodiments of the invention include a compound of Formula I, Formula II, Formula III, Formula IV, or a prodrug, therapeutically active metabolite, hydrate, solvate, or pharmaceutically acceptable salt thereof. Alternatively, the invention includes a compound of Formula III, Formula IV, or a prodrug, therapeutically active metabolite, hydrate, solvate, or pharmaceutically acceptable salt thereof, wherein the compound is not Formula II and alternatively, is not Formula I. Further embodiments include pharmaceutical compositions comprising a compound of Formula I, Formula II, Formula III, Formula IV or a prodrug, therapeutically active metabolite, hydrate, solvate, or pharmaceutically acceptable salt thereof and a pharmaceutically acceptable carrier. Alternatively, the invention includes a pharmaceutical composition comprising a compound of Formula III, Formula IV, or a prodrug, therapeutically active metabolite, hydrate, solvate, or pharmaceutically acceptable salt thereof, wherein the compound is not Formula II and alternatively, is not Formula I.

Still further embodiments of the invention include methods of making the compounds of the invention as described below in the Examples. Such methods include for example, synthesis of Compound II (Formula II) as described in Example 1; as well as synthesis of HPN-01101-HPN-01133 as described in Example 18; synthesis of HPN-01201-HPN-01224 as described in Example 19; synthesis of HPN-01301-HPN-01311 and HPN-01321-HPN-01322 as described in Example 20; synthesis of HPN-01312-HPN-01320 as described in Example 21; synthesis of HPN-01401-HPN-01430 as described in Example 22; synthesis of HPN-01501-HPN-01506; HPN-01513-HPN-01520; HPN-01525-HPN-01527; HPN-01529-HPN-01534 as described in Example 23; and synthesis of HPN-01602-HPN-01630 as described in Example 24.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

The invention is illustrated by the following non-limiting examples. One of ordinary skill in the art will appreciate that a powder X-ray diffraction pattern may be obtained with a measurement error that is dependent upon the measurement conditions employed. In particular, it is generally known that intensities in an X-ray powder diffraction pattern may fluctuate depending upon measurement conditions employed. It should be further understood that relative intensities may also vary depending upon experimental conditions and, accordingly, the exact order of intensity should not be taken into account. Accordingly, the relative intensity of peaks in a diffractogram is not necessarily a limitation of the PXRD pattern because peak intensity can vary from sample to sample, e.g., due to crystalline impurities. Additionally, a measurement error of diffraction angle for a conventional powder X-ray powder diffraction pattern is typically about 5% or less, and such degree of measurement error should be taken into account as pertaining to the aforementioned diffraction angles. Further, the angles of each peak can vary by about +/−0.1 degrees, or by about +/−0.05. The entire pattern or most of the pattern peaks may also shift by about +/−0.1 degrees to about +/−0.2 degrees due to differences in calibration, settings, and other variations from instrument to instrument and from operator to operator. All reported PXRD peaks in the Figures, Examples, and elsewhere herein are reported with an error of about ±0.3 degrees 2-theta. Unless otherwise noted, all diffractograms are obtained at about room temperature (about 24° C. to about 25° C.). It is to be understood that the crystal structures of the instant invention are not limited to the crystal structures that provide X-ray diffraction patterns completely identical to the X-ray powder diffraction patterns depicted in the accompanying Figures disclosed herein. Any crystal structures that provide powder X-ray diffraction patterns substantially identical to those disclosed in the accompanying Figures fall within the scope of the present invention. The ability to ascertain substantial identities of X-ray powder diffraction patterns is within the purview of one of ordinary skill in the art. One of skill in the art will however, note that in DSC [or TGA] measurement there is a certain degree of variability in actual measured onset and peak temperatures, depending on rate of heating, crystal shape and purity, sample preparation and other measurement parameters.

EXAMPLES

Example 1. Identification and Synthesis of Inhibitors of Steatosis

Figure 2:
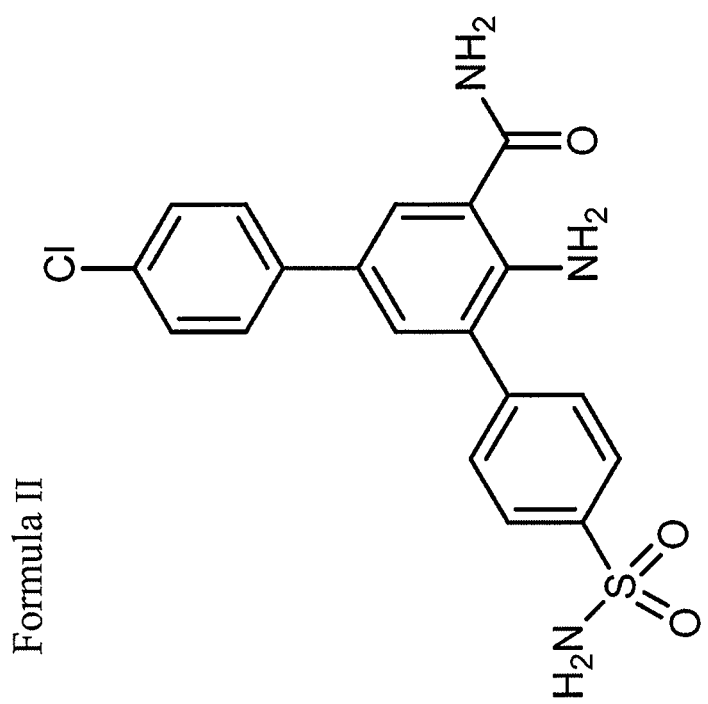
FIG. 2. Formula II. Structure of HPN-01.

High-throughput screening of small molecule libraries was conducted against hepatocytes to identify compounds possessing potent anti-steatosis activities. This screening led to the identification of a compound named HPN-01. HPN-01 (chemical formula: $C_{19}H_{16}ClN_3O_3S$), is a 2-amino-3,5-diarylbenzamide (CAS: 928655-63-4), the general structure of which is shown in FIG. 1. The specific structure of HPN-01 (referred to herein as Compound II) is shown in FIG. 2. Compound II is 2-amino-3-(p-sulfonamidophenyl)-5-(p-chlorophenyl) benzamide.

Compound II was prepared using the following protocol:

1. 1500 g of starting material 2-amino-5-iodobenzoic acid was first dissolved in 2 L of DMF in the reactor at room temperature, and 3733 g of triphosgene was added in batches and stirred for 2-2.5 h with increasing temperature. The reaction was monitored by HPLC until finish. 8500 mL of ammonia was dropwise added under controlled temperature at 35-40° C. The reaction was continued for additional 0.5-1 h at the same temperature with stirring after ammonia addition and then concentrated under reduced pressure when the reaction was complete as measured by HPLC. The residue was dropped into 20 L of water and stirred for 2-3 h before letting it stand, followed by filtering, washing and drying. 1275 g of 2-amino-5-iodobenzamide was obtained from the above reactions with 85% overall yield. The purity was 99.6% as measured by HPLC.

2. Successively adding 600 g of 2-amino-5-iodobenzamide, 6000 mL of Dioxane, 2400 mL of water, 600 g of Potassium carbonate, 393 g of P-chlorobenzene boronic acid, and 6 g of PdCl2(PPh3)2 to the reactor, and heated at 85-87° C. under reflux for 4-5 h. PdCl2(PPh3)2 was recovered by filtering. The upper aqueous layer was discarded, and the organic layer was concentrated under reduced pressure. The residue was dropped into 20 L of water, adjusting the pH to 7 using dilute hydrochloric acid under continuously stirring. After filtering, washing and drying, the crude product was obtained, which was added to the mixed solvent of anhydrous ethanol and tetrahydrofuran (2:1, v/v), heated to reflux, dropped same volume of isopropyl ether followed by stirring, filtering, washing by isopropyl ether, and then drying to yield 601 g of 2-amino-5-(p-chlorophenyl) benzamide. The purity was 96.21% as measured by HPLC.

3. 258.2 g of 2-amino-5-(p-chlorophenyl) benzamide, 200 mL of acetic acid and 1100 mL of dichloromethane were added to the reactor. At controlled temperature of 15-20° C., adding 222.9 g of NBS in batches and stirring at room temperature for 1-2 h. Subsequent filtering, washing with methylene chloride and potassium carbonate solution, washing with water, and then drying yielded 232.0 g of 2-amino-3-bromo-5-(p-chlorophenyl) benzamide with a 90% overall yield. The purity was 95.4% as measured by HPLC.

4. 2700 g of potassium acetate, 2250 g of boronic acid, 11 g of PdCl2(dppf)2, 2000 g of P-bromobenzenesulfonamide, and 13500 mL of dioxane were added to the reactor, stirred and heated to 85-87° C. and reacted for 4-5 h. PdCl2(dppf)2 was recovered by filtration. The filtrate was concentrated under reduced pressure, and 6000 mL of isopropyl ether was then added and stirred for 1-2 h, followed by filtering, isopropyl ether washing and drying. 116 g of P-sulfonamide phenylboronic acid pinacol ester was obtained from the reaction with a 64.8% overall yield. The purity was 96.8% as measured by HPLC.

5. Successively adding 500 g of 2-amino-3-bromo-5-(p-chlorophenyl) benzamide, 480 g of P-sulfonamide phenylboronic acid pinacol ester, 425 g of potassium carbonate, 6 g of PdCl2(PPh3)2, 3000 mL of dioxane, and 1200 mL of water to the reactor successively and heating to 85-87° C. under reflux for 3-4 h until the reaction was complete. Triphenylphosphine dichloride palladium was recovered by filtering, and the upper aqueous layer was discarded. 2000 mL of ethyl alcohol was added to the concentrated organic layer and refluxed with stirring for 1 h, followed by filtering, ethanol rinsing and drying. 757 g of 2-amino-3-(p-sulfonamidophenyl)-5-(p-chlorophenyl) benzamide was obtained from the reaction. The purity was 82.6%.

6. Purification of HPN-01. 1000 g of 2-amino-3-(p-sulfonamidophenyl)-5-(p-chlorophenyl) benzamide crude product and 20 L of acetone were added into the refined kettle, stirred, and heated to reflux. The insoluble was filtered off, and the filtrate was reflux decolorized with activated carbon for 0.5 h. The activated carbon was then filtered off, and the filtrate was concentrated under reduced pressure to slightly cloudy, and subsequently 4-6 L of water was dropped in under stirring at 50-60° C. Crystal precipitation was obtained by stirring at room temperature, filtered, washed by acetone:water (1:1) mixed solvent, and then dried. 880 grams of HPN-01 was obtained with an 88% overall yield. The purity was 99.2% as measure by HPLC.

Example 2. Effect of HPN-01 Treatment on Hepatocellular Lipid Droplet (LD) Biogenesis Hepatoma cell line Huh7 cells were treated with various amounts of HPN-01 for 24 h, either in the absence or in the presence of 400 µM oleic acid, and observed under a Zeiss confocal microscope. The results of this analysis, which are shown in FIGS. 5A-D, showed that HPN-01 treatment significantly suppressed LD formation in Huh7 cells in a dose-dependent manner ($IC_{50}$=0.46 µM without oleic acid pre-treatment, and 0.27 µM with oleic acid stimulation). LD contents (stained with BODIPY 493/503, in green) were observed under a Zeiss confocal microscope. FIG. 5A. Blue indicates cell nuclei. FIG. 5B. LD size. FIG. 5C. Mean fluorescence intensity. Values were measured using ZEN software by counting 300 cells under each treatment condition.

Example 3. Effect of HPN-01 Treatment on LD Formation in Hepatocytes

Figure 6:
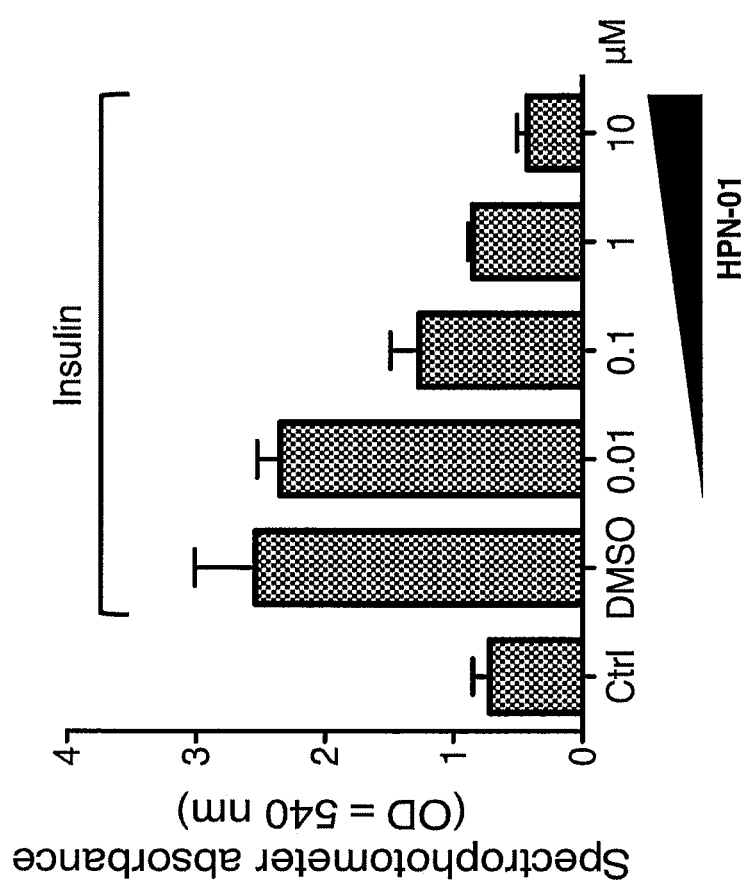
FIG. 6. Inhibitory effect of HPN-01 treatment on LD biogenesis in cultured hepatocytes ($IC_{50}$=0.25 μM). Spectrophotometric absorbance of untreated or HPN-01-treated Huh7 cells pre-incubated with 1 mM insulin is shown. LD contents were stained using Oil Red O, and measured by determining spectrophotometer absorbance under OD 540 nm.

Huh7 cells were mock treated or pre-treated with 1 mM insulin, and subsequently treated with indicated amounted of HPN-01. After 24 h, LD contents were stained using Oil-Red-O, and measured by determining spectrophotometer absorbance under OD 540 nm ($IC_{50}$=0.25 µM). The results of these analyses are shown in FIG. 6. The results demonstrate that HPN-01 inhibited LD formation in hepatocytes in a dose-dependent manner.

Figure 7:
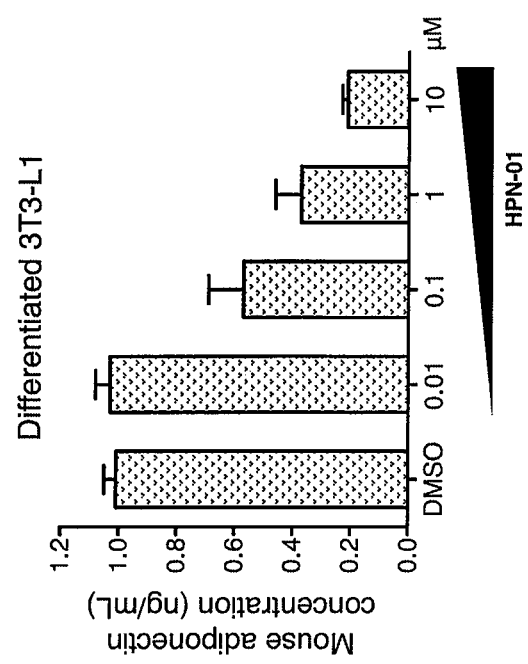
FIG. 7. Effect of HPN-01 treatment on secreted mouse adiponectin levels in differentiated 3T3-L1 cells ($IC_{50}$=0.32 μM).

Example 4. Effect of HPN-01 Treatment on Adiponectin Levels in Mouse 3T3-L1 Cells Differentiated, mouse 3T3-L1 cells were treated with varying concentrations of HPN-01, and the level of secreted adiponectin measured by ELISA. The results, which are shown in FIG. 7, demonstrate that HPN-01 decreased the amount of secreted adiponectin in hepatocytes in a dose-dependent manner ($IC_{50}$=0.32 µM).

Example 5. Effect of HPN-01 on De Novo Lipogenesis in Hepatocytes

Figure 8:
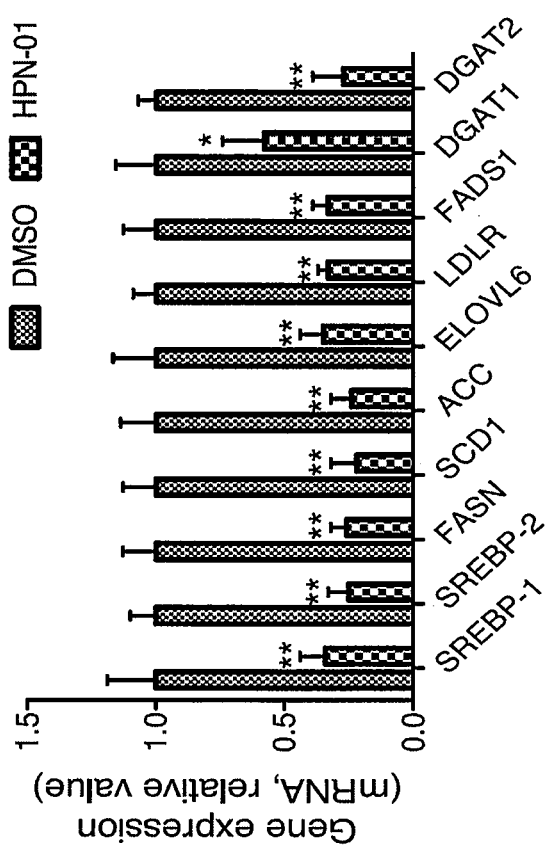
FIG. 8. Inhibition of various lipogenic gene mRNA levels following treatment with HPN-01. The graph shows the relative level of mRNA from cells treated with DMSO (represented as 1.0, grey hatching) or HPN-01 (black/white hatching). Sterol regulatory element-binding protein-1 (SREBP-1); Sterol regulatory element-binding protein-2 (SREBP-2); Fatty acid synthase (FASN); Stearoyl-CoA-desaturase (SCD1); Acetyl-CoA carboxylase (ACC); Elongation of very long chain fatty acids fatty acid elongase 6 (ELOVL6); Low density liporeceptor (LDLR); Fatty acid desaturase 1 (FADS1); Diacylglycerol 0-Acyltransferase 1 (DGAT1); Diacylglycerol O-Acyltransferase 2 (DGAT2).

Huh7 cells were treated with 1 µM of HPN-01 for 24 h, and the mRNA expression levels of various pivotal lipogenic enzymes were quantified by real-time qPCR. The results, which are shown in FIG. 8, demonstrate that HPN-01 treatment significantly suppressed de novo lipogenesis in hepatocytes. Folds of inhibition were as follows: SREBP-1: 2.98±0.23; SREBP-2: 4.01±0.31; FASN: 3.87±0.23; SCD1: 4.63±0.48; ACC: 4.12±0.34; ELOVL6: 2.84±0.22; LDLR: 3.02±0.11; FADS1: 3.06±0.17; DGAT1: 1.72±0.27; DGAT2: 3.77±0.45.

Figure 9:
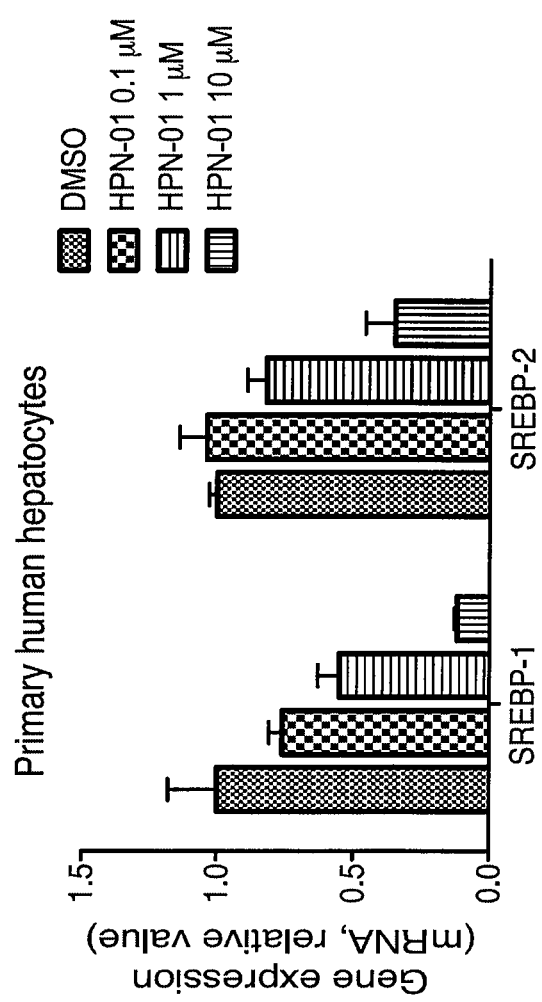
FIG. 9. Effects of HPN-01 on the expression of SREBP-1 (master regulator of hepatic glucose metabolism and fatty acid synthesis) and SREBP-2 (master regulator of cholesterol homeostasis in cells) in cultured primary human hepatocytes. $IC_{50}$=1.71 μM (SREBP-1) and 3.43 μM (SREBP-2).

Example 6. Effects of HPN-01 on Expression of SREBP-1 and SREBP-2 in Primary Human Hepatocytes Cultured primary human hepatocytes were treated with various concentrations of HPN-01, and the expression levels of SREBP-1 (master regulator of hepatic glucose metabolism and fatty acid synthesis) and SREBP-2 (master regulator of cholesterol homeostasis in cells) were subsequently determined. The results of this analysis are shown in FIG. 9. The results demonstrate that HPN-01 treatment reduces the expression of SREBP-1 and SREBP-2 in a dose-dependent manner ($IC_{50}$=1.71 µM and 3.43 µM, respectively).

Example 7. Cytotoxicity of HPN-01

Figures 10A, 10B:
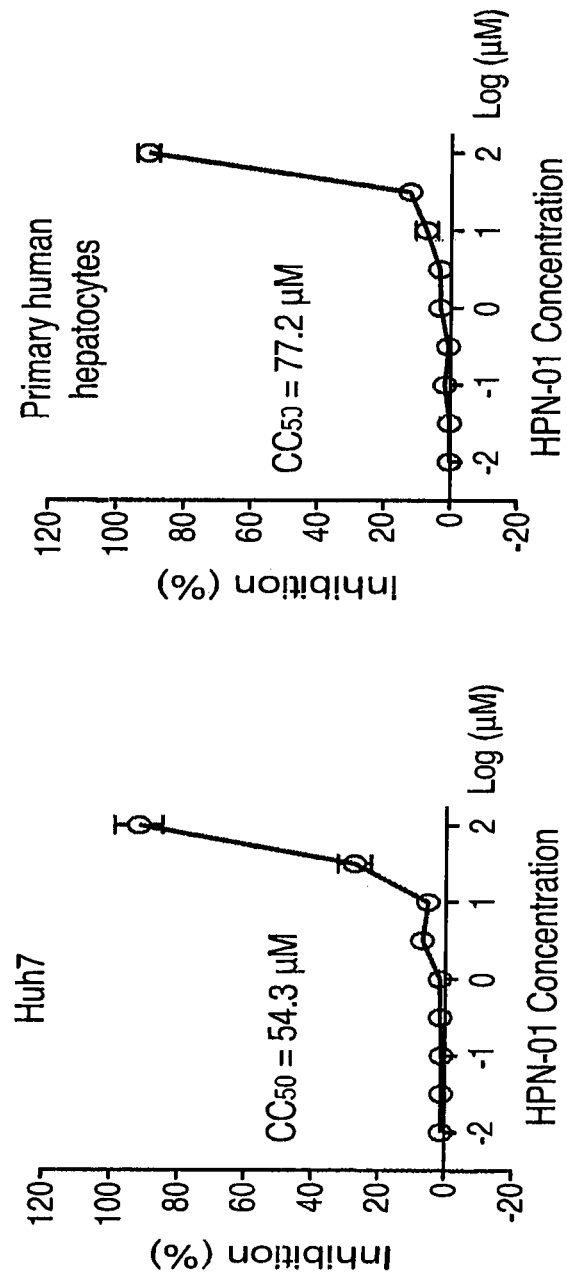
FIGS. 10A and 10B. Inhibition of hepatocyte growth by HPN-01. $CC_{50}$=54.3 μM (Huh7 cells, FIG. 10A) and 77.2 μM (primary human hepatocytes, FIG. 10B).

Huh7 cells and primary human hepatocytes were cultured in the presence of varying concentrations of HPN-01, and the inhibition of cell growth was measured. The results of this analysis, which are shown in FIGS. 10A and 10B, show that the cytotoxic concentration that will kill half of the treated cells (CC50) was 54.3 µM for Huh7 cells (FIG. 10A) and 77.2 µM for primary human hepatocytes (FIG. 10B).

Example 8. Effect of HPN-01 on High Fat Diet-Induced NAFLD/NASH Mice

Figure 11:
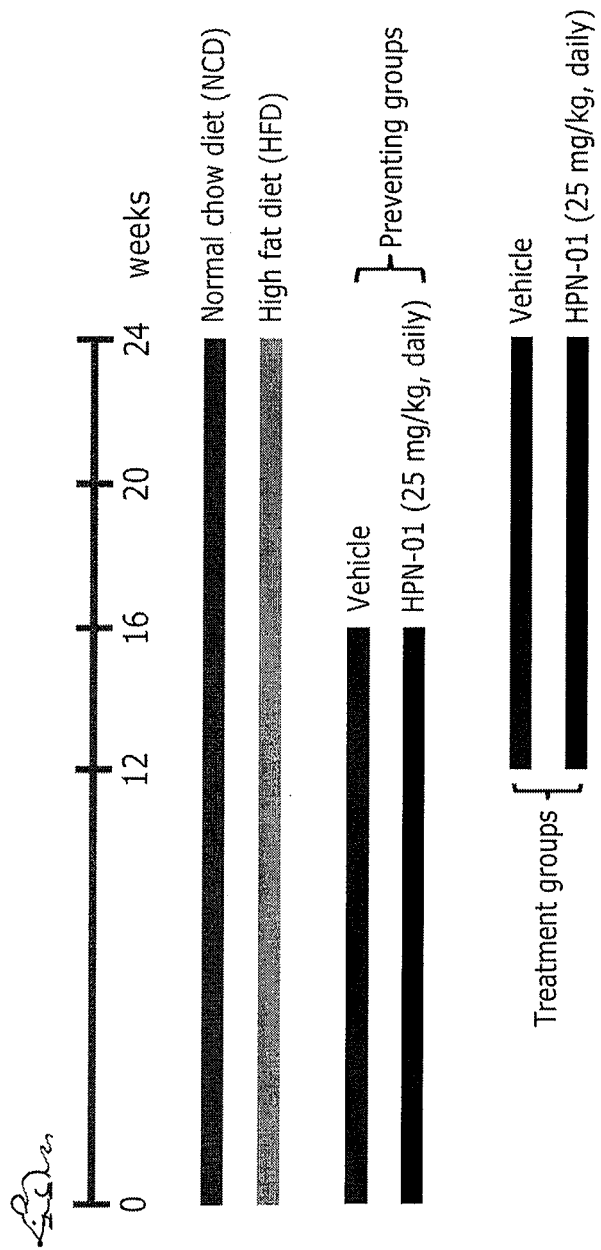
FIG. 11. Study design of in vivo HPN-01 effects on high fat diet-induced NAFLD/NASH mice.

Eight-week old C57BL/6 mice were divided into a test group and a control group. The control group mice were fed with normal chow diet (NCD) for 24 weeks. The test group was further divided into a preventing group and a treatment group. In the preventing group, mice were fed with high-fat diet (HFD) and simultaneously treated with 25 mg/kg of HPN-01 or vehicle daily for 16 weeks, after which time the mice were euthanized and evaluated for NAFLD/NASH development. In the treatment group, mice were fed with HFD for 12 weeks to stimulate the development of NAFLD/NASH, and then treated with 25 mg/kg of HPN-01 or vehicle daily for additional 12 weeks. The mice were then euthanized and evaluated for the presence of NAFLD/NASH. This study design is illustrated in FIG. 11.

Figure 12B:
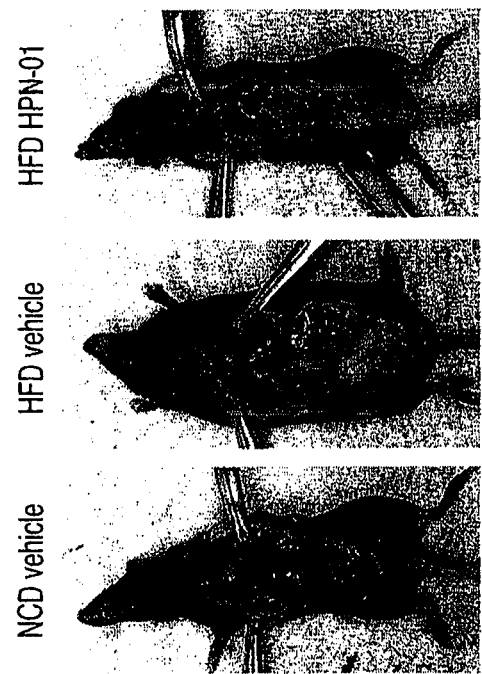
FIGS. 12A and 12B. Effects of HPN-01 treatment on obesity and visceral fat accumulation in mice.
Figure 12A:
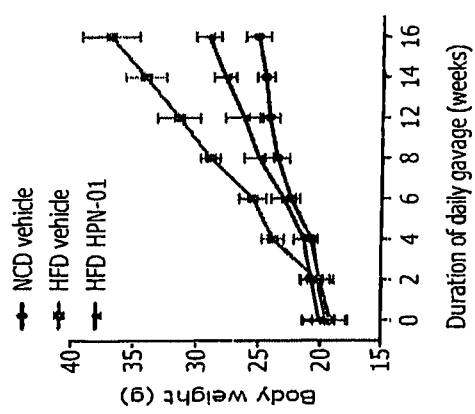

The result of this study shows that HFD triggered obesity (FIG. 12A) and visceral fat accumulation (FIG. 12B, middle panel) in untreated mice. In addition, untreated mice fed a HFD had an enlarged liver, dark orange in color, which are characteristics of NAFLD/NASH (FIG. 12B, middle panel). In contrast, in HFD-fed mice receiving HPN-01 treatment, the body weight increase (FIG. 12A) and fat deposition (FIG. 12C, right panel) were significantly remitted. The size and color of liver (FIG. 12B, right panel) were very similar to the control mice (FIG. 12B, left panel).

Figure 13A:
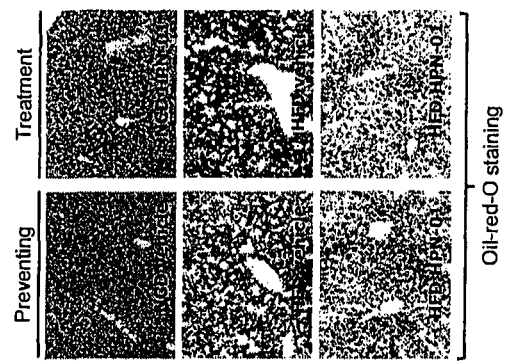
FIGS. 13A and 13B. Effect of HPN-01 treatment on HFD-induced hepatic steatosis. Mice were fed according to the study outline shown in FIG. 11. Mice were then euthanized and section of liver subject to microscopic evaluation.
Figure 13B:
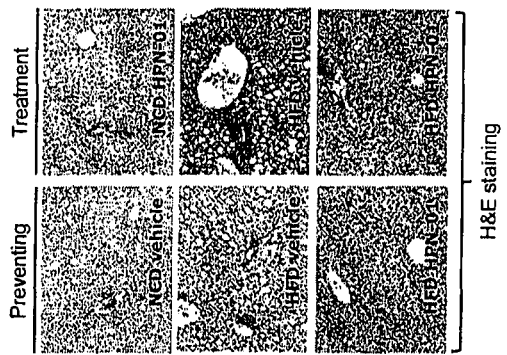

Sections of liver were then analysed for the presence of liver disease. Haematoxylin and eosin (H&E) staining of liver tissue sections (FIG. 13A) showed that there were substantial amounts of vacuole (LD) deposition and obvious inflammatory cells infiltration in HFD-fed mice in the vehicle treatment group. However, in both preventing and treatment groups, LD deposition and inflammatory infiltration were substantially diminished, suggesting that HPN-01 treatment significantly reversed the HFD-mediated hepatic steatosis. The H&E staining results were confirmed by Oil-red-O staining of liver tissue sections (FIG. 13B).

Figure 14A:
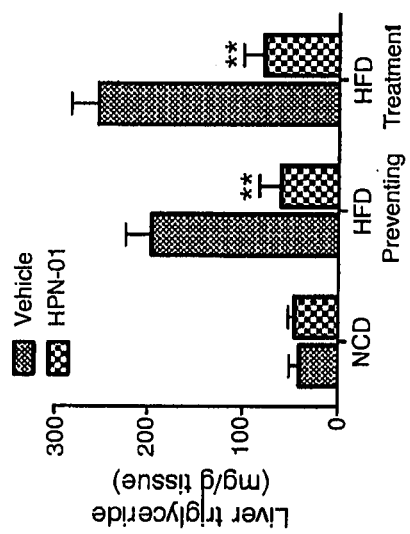
FIGS. 14A and 14B. Effect of HPN-01 treatment on HFD-induced liver triglyceride (FIG. 14A) and glycogen (FIG. 14B) levels.
Figure 14B:
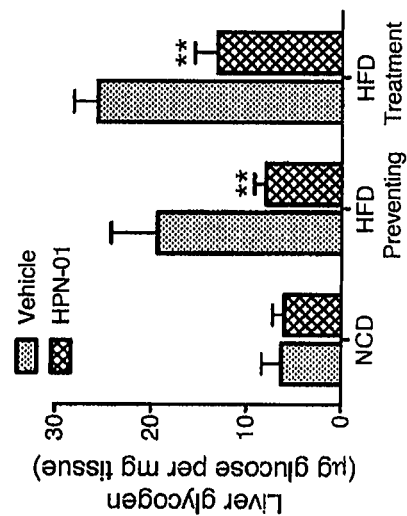

Example 9. Effects of HPN-01 on Hepatic Triglycerides, Glycogen and Cholesterol Levels To determine the effect of HPN-01 on various fat-related molecules in the liver of mice from the study in Example 8, liver tissues were isolated and prepared and the levels of hepatic triglyceride and glycogen were measured. The results of this analysis are shown in FIGS. 14A and 14B.

A high-fat diet in mice receiving only vehicle induced accumulation of triglycerides (FIG. 14A) and glucose synthesis (FIG. 14B) within hepatocytes. In both preventing group and treatment group, HPN-01 treatment drastically reduced HFD-induced elevation of liver triglyceride (FIG. 14A) and glycogen (FIG. 14B) contents. Triglyceride level was found to be 67.2±28.3 mg/g in HFD-fed mice with HPN-01 treatment in preventing group and 75.5±19.8 mg/g in treatment group, compared with 193.7±32.5 mg/g in HFD-fed mice with vehicle treatment in preventing group and 241.2±27.4 mg/g in treatment group. Glycogen level was found to be 8.4±1.6 µg/mg in HFD-fed mice with HPN-01 treatment in preventing group and 13.3±3.5 µg/mg in treatment group, compared with 19.5±4.9 µg/mg in HFD-fed mice with vehicle treatment in preventing group and 26.0±3.1 µg/mg in treatment group. Thus, HPN-01 treatment drastically reduced HFD-induced elevation of liver triglyceride (FIG. 14A) and glycogen (FIG. 14B) contents, which are the most important indicators of hepatic fat synthesis and glucose metabolism, respectively.

Figures 15A, 15B, 15C:
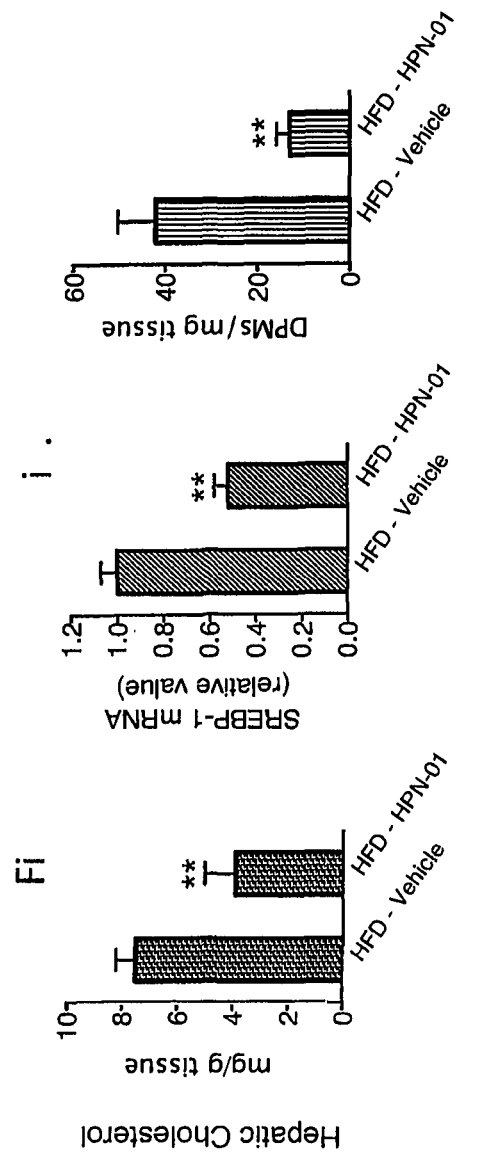
FIGS. 15A-15C. Effects of HPN-01 treatment on HFD-induced hepatic cholesterol, expression of SREBP-1, and fatty acid synthesis. Livers from mice fed according to study outline shown FIG. 11 were examined for the levels of cholesterol (FIG. 15A), SREBP-1 expression (FIG. 15B), and fatty acid synthesis (FIG. 15C).

The livers of mice from the study of Example 8 were also analysed for their levels of cholesterol, SREBP-1, and fatty acid synthesis. This analysis, the results of which are shown in FIGS. 15A-15C, showed that HPN-01 treatment significantly decreased HFD-induced elevation of hepatic cholesterol (FIG. 15A), SREBP-1 (FIG. 15B) and fatty acid synthesis (FIG. 15C). The hepatic cholesterol level in HFD-fed mice with HPN-01 treatment was 3.9±1.1 mg per g tissue, compared with 7.5±0.7 mg per g tissue in HFD-fed mice receiving only vehicle, a decrease of about 1.92-fold (FIG. 15A). Likewise, SREBP-1 expression in HFD-fed mice with HPN-01 treatment was 0.52±0.06, a reduction of about 48% when compared with HFD-fed mice receiving only vehicle (FIG. 15B). Finally, fatty acid synthesis in HFD-fed mice with HPN-01 treatment was 13.2±2.8 DPMs/mg, compared with 42.0±8.3 DPMs/mg in HFD-fed mice receiving vehicle only, a decrease of about 3.18-fold (FIG. 15C).

Example 10. Effects of HPN-01 on Plasma Cholesterol and Triglyceride Levels

Figures 16A, 16B:
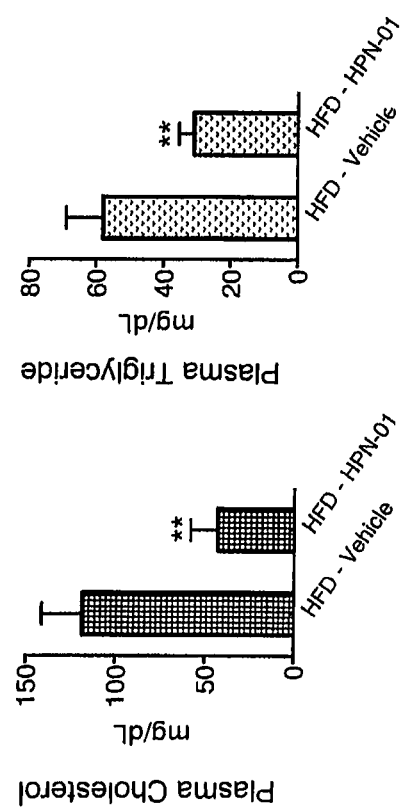
FIGS. 16A and 16B. Effects of HPN-01 treatment on plasma cholesterol and triglyceride levels. Blood was obtained from mice fed according to the study outline shown FIG. 11, and plasma cholesterol and triglyceride levels determined.

Plasma cholesterol and triglyceride levels were determined in blood taken from mice in the study described in Example 8. The results of this analysis are shown in FIGS. 16A and 16B. The results show that HPN-01 treatment considerably abated HFD-mediated elevation of plasma cholesterol (FIG. 16A) and triglyceride (FIG. 16B) levels. Plasma cholesterol levels were 43.0±15.5 mg/dL in HFD-fed mice receiving HPN-01, compared with 118.1±23.3 mg/in vehicle-treated HFD-fed mice receiving only vehicle, a decrease of 2.75-fold. Likewise, plasma triglyceride levels were 31.2±4.5 mg/dL, in HFD-fed mice receiving HPN-01, compared with 58.4±11.7 mg/dL in HFD-fed mice receiving only vehicle, a decrease 1.87-fold, respectively.

Example 11. Effects of HPN-01 on Hepatic Inflammatory Cytokines

Figure 17:
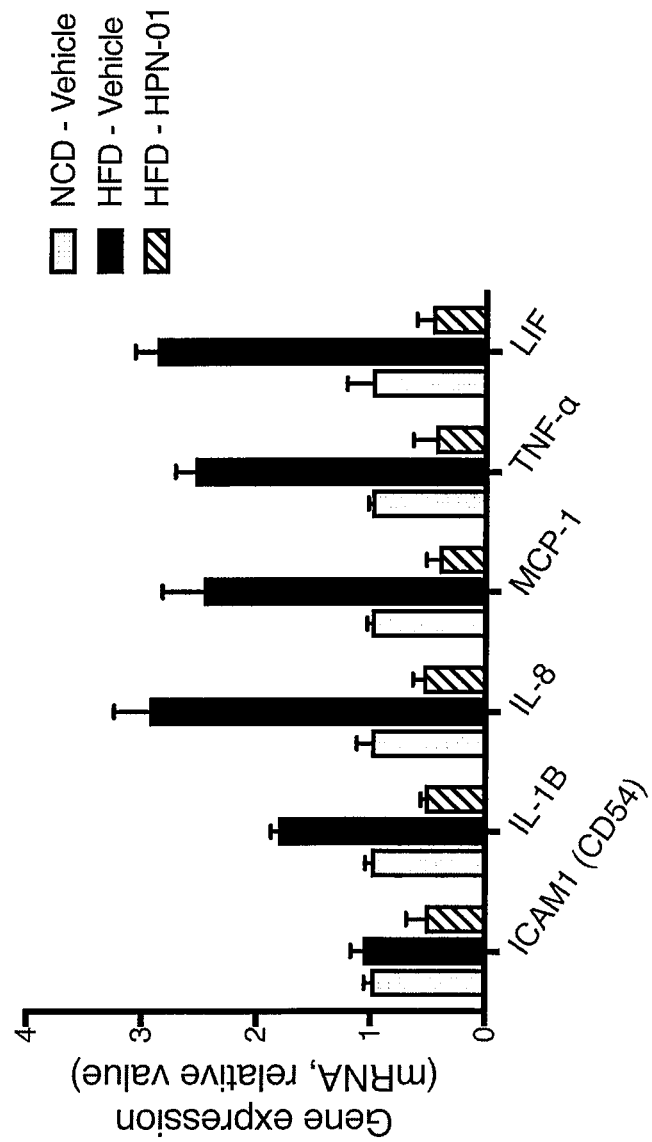
FIG. 17. Effect of HPN-01 treatment on cytokine expression in mouse livers. Livers from mice fed according to study outline shown FIG. 11 were examined for the levels of ICAM1(CD54), IL-1B, IL-8, MCP-1, TNF-α and LIF. Hepatic inflammatory cytokine expression was suppressed by HPN-01 treatment.

Liver tissues from mice in the study of Example 8 were analysed for the expression level of inflammatory cytokines. The results, shown in FIG. 17, demonstrate that hepatic expression of ICAM1(CD54), IL-1B, IL-8, MCP-1, THF-α and LIF were significantly induced by HFD feeding. Further, the results show that this induction was substantially abrogated upon HPN-01 treatment.

Example 12. Effects of HPN-01 on Hepatic Expression of Fibrotic Markers

Figures 18A, 18B:
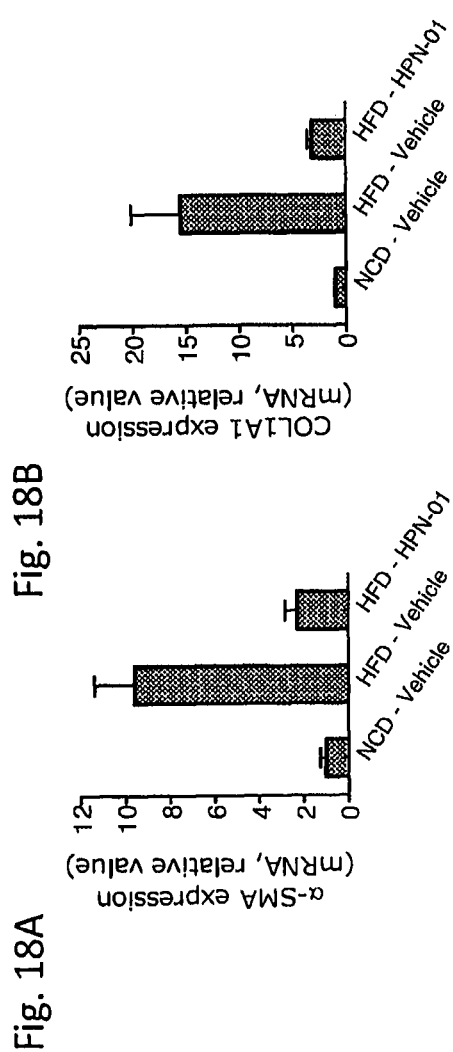
FIGS. 18A and 18B. Effects of HPN-01 treatment on levels of alpha-smooth muscle actin (α-SMA) and collagen type 1 alpha 1 (COL1α1) mRNA expression. Livers from mice fed according to study outline shown FIG. 11 were examined for the expression of α-SMA mRNA and COL1α1 mRNA.

Liver tissues from mice in the study of Example 8 were analysed for the expression levels of hepatic molecules involved in the formation of fibrotic scarring. FIG. 18A shows the mRNA levels of α-smooth muscle actin (α-SMA) in mice fed with normal chow diet (NCD), and in HFD-fed mice receiving vehicle or HPN-01. FIG. 18B shows the mRNA levels of COL1A1 in mice fed with normal chow diet (NCD), and in HFD-fed mice receiving vehicle or HPN-01.

Figure 19:
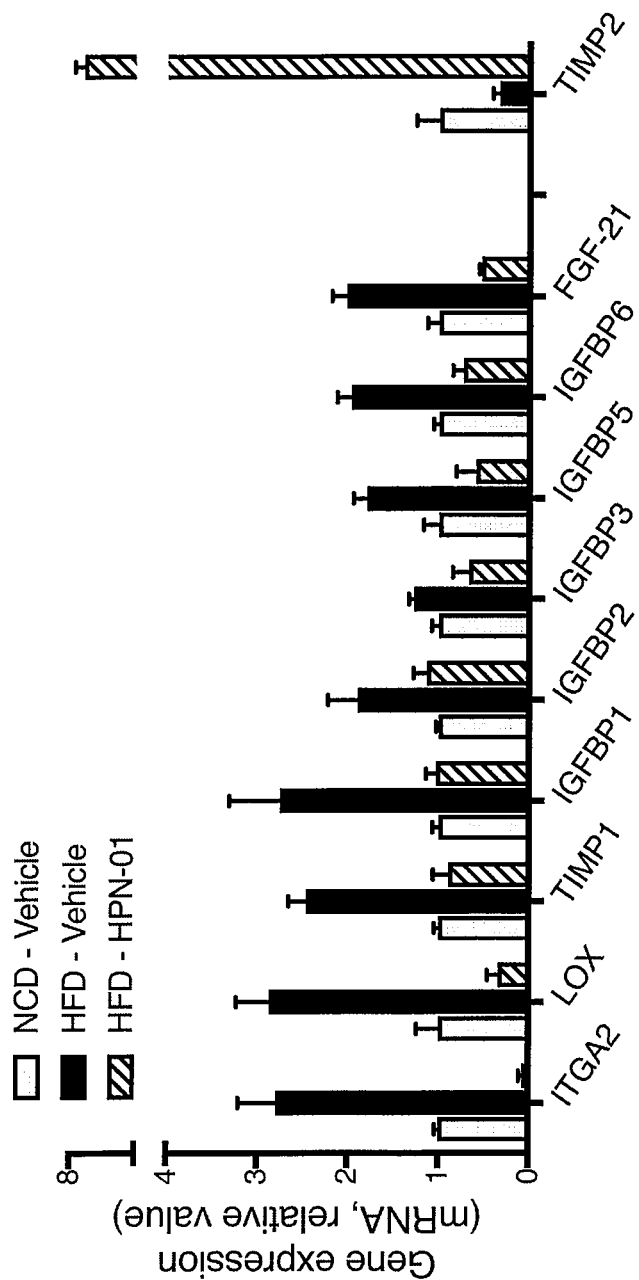
FIG. 19. Effects of HPN-01 treatment on levels of various liver adipokines. Livers from mice fed according to study outline shown FIG. 11 were examined for the mRNA levels of integrin alpha 2 (ITGA2), lectin-like oxidized LDL receptor (LOX), tissue inhibitor of metalloproteinase-1 (TIMP1), insulin-like growth factor binding protein-1 (IGFBP1), insulin-like growth factor binding protein-2 (IGFBP2), insulin-like growth factor binding protein-3 (IGFBP3), insulin-like growth factor binding protein-5 (IGFBP5), insulin-like growth factor binding protein-6 (IGFBP6), and fibroblast growth factor-21 (FGF-21).

Liver tissues were then analysed to determine the levels of various pro-fibrotic cytokines. This analysis, the result of which is shown in FIG. 19, shows that HPN-01 treatment significantly suppressed the induction of ITGA2, LOX, TIMP1, IGFBP1, IGFBP2, IGFBP3, IGFBP5, IGFBP6 and FGF-21 by HFD feeding. The expression level of TIMP2, a fibrosis suppressor, was increased in the presence of HPN-01.

Example 13. HPN-01 Infra-Red Spectrogram

An infra-red spectrogram of HPN-01 was generated using the following instrument and conditions.

Instrument type: Nicolet NEXUS 670 Infrared spectrophotometer.

Test conditions: KBr tableting press method.

Figure 20:
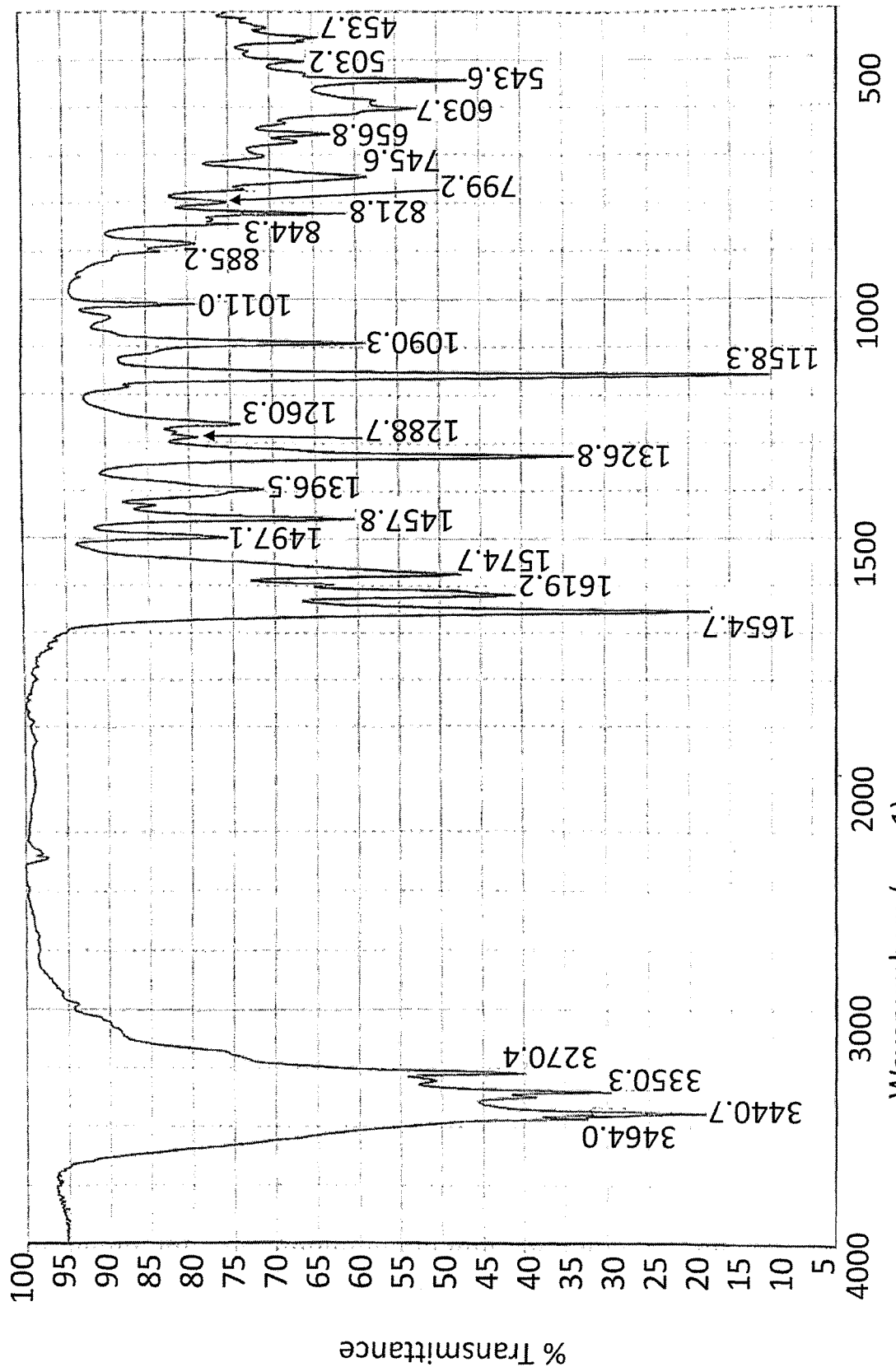
FIG. 20. Infra-red spectrogram of HPN-01.

Test results: Absorption peaks were found on HPN-01 infrared absorption spectrum at about 3464.0 cm-1、3440.7 cm-1、3350.3 cm-1、3270.4 cm-1、1654.7 cm-1、1619.2 cm-1、1574.7 cm-1、1326.8 cm-1、1158.3 cm-1. (FIG. 20).

Example 14. HPN-01 Ultraviolet Spectrogram

An ultraviolet spectrogram of HPN-01 was generated using the following instrument and conditions.

Instrument type: Shimadzu UV-2600 UV spectrophotometer.

Test conditions: (1) methyl alcohol; (2) 0.1 mol/L hydrochloric acid solution; (3) 0.1 mol/L sodium hydroxide solution.

Figure 21:
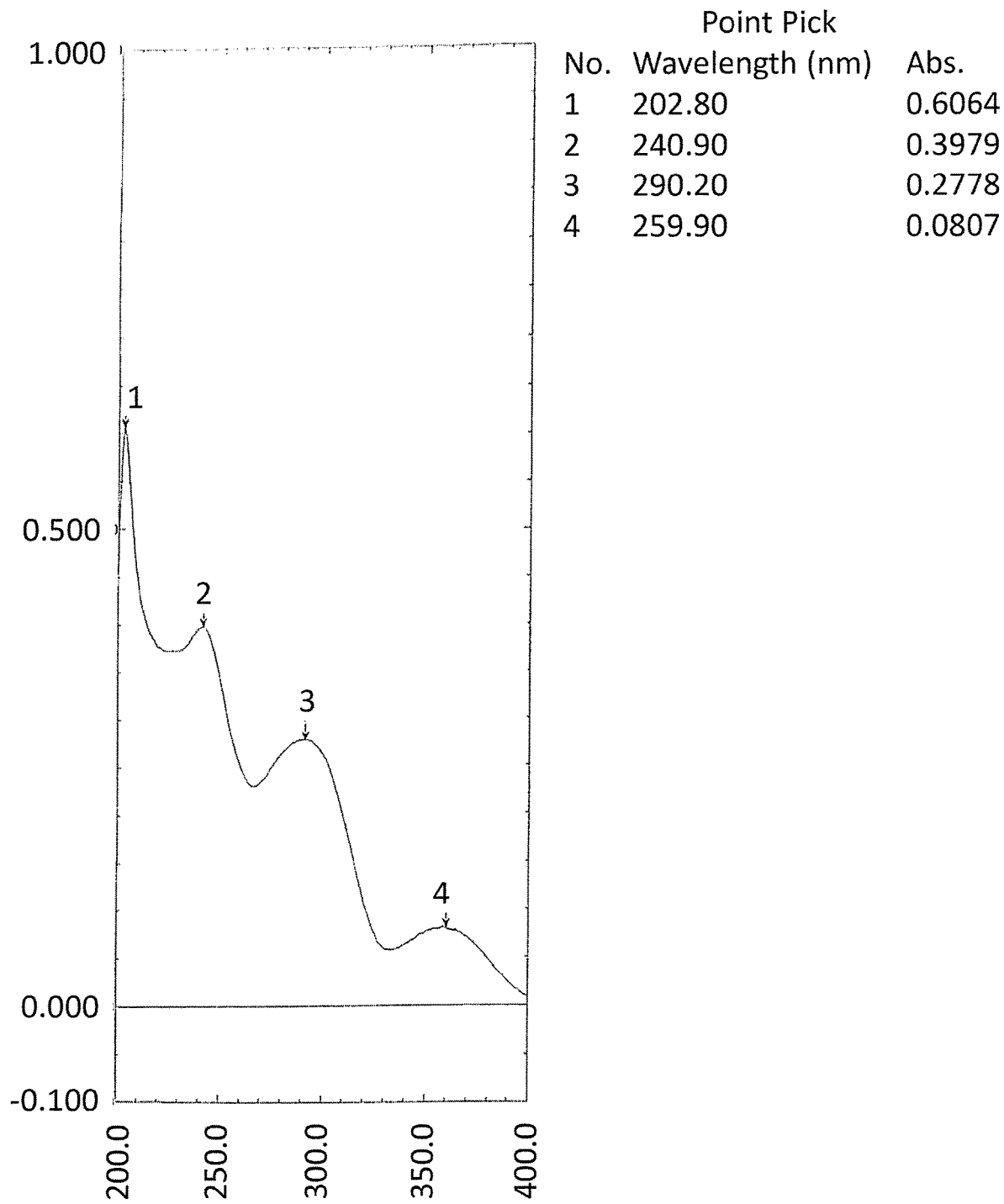
FIG. 21. Ultraviolet spectrogram (methyl alcohol) of HPN-01.
Figure 22:
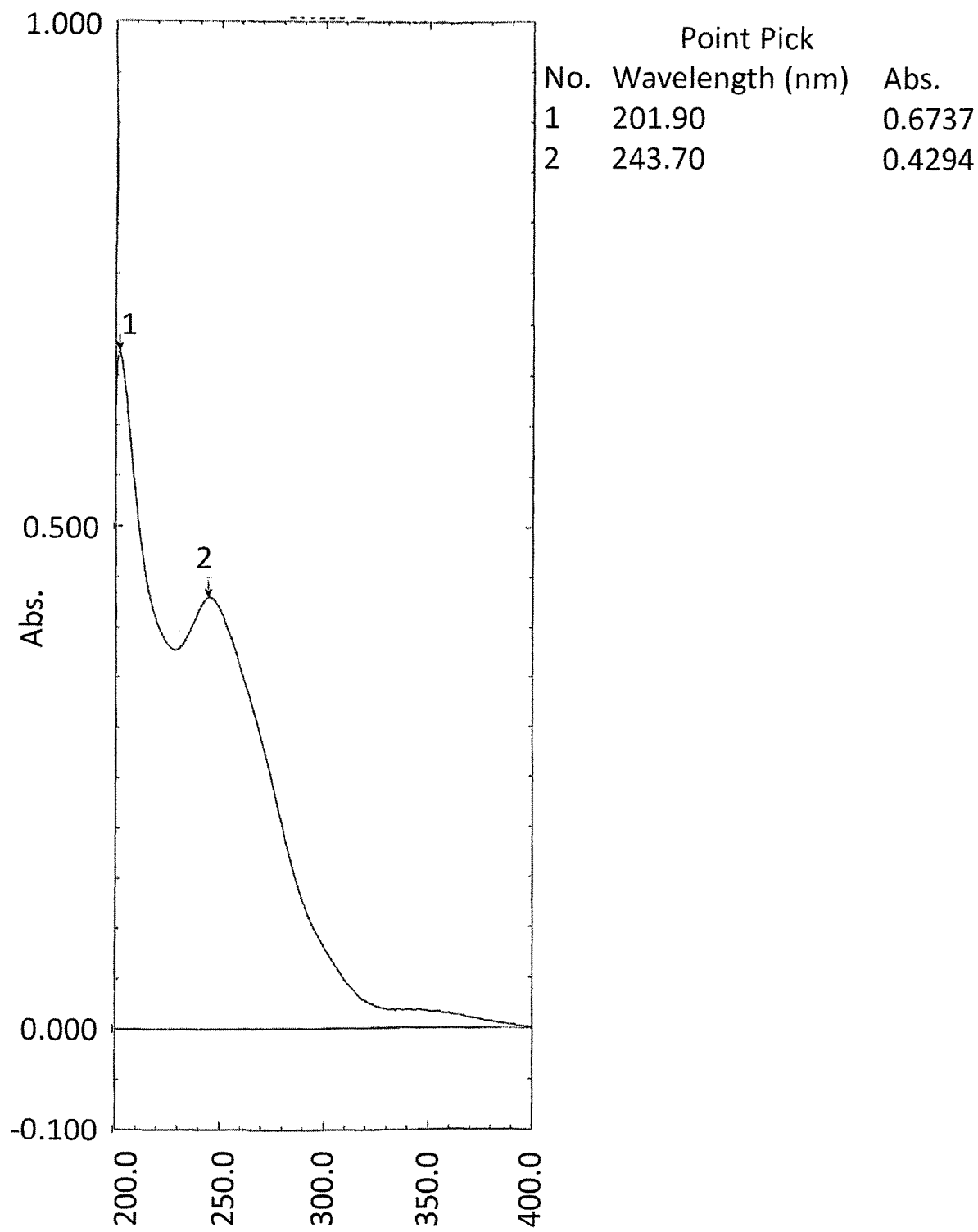
FIG. 22. Ultraviolet spectrogram (0.1 mol/L hydrochloric acid solution) of HPN-01.
Figure 23:
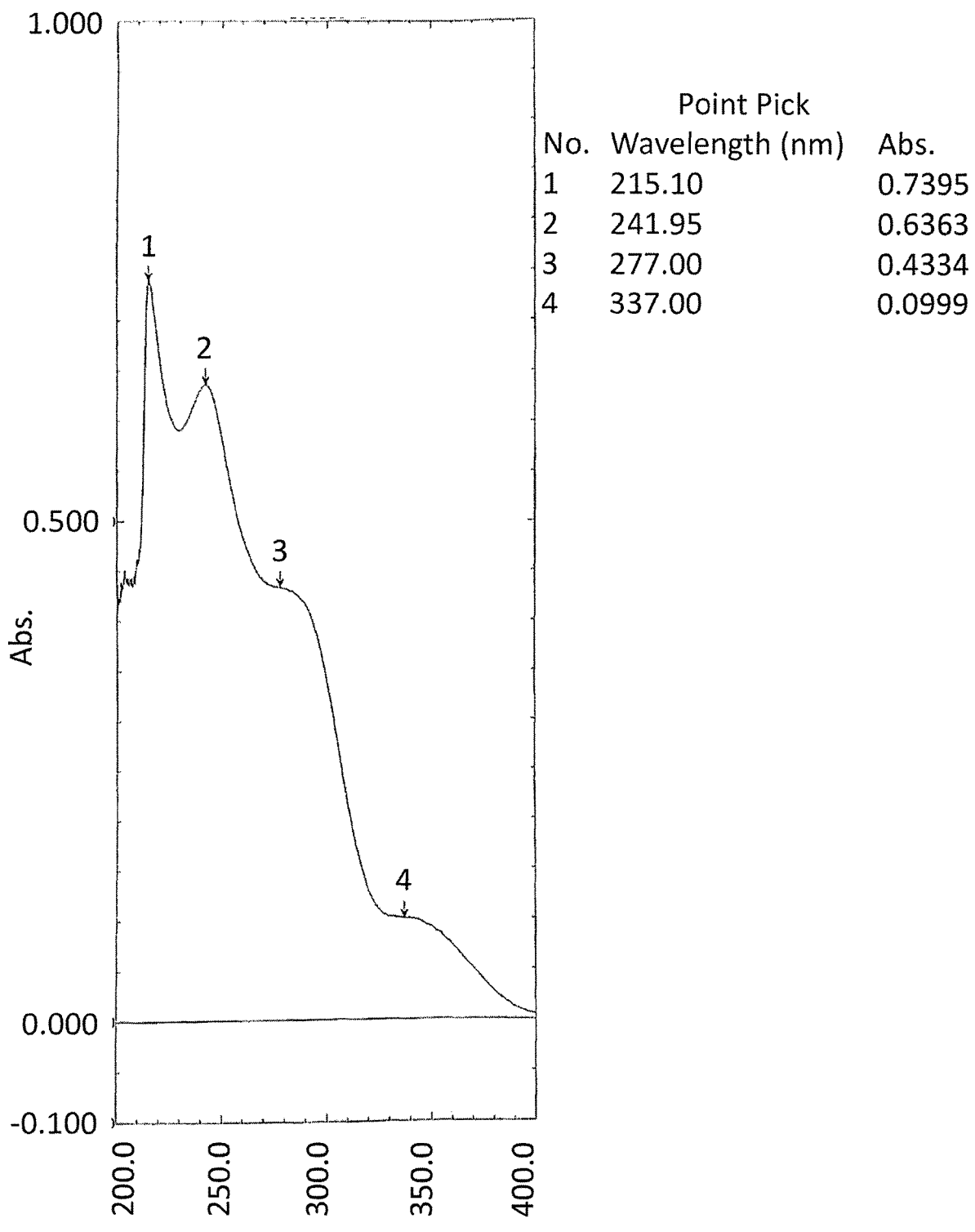
FIG. 23. Ultraviolet spectrogram (0.1 mol/L sodium hydroxide solution) of HPN-01.

Test results: Absorption peaks were found on HPN-01 ultraviolet spectrogram at (1) methyl alcohol: 202.80 λmax (nm)、240.90 λmax(nm)、290.20 λmax(nm) and 359.90 λmax(nm); (2) 0.1 mol/L hydrochloric acid solution: 201.90 λmax(nm) and 243.70 λmax(nm); (3) 0.1 mol/L sodium hydroxide solution: 215.10 λmax(nm)、241.95 λmax(nm) 、277.00 λmax(nm) and 337.00 λmax(nm). (FIGS. 21, 22, 23).

Example 15. HPN-01 Powder X-Ray Diffraction Pattern

A powder X-ray diffraction pattern of HPN-01 was generated using the following instrument and conditions.

Instrument type: Rigaku-D/max-rB Powder X-ray diffractometer.

Test conditions: Copper rake Kα1, operating voltage: 40 KV/40 mA, step length: 0.02, scanning speed: 4.0 degrees/min.

Figure 24:
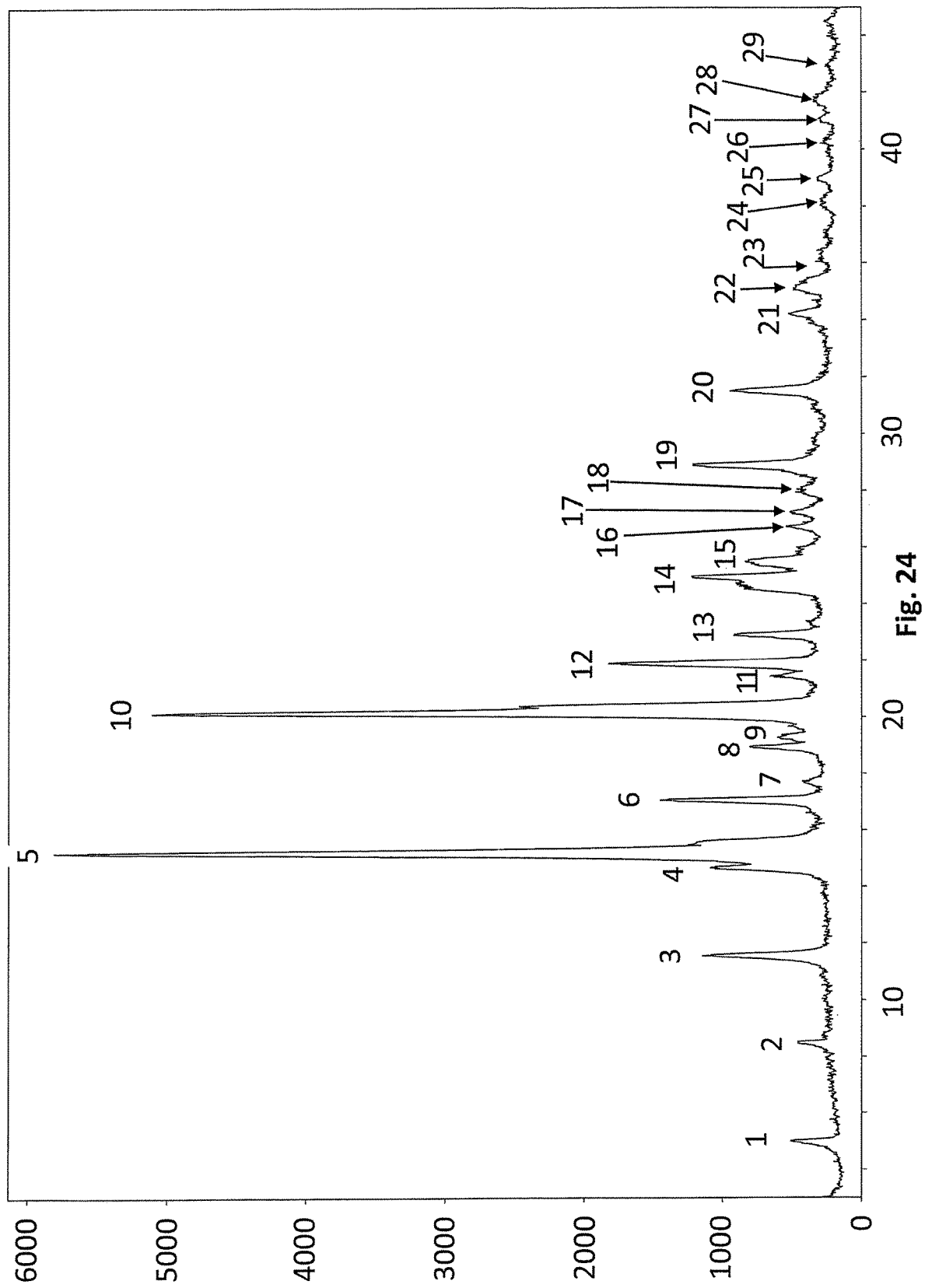
FIG. 24. Powder X-ray diffraction pattern of HPN-01.

Test results: X-ray powder diffraction expressed as degree 2Θ and interplanar spacing (d value) generated peaks at about 5.01 (17.62)、8.50 (10.39)、11.57 (7.65)、15.23 (5.81)、17.07 (5.19)、20.15 (4.40)、21.89 (4.06)、22.90 (3.88)、24.96 (3.56)、28.91 (3.09) and 31.52 (2.84). HPN-01 powder X-ray diffraction shows that this product is crystalline powder. (FIG. 24).

Example 16. HPN-01 Differential Thermal Analysis

A differential thermal analysis of HPN-01 was conducted using the following instrument and conditions.

Instrument type: DSC Q2000 Differential scanning calorimeter.

Test conditions: Heating rate: 10.0° C./min; Temperature range: 30-250° C.; Purge gas: nitrogen.

Figure 25:
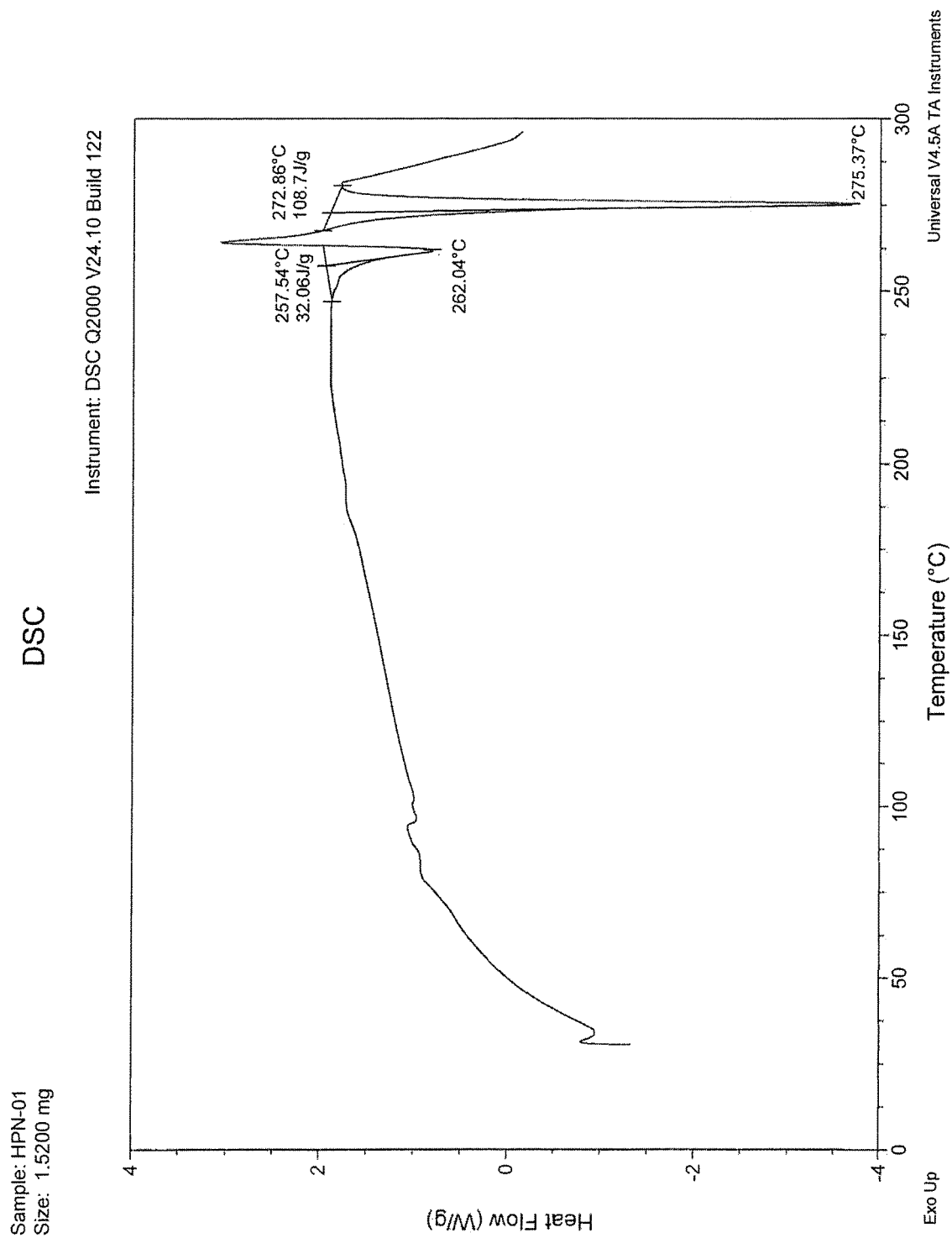
FIG. 25. Differential thermal analysis of HPN-01.

Test results: HPN-01 DSC absorbs heat transfer at about 275.37° C. melt decomposition. (FIG. 25).

Example 17. HPN-01 Elementary Composition

An elementary composition analysis of HPN-01 was conducted using the following instrument and conditions.

Instrument type: Q-Tofmicro LC/MS.

Test conditions are shown in FIG. 26.

Test results: High-resolution mass spectrometry was used to determine the elementary composition of HPN-01 compounds. [M-H]_400 peak was obtained using mass spectrometry electrospray ionization (ESI) anion detection method, and the composition of [M-H]_400 peak was determined to be $C_{19}H_{15}ClN_3O_3S$ using high-resolution mass spectrometry, therefore demonstrating that the elementary composition of HPN-01 is $C_{19}H_{15}ClN_3O_3S$. (Table 5, FIG. 26).

TABLE 5

HPN-01 High Resolution Mass Spectrometry Data List

| Measured value | Theoretical value | Deviation (m Da) | Accuracy (PPm) | Composition |
|---|---|---|---|---|
| 400.0520 | 400.0523 | −0.3 | −0.7 | $C_{19}H_{15}ClN_3O_3S$ |

Example 18. Synthesis of HPN-01 Derivatives

New derivatives of HPN-01 were synthesized according to the following processes:

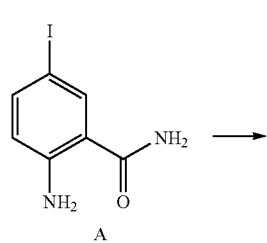

A

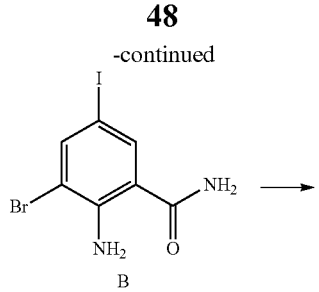

B

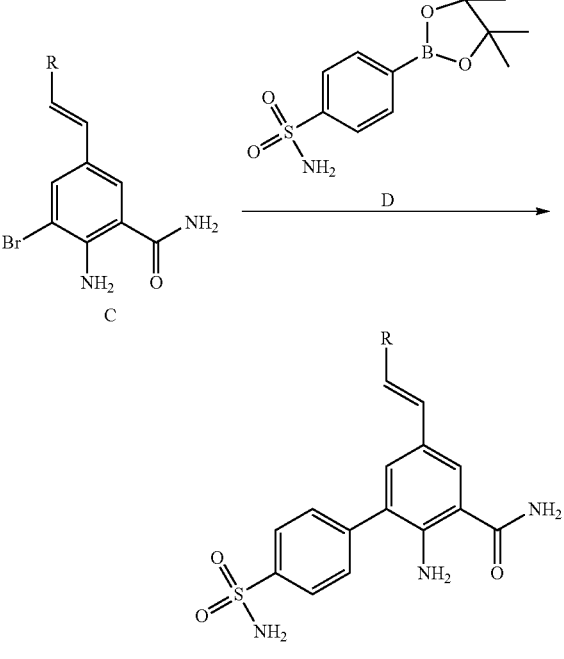

HPN-01101~HPN-01133

Step 1. Synthesis of Compound B 1.3 grams (g) of Compound A (5 mmol) and 0.9 g of N-bromosuccinimide (NBS) (5.25 mmol) were dissolved in 100 mL glacial acetic acid and stirred at room temperature for 1 hour. After the reaction was completed, the reaction solution was partially concentrated and poured into ice water and stirred vigorously. The solids were collected, dried, and subjected to silica gel column chromatography purification, resulting in isolation of Compound B. Analysis of isolated Compound B showed it had the following characteristics: Yield: 90%; 1H NMR: (300 MHz, DMSO-d6) δ: 6.77 (s, 2H), 7.42 (s, 1H), 7.71-7.77 (dd, 1H), 7.79-7.86 (dd, 1H), 8.02 ppm (s, 1H); MS (m/z): 341.87 (M+1)+.

Step 2. Synthesis of Compound C 1.2 g of Compound B (3 mmol) obtained from step 1, substituted alkene (3.3 mmol), 0.03 g palladium (II) acetate (Pd (OAc)2) (3%) and 0.8 ml triethanolamine (TEA) (6 mmol) were added to 50 mL of anhydrous dimethylformamide (DMF), and the mixture was stirred with microwave heating at 600 w at 110° C. for 90 min. The reaction was stopped, and the solution was poured into 200 mL of ice water and stirred continuously. Precipitated solids were collected, dried, and subjected to silica gel column chromatography purification, resulting in isolation of Compound C. The yield of Compound C was 55-83%.

Step 3. Synthesis of HPN-01 Series Compounds

A mixture of 10 mmol of Compound C (obtained from Step 2), 4.2 g Compound D (15 mmol), 0.35 g Bis(triphenylphosphine)palladium(II) dichloride (PdCl2(PPh3)2) (5%), and 2.8 g potassium carbonate (20 mmol) were dissolved in 50 mL of dioxane and 20 mL of water. The reaction was allowed for 30 hours at 80° C. under nitrogen protection. After the reaction was completed, the obtained solution was poured into ice water and stirred vigorously. The solids were collected, dried, and subjected to silica gel column chromatography purification, yielding Compounds HPN-01101 to HPN-01133. Structural information for each of these compounds is as follows:

HPN-01101: (E)-2-amino-5-styryl-4'-sulfamoyl-[1,1'-biphenyl]-3-carboxamide

Yield: 53%; $^1$H NMR: (300 MHz, CDCl$_3$) δ: 3.92 (s, 3H, CH$_3$—O), 4.55 (d, 2H, J=6.0 Hz, CH$_2$—Ar), 5.92 (s, 1H, NH), 6.86 (d, 1H, J=2.4 Hz, Ar—H), 6.99-7.05 (m, 3H, Ar—H), 7.32 (d, 1H, J=15.3 Hz, O═C—CH═C), 7.28-7.34 (m, 2H, Ar—H), 7.54 (d, 1H, J=15.3 Hz, O═C—C═CH), 8.04 (s, 1H, O—CH═C), 8.16 ppm (d, 1H, J=9.0 Hz, Ar—H); $^{13}$C NMR (75 MHz, CDCl$_3$) δ: 43.53, 55.32, 100.10, 114.49, 115.88, 116.59, 119.48, 123.08, 126.18, 129.99, 133.54, 143.15, 149.46, 155.87, 160.48, 165.11, 175.88; HRMS (m/z): 354.11 (M+1)$^+$ HPN-01102: (E)-2-amino-5-(3-chlorostyryl)-4'-sulfamoyl-[1,1'-biphenyl]-3-carboxamide Yield: 57%; $^1$H NMR: (300 MHz, CDCl$_3$) δ: 2.0 (s, 2H), 6.27 (s, 2H), 6.95 (d, 2H), 7.16 (s, 1H), 7.34-7.50 (m, 5H), 7.88-7.92 (dd, 4H), 8.07 (d, 1H). HRMS (m/z): 428.9 (M+1)$^+$ HPN-01103: (E)-2-amino-5-(3-bromostyryl)-4'-sulfamoyl-[1,1'-biphenyl]-3-carboxamide Yield: 59%; $^1$H NMR: (300 MHz, CDCl$_3$) δ: 2.0 (s, 2H), 6.27 (s, 2H), 6.95 (d, 2H), 7.16 (s, 1H), 7.34 (d, 1H), 7.45-7.50 (d, 3H), 7.66 (m, 2H), 7.88-7.92 (dd, 4H), 8.07 (d, 1H). HRMS (m/z): 473.36 (M+1)$^+$ HPN-01104: (E)-2-amino-5-(3-fluorostyryl)-4'-sulfamoyl-[1,1'-biphenyl]-3-carboxamide Yield: 63%; $^1$H NMR: (300 MHz, CDCl$_3$) δ: 2.0 (s, 2H), 6.27 (s, 2H), 6.95 (d, 2H), 7.08-7.16 (m, 3H), 7.31 (m, 1H), 7.49-7.50 (m, 3H), 7.88-7.92 (dd, 4H), 8.07 (d, 1H). HRMS (m/z): 412.45 (M+1)$^+$ HPN-01105: (E)-4-(2-(6-amino-5-carbamoyl-4'-sulfamoyl-[1,1'-biphenyl]-3-yl)vinyl)phenyl acetate Yield: 50%; $^1$H NMR: (300 MHz, CDCl$_3$) δ: 2.31 (s, 3H), 5.02 (s, 2H), 6.90-6.95 (dd, 2H), 7.23 (s, 1H), 7.33-7.39 (t, 3H), 7.74 (d, 2H), 7.88-7.90 (d, 6H), 8.17 (d, 1H). HRMS (m/z): 452.5 (M+1)$^+$ HPN-01106: (E)-5-(4-acetamidostyryl)-2-amino-4'-sulfamoyl-[1,1'-biphenyl]-3-carboxamide Yield: 73%; $^1$H NMR: (300 MHz, CDCl$_3$) δ: 2.06 (s, 3H), 5.02 (s, 2H), 6.90-6.95 (dd, 2H), 7.23 (s, 1H), 7.39 (s, 1H), 7.80-7.90 (m, 8H), 8.03 (d, 2H), 8.17 (d, 1H), 10.16 (s, 1H). HRMS (m/z): 451.51 (M+1)$^+$ HPN-01107: (E)-2-amino-5-(4-chlorostyryl)-4'-sulfamoyl-[1,1'-biphenyl]-3-carboxamide Yield: 46%; $^1$H NMR: (300 MHz, CDCl$_3$) δ: 2.0 (s, 2H), 6.27 (s, 2H), 6.95 (d, 2H), 7.16 (s, 1H), 7.49-7.50 (t, 3H), 7.80-7.92 (m, 6H), 8.07 (d, 1H). HRMS (m/z): 428.9 (M+1)$^+$ HPN-01108: (E)-2-amino-5-(2-chlorostyryl)-4'-sulfamoyl-[1,1'-biphenyl]-3-carboxamide Yield: 51%; $^1$H NMR: (300 MHz, CDCl$_3$) δ: 2.0 (s, 2H), 6.27 (s, 2H), 6.78 (d, 1H), 7.16-7.33 (m, 4H), 7.44-7.50 (m, 4H), 8.07 (d, 1H). HRMS (m/z): 428.9 (M+1)$^+$ HPN-01109: (E)-2-amino-5-(4-bromostyryl)-4'-sulfamoyl-[1,1'-biphenyl]-3-carboxamide Yield: 53%; $^1$H NMR: (300 MHz, CDCl$_3$) δ: 2.0 (s, 2H), 6.27 (s, 2H), 6.95 (d, 2H), 7.16 (s, 1H), 7.50-7.60 (t, 4H), 7.73 (d, 2H), 7.88-7.92 (dd, 4H), 8.07 (d, 1H), 7.88-7.92 (dd, 4H), 8.07 (s, 1H), 9.72 (t, 1H). HRMS (m/z): 473.35 (M+1)$^+$ HPN-01110: (E)-3-(2-(6-amino-5-carbamoyl-4'-sulfamoyl-[1,1'-biphenyl]-3-yl)vinyl)phenyl acetate Yield: 73%; $^1$H NMR: (300 MHz, CDCl$_3$) δ: 2.31 (s, 3H), 5.02 (s, 2H), 6.95 (s, 2H), 7.15-7.23 (m, 4H), 7.53 (t, 1H), 7.67 (d, 1H), 7.88-7.90 (d, 6H), 8.17 (d, 1H). HRMS (m/z): 452.5 (M+1)$^+$ HPN-01111: (E)-3-(2-(6-amino-5-carbamoyl-4'-sulfamoyl-[1,1'-biphenyl]-3-yl)vinyl)phenyl butyrate Yield: 67%; $^1$H NMR: (300 MHz, CDCl$_3$) δ: 0.90 (t, 3h), 1.73 (m, 2H), 2.0 (s, 2H), 2.40 (dd, 2H), 6.27 (s, 2H), 6.95 (d, 2H), 7.16 (s, 1H), 7.45.7.50 (m, 4H), 7.72 (d, 2H). HRMS (m/z): 482.56 (M+1)$^+$ HPN-01112: (E)-2-amino-5-(3-butyramidostyryl)-4'-sulfamoyl-[1,1'-biphenyl]-3-carboxamide Yield: 51%; $^1$H NMR: (300 MHz, CDCl$_3$) δ: 0.98 (t, 3H), 1.79 (m, 2H), 2.32 (t, 2H), 5.02 (s, 2H), 6.95 (s, 2H), 7.23 (s, 2H), 7.36-7.39 (m, 3H), 7.56 (m, 1H), 7.64 (s, 1H), 7.88-7.90 (d, 6H), 8.17 (d, 1H), 10.0 (s, 1H). HRMS (m/z): 479.57 (M+1)$^+$ HPN-01113: (E)-3-(6-amino-5-carbamoyl-4'-sulfamoyl-[1,1'-biphenyl]-3-yl)acrylic acid Yield: 53%; $^1$H NMR: (300 MHz, CDCl$_3$) δ: 6.36 (d, 1H, J=15.9 Hz, O═C—CH═C), 6.87 (s, 2H, NH$_2$—Ar), 7.36 (s, 1H, NH$_2$—C═O), 7.40-7.42 (m, 3H, S—NH$_2$, 6-ArH), 7.44 (d, 1H, J=15.9 Hz, O═C—C═CH), 7.59 (d, 2H, J=7.8 Hz, S—ArH), 7.89 (d, 2H, J=7.8 Hz, S—ArH), 8.00 (s, 1H, 4-Ar—H), 8.04 (s, 1H, NH$_2$—C═O), 12.06 ppm (s, 1H, COOH); MS (m/z): 362.08 (M+1)$^+$ HPN-01114: methyl (E)-3-(6-amino-4'-(amino(methylene)sulfinyl)-5-carbamoyl-[1,1'-biphenyl]-3-yl)acrylate Yield: 52%; $^1$H NMR: (300 MHz, DMSO-d6) δ: 3.68 (s, 3H, CH$_3$—O), 6.47 (d, 1H, J=15.9 Hz, O═C—CH═C), 6.92 (s, 2H, NH$_2$—Ar), 7.37 (s, 1H, NH$_2$—C═O), 7.43 (s, 2H, S—NH₂), 7.48 (s, 1H, 6-ArH), 7.51 (d, 1H, J=15.9 Hz, O=C—C=CH), 7.59 (d, 2H, J=7.8 Hz, S—ArH), 7.51 (d, 2H, J=8.1 Hz, S—ArH), 8.00-8.03 ppm (m, 2H, 4-Ar—H, NH₂—C=O); MS (m/z): 376.09 (M+1)⁺;

HPN-01115: ethyl (E)-3-(6-amino-5-carbamoyl-4'-sulfamoyl-[1,1'-biphenyl]-3-yl)acrylate Yield: 36%; ¹H NMR: (300 MHz, DMSO-d6) δ: 1.21-1.25 (t, 3H, CH₃), 4.11-4.18 (q, 2H, CH₂), 6.46 (d, 1H, J=15.9 Hz, O=C—CH=C), 6.92 (s, 2H, NH₂—Ar), 7.36 (s, 1H, NH₂—C=O), 7.43 (s, 2H, S—NH₂), 7.47 (s, 1H, 6-ArH), 7.50 (d, 1H, J=15.9 Hz, O=C—C=CH), 7.59 (d, 2H, J=7.8 Hz, S—ArH), 7.89 (d, 2H, J=8.4 Hz, S—ArH), 8.03-8.04 ppm (m, 2H, 4-Ar—H, NH₂—C=O); ¹³C NMR (75 MHz, DMSO-d₆) δ: 14.23, 59.89, 113.74, 114.52, 114.82, 121.10, 121.58, 126.49, 129.83, 133.55, 135.32, 141.63, 143.10, 143.55, 144.49, 147.85, 148.92, 171.06, 171.31 ppm; MS (m/z): 390.11 (M+1)⁺;

HPN-01116: isopropyl (E)-3-(6-amino-5-carbamoyl-4'-sulfamoyl-[1,1'-biphenyl]-3-yl)acrylate Yield: 46%; ¹H NMR: (300 MHz, DMSO-d₆) δ: 1.22 (d, 6H, J=6.3 Hz, CH₃), 4.94-5.02 (m, 1H, CH), 6.44 (d, 1H, J=15.9 Hz, O=C—CH=C), 6.94 (s, 2H, NH₂—Ar), 7.37 (s, 1H, NH₂—C=O), 7.44 (s, 2H, S—NH₂), 7.46 (s, 1H, 6-ArH), 7.48 (d, 1H, J=15.9 Hz, O=C—C=CH), 7.59 (d, 2H, J=8.1 Hz, S—ArH), 7.88 (d, 2H, J=8.4 Hz, S—ArH), 8.04-8.05 ppm (m, 2H, 4-Ar—H, NH₂—C=O); MS (m/z): 404.12 (M+1)⁺;

HPN-01117: butyl (E)-3-(6-amino-5-carbamoyl-4'-sulfamoyl-[1,1'-biphenyl]-3-yl)acrylate Yield: 83%; ¹H NMR: (300 MHz, CDCl₃) δ: 2.83-2.87 (m, 2H, CH₂-Ar) 3.60-3.66 (m, 2H, CH₂—N), 3.92 (s, 3H, CH₃—O), 5.70 (s, 1H, NH), 6.86 (d, 1H, J=2.1 Hz, Ar—H), 6.99-7.03 (m, 3H, Ar—H), 7.15-7.20 (m, 2H, Ar—H), 7.27 (d, 1H, J=15.0 Hz, O=C—C=CH), 7.45 (d, 1H, J=15.0 Hz, O=C—C=CH), 8.03 (s, 1H, O—CH=C), 8.15 ppm (d, 1H, J=8.7 Hz, Ar—H); ¹³C NMR (75 MHz, DMSO-d6) δ: 35.30, 40.75, 55.40, 100.11, 114.99, 115.13, 116.45, 119.03, 123.35, 127.54, 131.00, 135.53.53, 141, 156.32, 158.44, 161.78, 166.32, 177.83 ppm; HRMS (m/z): 368.13 (M+1)⁺;

HPN-01118: heptyl (E)-3-(6-amino-5-carbamoyl-4'-sulfamoyl-[1,1'-biphenyl]-3-yl)acrylate Yield: 39%; ¹H NMR: (300 MHz, DMSO-d₆) δ: 0.83-0.86 (t, 3H, CH₃), 1.25-1.34 (m, 8H, CH₂), 1.58-1.62 (m, CH₂—C—O), 4.07-4.11 (t, 2H, CH₂—O), 6.46 (d, 1H, J=15.9 Hz, O=C—CH=C), 6.93 (s, 2H, NH₂—Ar), 7.38 (s, 1H, NH₂—C=O), 7.44 (s, 2H, S—NH₂), 7.47 (s, 1H, 6-ArH), 7.49 (d, 1H, J=15.9 Hz, O=C—C=CH), 7.59 (d, 2H, J=8.4 Hz, S—ArH), 7.88 (d, 2H, J=8.4 Hz, S—ArH), 8.00-8.03 ppm (m, 2H, 4-Ar—H, NH₂—C=O); MS (m/z): 460.19 (M+1)⁺;

HPN-01119: decyl (E)-3-(6-amino-5-carbamoyl-4'-sulfamoyl-[1,1'-biphenyl]-3-yl)acrylate Yield: 44%; ¹H NMR: (300 MHz, CDCl₃) δ: 1.39-1.43 (t, 3H, CH₃—CH₂), 3.93 (s, 3H, CH₃—O), 4.04 (dd, 2H, J₁=6.9 Hz, J₂=6.9 Hz, CH₂—CH₃), 6.86-6.89 (m, 2H, Ar—H), 7.02 (dd, 2H, J₁=2.1 Hz, J₂=2.1 Hz, Ar—H), 7.36 (d, 1H, J=15.3 Hz, O=C—CH=C), 7.40 (s, 1H, Ar—H), 7.52 (d, J=15.0 Hz, Ar—H), 7.70 (d, 1H, J=15.3 Hz, O=C—C=CH), 8.07 (s, 1H, O—CH=C), 8.19 ppm (d, 1H, J=9.0 Hz, Ar—H); ¹³C NMR (75 MHz, CDCl₃) δ: 15.10, 56.71, 57.15 100.95, 115.45, 116.61, 122.84, 126.88, 129.11, 134.55, 158.94, 159.16, 165.64, 166.56, 177.26 ppm; HRMS (m/z): 366.13 (M+1)⁺;

HPN-01120: benzyl (E)-3-(6-amino-5-carbamoyl-4'-sulfamoyl-[1,1'-biphenyl]-3-yl)acrylate Yield: 31%; ¹H NMR: (300 MHz, DMSO-d₆) δ: 5.18 (s, 2H, CH₂-Ph), 6.53 (d, 1H, J=15.9 Hz, O=C—CH=C), 6.95 (s, 2H, NH₂—Ar), 7.30-7.35 (m, 5H, NH₂—C=O, S—NH₂, ArH), 7.38-7.44 (m, 4H, ArH), 7.49 (d, 1H, J=15.9 Hz, O=C—C=CH), 7.55 (d, 2H, J=8.4 Hz, S—ArH), 7.89 (d, 2H, J=8.4 Hz, S—ArH), 8.02-8.04 ppm (m, 2H, 4-Ar—H, NH₂—C=O); MS (m/z): 452.12 (M+1)⁺;

HPN-01121: (E)-4-(3-(6-amino-5-carbamoyl-4'-sulfamoyl-[1,1'-biphenyl]-3-yl)acrylamido)benzoic Acid Yield: 23%; ¹H NMR: (300 MHz, CDCl₃) δ: 3.47 (d, 4H, J=4.2 Hz), 3.83 (s, 4H, J=5.4 Hz), 3.92 (s, 3H), 6.55 (d, 1H, J=2.1 Hz), 6.86 (m, 2H), 6.97 (d, 1H, J=2.4 Hz), 7.00 (d, 1H, J=2.4 Hz), 7.38 (d, 1H, J=1.8 Hz), 8.14 (m, 3H), 8.23 ppm (d, 1H, J=9 Hz). MS (m/z): 481.5 (M+1)⁺;

HPN-01122: (E)-2-amino-5-(3-((4-hydroxyphenyl)amino)-3-oxoprop-1-en-1-yl)-4'-sulfamoyl-[1,1'-biphenyl]-3-carboxamide Yield: 30%; ¹H NMR: (300 MHz, DMSO-d₆) δ: 6.57 (d, 1H, J=15.6 Hz, O=C—CH=C), 6.68 (d, 2H, J=8.7 Hz, Ar—H), 6.73 (s, 2H, Ar—NH₂), 7.37-7.47 (m, 5H, NH₂—C=O, O=C—C=CH, Ar—H), 7.44 (s, 2H, NH₂—S), 7.62 (d, 2H, J=8.4 Hz, Ar—H), 7.88 (s, 1H, Ar—H), 7.91 (d, 2H, J=8.4 Hz, Ar—H), 8.03 (s, 1H, NH₂—C=O), 9.17 (s, 1H, OH), 9.73 ppm (s, 1H, NH); MS (m/z): 453.12 (M+1)⁺;

HPN-01123: phenethyl (E)-3-(6-amino-5-carbamoyl-4'-sulfamoyl-[1,1'-biphenyl]-3-yl)acrylate Yield: 37%; ¹H NMR: (300 MHz, DMSO-d₆) δ: 2.92-2.96 (t, 2H, CH₂-Ph), 4.30-4.34 (t, 2H, CH₂—O), 6.44 (d, 1H, J=15.6 Hz, O=C—CH=C), 6.94 (s, 2H, NH₂—Ar), 7.26 (s, 1H, NH₂—C=O), 7.28 (s, 2H, S—NH₂), 7.30-7.47 (m, 6H, ArH), 7.49 (d, 1H, J=15.9 Hz, O=C—C=CH), 7.59 (d, 2H, J=8.4 Hz, S—ArH), 7.89 (d, 2H, J=8.1 Hz, S—ArH), 8.02-8.05 ppm (m, 2H, 4-Ar—H, NH₂—C=O); MS (m/z): 466.14 (M+1)⁺;

HPN-01124: furan-2-ylmethyl (E)-3-(6-amino-5-carbamoyl-4'-sulfamoyl-[1,1'-biphenyl]-3-yl)acrylate Yield: 80%; ¹H NMR: (300 MHz, CDCl₃) δ: 2.91-2.96 (m, 2H, CH₂—Ar), 3.63-3.69 (m, 2H, CH₂—N), 3.92 (s, 3H, CH₃—O), 5.72 (s, 1H, NH), 6.86 (d, 1H, J=2.4 Hz, Ar—H), 7.00-7.11 (m, 3H, Ar—H), 7.19-7.25 (n, 2H, Ar—H), 7.28 (d, 1H, J=15.3 Hz, O=C—CH=C), 7.45 (d, 1H, J=15.0 Hz, O=C—C=CH), 8.03 (s, 1H, O—CH=C), 8.16 ppm (d, 1H, J=9.0 Hz, Ar—H); ¹³C NMR (75 MHz, CDCl₃) δ: 35.26, 40.75, 55.38, 100.10, 114.75, 115.23, 116.88, 119.04, 121.87, 124.98, 127.61, 127.95, 132.80, 141.17, 149.04, 158.00, 163.76, 166.90, 177.70 ppm; HRMS (m/z): 368.13 (M+1)⁺;

HPN-01125: (E)-2-amino-5-(3-oxo-3-(phenylamino) prop-1-en-1-yl)-4'-sulfamoyl-[1,1'-biphenyl]-3-carboxamide Yield: 76%; $^1$H NMR: (300 MHz, CDCl$_3$) δ: 3.93 (s, 3H, CH$_3$—O), 4.58 (d, 1H, J=6.0 Hz, CH$_2$—Ar), 6.03 (s, 1H, NH), 6.74 (s, 1H, Ar—H), 6.87 (d, 1H, J=2.4 Hz, Ar—H), 6.94-7.00 (m, 2H, Ar—H), 7.09 (d, 1H, J=7.5 Hz, Ar—H), 7.28-7.36 (m, 2H, Ar—H, O=C—CH=C), 7.58 (d, 1H, J=15.0 Hz, O=C—C=CH), 8.05 (s, 1H, O—CH=C), 8.16 ppm (d, 1H, J=9.0 Hz, Ar—H); $^{13}$C NMR (75 MHz, CDCl$_3$) δ: 44.53, 55.32, 100.10, 113.43, 116.33, 118.96, 119.83, 120.32, 122.58, 127.07, 127.76, 140.43, 143.32, 149.99, 160.22, 162.48, 163.02, 165.89, 175.88 ppm; HRMS (m/z): 354.11 (M+1)$^+$;

HPN-01126: (E)-2-amino-5-(3-oxo-3-(p-tolylamino) prop-1-en-1-yl)-4'-sulfamoyl-[1,1'-biphenyl]-3-carboxamide Yield: 57%; $^1$H NMR: (300 MHz, DMSO-d$_6$) δ: 2.24 (s, 3H, CH$_3$), 6.62 (d, 1H, J=15.6 Hz, O=C—CH=C), 6.75 (s, 2H, Ar—NH$_2$), 7.11 (d, 2H, J=8.4 Hz, Ar—H), 7.37 (s, 2H, NH$_2$—C=O), 7.43 (s, 2H, NH$_2$—S), 7.45 (d, 1H, J=15.3 Hz, O=C—C=CH), 7.55 (d, 2H, J=8.4 Hz, Ar—H), 7.64 (d, 2H, J=8.1 Hz, Ar—H), 7.90-7.94 (q, 3H, Ar—H), 8.02 (s, 1H, Ar—H), 9.88 ppm (s, 1H, NH); $^{13}$C NMR (75 MHz, DMSO-d$_6$) δ: 20.39, 114.87, 118.06, 118.98, 121.57, 126.24, 126.93, 129.05, 129.49, 129.79, 131.75, 131.89, 136.96, 139.51, 141.68, 143.10, 147.93, 163.80, 170.95 ppm; MS (m/z): 451.14 (M+1)$^+$;

HPN-01127: (E)-2-amino-5-(3-oxo-3-(m-tolylamino)prop-1-en-1-yl)-4'-sulfamoyl-[1,1'-biphenyl]-3-carboxamide Yield: 36%; $^1$H NMR: (300 MHz, DMSO-d$_6$) δ: 2.27 (s, 3H, CH$_3$), 6.61 (d, 1H, J=15.6 Hz, O=C—CH=C), 6.76 (s, 2H, Ar—NH$_2$), 6.82 (d, 2H, J=9 Hz, Ar—H), 7.08-7.20 (m, 3H, NH$_2$—C=O, O=C—C=CH), 7.39-7.51 (m, 5H, NH$_2$—S, Ar—H), 7.63 (d, 1H, J=8.7 Hz, Ar—H), 7.88-7.94 (m, 3H, Ar—H), 8.01 (s, 1H, NH$_2$—C=O), 9.89 ppm (s, 1H, NH); MS (m/z): 451.14 (M+1)$^+$;

HPN-01128: (E)-2-amino-5-(3-((4-methoxyphenyl) amino)-3-oxoprop-1-en-1-yl)-4'-sulfamoyl-[1,1'-biphenyl]-3-carboxamide Yield: 69%; $^1$H NMR: (300 MHz, CDCl$_3$) δ: 3.32 (s, 3H, CH$_3$), 3.94 (s, 3H, CH$_3$—O), 6.89 (d, 1H, J=2.4 Hz, Ar—H), 7.02-7.06 (dd, 1H, J$_1$=2.4 Hz, J$_2$=2.4 Hz, Ar—H), 7.11 (d, 1H, J=6.9 Hz, Ar—H), 7.19-7.28 (m, 2H, Ar—H), 7.41 (d, 1H, J=15.0 Hz, O=C—CH=C), 7.77 (d, 1H, J=15.3 Hz, O=C—C=CH), 8.04-8.07 (m, 1H, Ar—H), 8.09 (s, 1H, O—CH=C), 68.20 ppm (d, 1H, J=9.0 Hz, Ar—H); $^{13}$C NMR (75 MHz, CDCl$_3$) δ: 18.33, 55.85, 100.20, 114.05, 114.45, 116.84, 118.06, 121.76, 125.09, 127.57, 128.74, 129.26, 130.86, 131.94, 133.62, 140.95, 148.55, 157.78, 164.26, 167.86, 172.17; HRMS (m/z): 336.12 (M+1)$^+$;

HPN-01129: (E)-2-amino-5-(3-((4-ethoxyphenyl) amino)-3-oxoprop-1-en-1-yl)-4'-sulfamoyl-[1,1'-biphenyl]-3-carboxamide Yield: 43%; $^1$H NMR: (300 MHz, DMSO-d$_6$) δ: 1.27-1.32 (t, 3H, CH$_3$), 3.94-5.01 (q, 2H, CH$_2$), 6.57 (d, 1H, J=15.6 Hz, O=C—CH=C), 6.74 (s, 2H, Ar—NH$_2$), 6.85 (d, 2H, J=9 Hz, Ar—H), 7.38 (s, 2H, NH$_2$—C=O), 7.41 (d, 1H, J=15.6 Hz, O=C—C=CH), 7.43 (s, 2H, NH$_2$—S), 7.55 (d, 2H, J=9 Hz, Ar—H), 7.62 (d, 2H, J=8.4 Hz, Ar—H), 7.89 (s, 1H, Ar—H), 7.90 (d, 2H, J=8.7 Hz, Ar—H), 8.03 (s, 1H, NH$_2$—C=O), 9.83 ppm (s, 1H, NH); MS (m/z): 481.15 (M+1)$^+$;

HPN-01130: (E)-2-amino-5-(3-((4-chlorophenyl) amino)-3-oxoprop-1-en-1-yl)-4'-sulfamoyl-[1,1'-biphenyl]-3-carboxamide Yield: 46%; $^1$H NMR: (300 MHz, DMSO-d$_6$) δ: 6.59 (d, 1H, J=15.6 Hz, O=C—CH=C), 6.79 (s, 2H, Ar—NH$_2$), 7.34-7.39 (m, 4H, Ar—H, NH$_2$—C=O), 7.44 (s, 2H, NH$_2$—S), 7.46 (d, 1H, J=15.6 Hz, O=C—C=CH), 7.62 (d, 2H, J=8.4 Hz, Ar—H), 7.69 (d, 2H, J=9 Hz, Ar—H), 7.91-7.94 (m, 3H, S—ArH, 4-Ar—H), 8.03 (s, 1H, NH$_2$—C=O), 10.12 ppm (s, 1H, NH); MS (m/z): 472.08 (M+1)$^+$;

HPN-01131: (E)-2-amino-5-(3-(benzylamino)-3-oxoprop-1-en-1-yl)-4'-sulfamoyl-[1,1'-biphenyl]-3-carboxamide Yield: 38%; $^1$H NMR: (300 MHz, DMSO-d$_6$) δ: 4.37 (t, 2H, CH$_2$—N), 6.48 (d, 1H, J=15.9 Hz, O=C—CH=C), 7.23-7.34 (m, 7H, NH$_2$—Ar, NH$_2$—C=O, S—NH$_2$, ArH), 7.38-7.42 (3H, Ar—H, O=C—C=CH), 7.60 (d, 2H, J=8.4 Hz, S—ArH), 7.85-7.93 (m, 3H, S—ArH, 4-Ar—H), 8.02 (s, 1H, NH$_2$—C=O), 8.38 ppm (s, 1H, NH—C=O); MS (m/z): 451.14 (M+1)$^+$;

HPN-01132: (E)-2-amino-5-(3-((4-fluorophenethyl) amino)-3-oxoprop-1-en-1-yl)-4'-sulfamoyl-[1,1'-biphenyl]-3-carboxamide Yield: 54%; $^1$H NMR: (300 MHz, CDCl$_3$) δ: 2.33 (s, 3H, CH$_3$), 3.93 (s, 3H, CH$_3$—O), 6.87 (d, 1H, J=2.1 Hz, Ar—H), 7.01-7.04 (dd, 2H, J$_1$=2.4 Hz, J$_2$=2.4 Hz, Ar—H), 7.15 (d, 1H, J=8.1 Hz, Ar—H), 7.37 (d, 1H, J=15.0 Hz, O=C—CH=C), 7.50 (d, 2H, J=8.4 Hz, Ar—H), 7.69 (d, 1H, J=15.0 Hz, O=C—C=CH), 8.07 (s, 1H, O—CH=C), 8.19 ppm (d, 1H, J=9.0 Hz, Ar—H); $^{13}$C NMR (75 MHz, CDCl$_3$) δ: 21.36, 55.88, 100.24, 115.07, 118.02, 119.10, 121.64, 122.84, 127.31, 128.96, 133.23, 135.94, 141.52, 150.65, 157.14, 164.01, 164.34, 176.54; HRMS (m/z): 336.12 (M+1)$^+$;

HPN-01133: (E)-2-amino-5-(3-(cyclohexylamino)-3-oxoprop-1-en-1-yl)-4'-sulfamoyl-[1,1'-biphenyl]-3-carboxamide Yield: 54%; $^1$H NMR: (300 MHz, CDCl$_3$) δ: 3.93 (s, 3H, CH$_3$—O), 6.89 (d, 1H, J=2.1 Hz, Ar—H), 7.03-7.08 (m, 2H, Ar—H), 7.27-7.31 (m, 1H, Ar—H), 7.38 (s, 1H, Ar—H) 7.41 (d, 1H, J=15.0 Hz, O=C—CH=C), 7.76 (d, 1H, J=15.0 Hz, O=C—C=CH), 7.80 (s, 1H, Ar—H), 8.10 (s, 1H, O—CH=C), 8.19 ppm (d, 1H, J=9.0 Hz, Ar—H); $^{13}$C NMR (75 MHz, CDCl$_3$) δ: 55.64, 100.10, 114.65, 117.48, 119.54, 121.24, 122.51, 124.48, 127.44, 129.07, 132.71, 141.61, 149.69, 157.45, 164.15, 167.15, 175.50 ppm; HRMS (m/z): 357.06 (M+1)$^+$;

Example 19. Synthesis of the HPN-012 Series of HPN-01 Derivatives

A second series of HPN-01 derivatives were obtained using the following synthetic process:

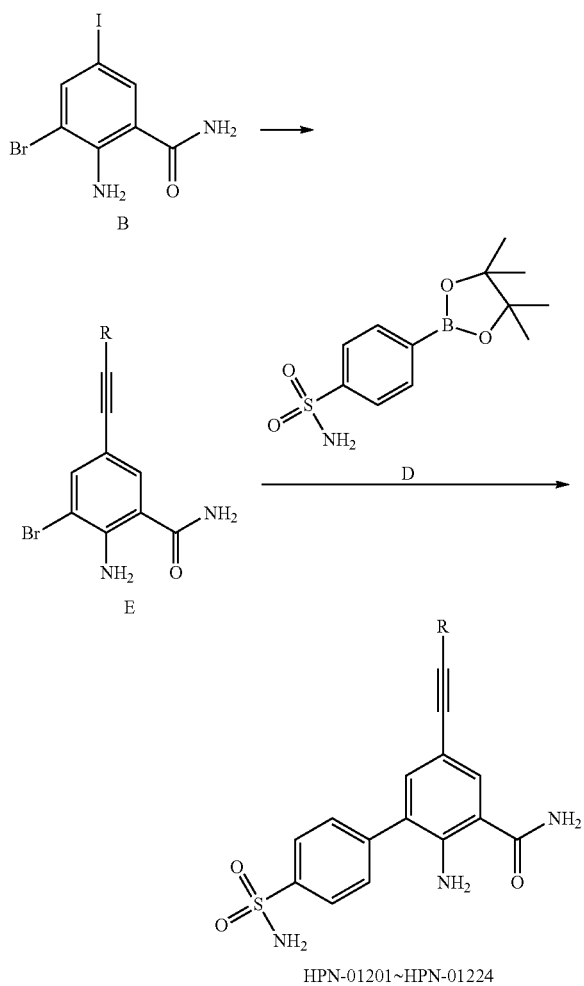

Step 1. Synthesis of Compound E 12 g Compound B (3 mmol), substituted alkyne (3.3 mmol), 0.03 g PdCl2(Ph3P)2 (3%) and 0.8 mL N,N-Diisopropylethylamine (DIEA) (6 mmol) were added to 50 mL of anhydrous tetrahydrofuran (THF), and the mixture was stirred with microwave heating at 600 W at 130° C. for 30 min. The reaction was stopped, and the yielded solution was poured into 200 mL ice water and stirred continuously. Precipitated solids were collected, dried, and subjected to gel column chromatography, resulting in isolation of Compound E. The yield of Compound E was 30-95%.

Step 2. Synthesis of HPN-012 Series Compounds

Compound E (10 mmol), 4.2 g Compound D (15 mmol), 0.35 g PdCl2(PPh3)2 (5%), and 2.8 g potassium carbonate (20 mmol) were dissolved in 50 mL dioxane, and 20 mL water. The reaction mixture was incubated at 80° C. for 30 hours under nitrogen protection. After the reaction was completed, the solution was poured into ice water and stirred vigorously. The solids were collected and dried, and subjected to silica gel column chromatography, yielding Compounds HPN-01201 to HPN-01224. Structural information for Compounds HPN-01201 to HPN-01224 is as follows:

HPN-01201: 2-amino-5-(3-hydroxyprop-1-ynyl)-4'-sulfamoylbiphenyl-3-carboxamide

Yield: 60%; $^1$H NMR: (300 MHz, CDCl$_3$) δ: 2.26 (s, 3H), 2.34 (s, 3H), 3.93 (s, 3H), 6.89 (m, 1H), 7.04 (m, 2H), 7.12 (d, 1H, J=13.2 Hz), 7.39 (d, 1H, J=15 Hz), 7.75 (d, 1H, J=14.7 Hz), 7.87 (s, 1H), 8.08 (s, 1H), 8.19 ppm (d, 1H, J=8.7 Hz); MS (m/z): 346.37 (M+1)$^+$;

HPN-01202: 2-amino-5-(phenylethynyl)-4'-sulfamoylbiphenyl-3-carboxamide

Yield: 38%; $^1$H NMR: (300 MHz, DMSO-d$_6$) δ: 6.72 (s, 2H, NH$_2$—Ar), 7.26 (d, 1H, J=1.8 Hz, NH$_2$—C=O), 7.36-7.42 (m, 3H, ArH), 7.43 (s, 2H, S—NH$_2$), 7.46-7.50 (m, 2H, ArH), 7.61 (d, 2H, J=8.4 Hz, S—ArH), 7.62 (s, 1H, 4-Ar—H), 7.86 (d, 1H, J=1.8 Hz, NH$_2$—C=O), 7.90 (d, 2H, J=8.4 Hz, S—ArH), 8.05 ppm (s, 1H, 6-Ar—H); MS (m/z): 410.44 (M+1)$^+$;

HPN-01203: 2-amino-5-((4-fluorophenyl)ethynyl)-4'-sulfamoylbiphenyl-3-carboxamide Yield: 48%; $^1$H NMR: (300 MHz, CDCl$_3$) δ: 3.93 (s, 3H), 6.88 (d, 1H, J=2.4 Hz), 7.02 (m, 3H), 7.39 (m, 2H), 7.57 (d, 1H, J=1.5 Hz), 7.79 (d, 1H, J=1.8 Hz), 8.09 (s, 1H), 8.20 ppm (d, 1H, J=9 Hz); MS (m/z): 392.10 (M+1)$^+$;

HPN-01204: 2-amino-5-((4-methoxyphenyl)ethynyl)-4'-sulfamoylbiphenyl-3-carboxamide Yield: 60%; $^1$H NMR: (300 MHz, CDCl$_3$) δ: 2.26 (s, 3H), 2.34 (s, 3H), 3.93 (s, 3H), 6.89 (m, 1H), 7.04 (m, 2H), 7.12 (d, 1H, J=13.2 Hz), 7.39 (d, 1H, J=15 Hz), 7.75 (d, 1H, J=14.7 Hz), 7.87 (s, 1H), 8.08 (s, 1H), 8.19 ppm (d, 1H, J=8.7 Hz); MS (m/z): 422.47 (M+1)$^+$;

HPN-01205: 2-amino-5-((4-chlorophenyl)ethynyl)-4'-sulfamoyl-[1,1'-biphenyl]-3-carboxamide Yield: 55%; $^1$H NMR: (300 MHz, CDCl$_3$) δ: 2.0 (s, 2H), 6.27 (s, 2H), 7.45-7.53 (m, 6H), 7.68 (s, 1H), 7.88-7.92 (dd, 4H), 8.14 (d, 1H); MS (m/z): 426.89 (M+1)$^+$;

HPN-01206: 2-amino-5-((3-chlorophenyl)ethynyl)-4'-sulfamoyl-[1,1'-biphenyl]-3-carboxamide Yield: 57%; $^1$H NMR: (300 MHz, CDCl$_3$) δ: 2.0 (s, 2H), 6.27 (s, 2H), 7.48-7.56 (m, 6H), 7.88 (s, 1H), 7.88-7.92 (dd, 4H), 8.14 (d, 1H); MS (m/z): 471.34 (M+1)$^+$;

HPN-01207: 2-amino-5-((4-bromophenyl)ethynyl)-4'-sulfamoyl-[1,1'-biphenyl]-3-carboxamide Yield: 43%; $^1$H NMR: (300 MHz, CDCl$_3$) δ: 2.0 (s, 2H), 6.27 (s, 2H), 7.48-7.56 (m, 6H), 7.88 (s, 1H), 7.88-7.92 (dd, 4H), 8.14 (d, 1H); MS (m/z): 471.34 (M+1)$^+$;

HPN-01208: 2-amino-5-((3-bromophenyl)ethynyl)-4'-sulfamoyl-[1,1'-biphenyl]-3-carboxamide Yield: 45%; $^1$H NMR: (300 MHz, CDCl$_3$) δ: 2.0 (s, 2H), 6.27 (s, 2H), 7.30 (t, 1H), 7.50-7.53 (dd, 4H), 7.68 (d, 1H), 7.83-7.92 (m, 5H), 8.14 (d, 1H); MS (m/z): 471.34 (M+1)$^+$;

HPN-01209: 2-amino-4'-sulfamoyl-5-((trimethylsilyl)ethynyl)-[1,1'-biphenyl]-3-carboxamide Yield: 56%; $^1$H NMR: (300 MHz, CDCl$_3$) δ: 0.88 (t, 9H), 6.27 (s, 2H), 7.50 (s, 2H), 7.64 (d, 2H), 7.88-7.92 (dd, 4H), 8.10 (d, 1H); MS (m/z): 388.53 (M+1)$^+$;

HPN-01210: 3-(6-amino-5-carbamoyl-4'-sulfamoyl-[1,1'-biphenyl]-3-yl)prop-2-yn-1-yl 2-chlorobenzoate Yield: 55%; $^1$H NMR: (300 MHz, CDCl$_3$) δ: 4.99-5.02 (d, 4H), 7.23 (s, 2H), 7.39-7.41 (m, 2H), 7.69 (m, 1H), 7.86-7.95 (m, 8H), 8.34 (d, 1H); MS (m/z): 484.92 (M+1)$^+$;

HPN-01211: 3-(6-amino-5-carbamoyl-4'-sulfamoyl-[1,1'-biphenyl]-3-yl)prop-2-yn-1-yl 2-bromobenzoate Yield: 47%; $^1$H NMR: (300 MHz, CDCl$_3$) δ: 4.99-5.02 (d, 4H), 7.23 (s, 2H), 7.47 (m, 1H), 7.63-7.65 (m, 2H), 7.86-7.90 (m, 8H), 8.34 (d, 1H); MS (m/z): 529.38 (M+1)$^+$;

HPN-01212: 3-(6-amino-5-carbamoyl-4'-sulfamoyl-[1,1'-biphenyl]-3-yl)prop-2-yn-1-yl 2-methylbenzoate Yield: 50%; $^1$H NMR: (300 MHz, CDCl$_3$) δ: 2.53 (s, 3H), 4.99-5.02 (d, 4H), 7.16-7.28 (m, 5H), 7.72 (m, 1H), 7.86-7.90 (m, 8H), 8.34 (d, 1H); MS (m/z): 464.51 (M+1)$^+$;

HPN-01213: 3-(6-amino-5-carbamoyl-4'-sulfamoyl-[1,1'-biphenyl]-3-yl)prop-2-yn-1-yl 2-fluorobenzoate Yield: 69%; $^1$H NMR: (300 MHz, CDCl$_3$) δ: 4.99-5.02 (d, 4H), 7.30-7.31 (m, 2H), 7.47 (m, 1H), 7.86-7.99 (m, 8H), 8.34 (d, 1H); MS (m/z): 468.41 (M+1)$^+$;

HPN-01214: 3-(6-amino-5-carbamoyl-4'-sulfamoyl-[1,1'-biphenyl]-3-yl)prop-2-yn-1-yl 4-methylbenzoate Yield: 65%; $^1$H NMR: (300 MHz, CDCl$_3$) δ: 2.41 (s, 3H), 4, 99-5.02 (d, 3H), 7.20-7.23 (t, 4H), 7.86-7.90 (m, 8H), 8.34 (d, 1H); MS (m/z): 464.51 (M+1)$^+$;

HPN-01215: 3-(6-amino-5-carbamoyl-4'-sulfamoyl-[1,1'-biphenyl]-3-yl)prop-2-yn-1-yl 3-methylbenzoate Yield: 57%; $^1$H NMR: (300 MHz, CDCl$_3$) δ: 2.43 (s, 3H), 4, 99-5.02 (d, 3H), 7.23-7.27 (dd, 4H), 7.86-7.90 (m, 8H), 8.34 (d, 1H); MS (m/z): 464.51 (M+1)$^+$;

HPN-01216: 3-(6-amino-5-carbamoyl-4'-sulfamoyl-[1,1'-biphenyl]-3-yl)prop-2-yn-1-yl 3-methoxybenzoate Yield: 68%; $^1$H NMR: (300 MHz, CDCl$_3$) δ: 3.77 (s, 3H), 4.99-5.02 (d, 3H), 7.15-7.23 (m, 3H), 7.51 (s, 1H), 7.64-7.67 (m, 2H), 7.86-7.90 (m, 8H), 8.34 (d, 1H); MS (m/z): 480.51 (M+1)$^+$;

HPN-01217: 3-(6-amino-5-carbamoyl-4'-sulfamoyl-[1,1'-biphenyl]-3-yl)prop-2-yn-1-yl 2-methoxybenzoate Yield: 62%; $^1$H NMR: (300 MHz, CDCl$_3$) δ: 3.90 (s, 3H), 4.99-5.02 (d, 3H), 7.18-7.23 (m, 3H), 7.53-7.56 (m, 2H), 7.86-7.90 (m, 8H), 8.34 (d, 1H); MS (m/z): 480.51 (M+1)$^+$;

HPN-01218: 3-(6-amino-5-carbamoyl-4'-sulfamoyl-[1,1'-biphenyl]-3-yl)prop-2-yn-1-yl 4-methoxybenzoate Yield: 63%; $^1$H NMR: (300 MHz, CDCl$_3$) δ: 3.81 (s, 3H), 4.99-5.02 (d, 3H), 6.85 (d, 2H), 7.23 (s, 2H), 7.94-7.90 (m, 9H), 8.34 (d, 1H); MS (m/z): 480.51 (M+1)$^+$;

HPN-01219: 3-(6-amino-5-carbamoyl-4'-sulfamoyl-[1,1'-biphenyl]-3-yl)prop-2-yn-1-yl 3-hydroxybenzoate Yield: 67%; $^1$H NMR: (300 MHz, CDCl$_3$) δ: 4.99-5.02 (d, 4H), 7.16 (t, 3H), 7.36 (d, 1 h) 7.47-7.65 (m, 2H), 8.34 (d, 1H), 9.45 (s, 1H), 7.86-7.90 (m, 8H), 8.34 (d, 1H) 9.45 (s, 1H); MS (m/z): 466.48 (M+1)$^+$;

HPN-01220: 3-(6-amino-5-carbamoyl-4'-sulfamoyl-[1,1'-biphenyl]-3-yl)prop-2-yn-1-yl 4-hydroxybenzoate Yield: 60%; $^1$H NMR: (300 MHz, CDCl$_3$) δ: 4.99-5.02 (d, 4H), 6.81 (d, 2H), 7.23 (s, 2H), 7.77 (s, 2H) 7.86-7.90 (m, 8H), 8.34 (d, 1H), 9.68 (s, 1H); MS (m/z): 466.48 (M+1)$^+$;

HPN-01221: 3-(6-amino-5-carbamoyl-4'-sulfamoyl-[1,1'-biphenyl]-3-yl)prop-2-yn-1-yl picolinate Yield: 70%; $^1$H NMR: (300 MHz, CDCl$_3$) δ: 4.99-5.02 (d, 4H), 7.23 (s, 2H), 7.86-7.90 (m, 8H), 8.34 (d, 1H), 8.29-8.34 (t, 2H), 8.89 (d, 1H); MS (m/z): 451.47 (M+1)$^+$;

HPN-01222: 3-(6-amino-5-carbamoyl-4'-sulfamoyl-[1,1'-biphenyl]-3-yl)prop-2-yn-1-yl 1H-pyrrole-2-carboxylate Yield: 50%; $^1$H NMR: (300 MHz, CDCl$_3$) δ: 4.99-5.02 (d, 4H), 8.28 (t, 1H), 7.23-7.30 (t, 4H), 8.34 (d, 1H), 11.30 (s, 1H); MS (m/z): 439.46 (M+1)$^+$;

HPN-01223: 3-(6-amino-5-carbamoyl-4'-sulfamoyl-[1,1'-biphenyl]-3-yl)prop-2-yn-1-yl acetate Yield: 55%; $^1$H NMR: (300 MHz, CDCl$_3$) δ: 2.0 (s, 2H), 2.31 (s, 3H), 4.82 (s, 2H), 6.27 (s, 2H), 7.50 (s, 2H), 7.64 (d, 2H), 7.88-7.92 (dd, 4H), 8.10 (d, 1H); MS (m/z): 388.41 (M+1)$^+$;

HPN-01224: 3-(6-amino-5-carbamoyl-4'-sulfamoyl-[1,1'-biphenyl]-3-yl)prop-2-yn-1-yl butyrate Yield: 45%; $^1$H NMR: (300 MHz, CDCl$_3$) δ: 0.90 (t, 3H), 1.79 (M, 2H), 2.0 (s, 2H), 2.32 (t, 2H), 4.82 (s, 2H), 6.27 (s, 2H), 7.50 (s, 2H), 7.64 (d, 2H), 7.88-7.92 (dd, 4H), 8.10 (d, 1H); MS (m/z): 416.46 (M+1)$^+$;

Example 20. Synthesis of the HPN-013 Series of HPN-01 Derivatives

A third series of HPN-01 derivatives were produced using the following synthetic process:

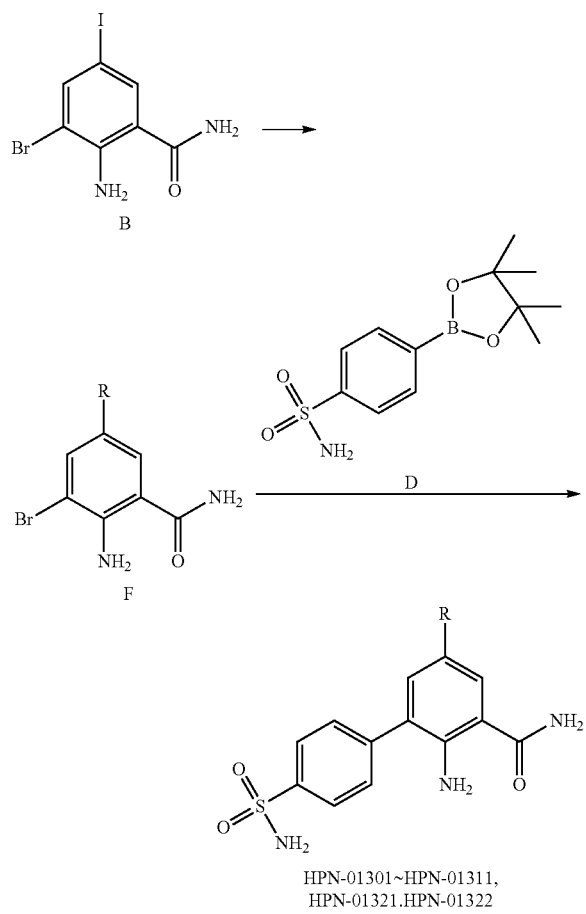

HPN-01301~HPN-01311,
HPN-01321.HPN-01322

The details of this synthesis are as follows:

Step 1. Synthesis of Compound F 1.2 g of Compound B (3 mmol), substituted phenylboronic acid/substituted cycloalkylboronic acid/substituted heteroarylboronic acid (3.3 mmol), 0.3 g PdCl2(Ph3P)$_2$ (3%), and 1.95 g casium carbonate (CsCO3) (6 mmol) were added to 50 mL of THF/water mixed solvent (THF:H2O=30 mL: 20 mL) and heated to reflux for 24 hours under nitrogen protection. The reaction was stopped, and the reaction solution was poured into 200 mL ice water and stirred continuously. Precipitated solids were collected, dried, and subjected to silica gel column chromatography purification, resulting in isolation of Compound F. The yield of Compound F was 20 to 75%.

Step 2. Synthesis of HPN-013 Series Compounds 10 mmol of Compound F, 4.2 g 4.2 g of Compound D (15 mmol), 0.35 g PdCl2(PPh3)$_2$ (5%), and 2.8 g potassium carbonate (20 mmol) were dissolved in a mixture of 50 ml dioxane and 20 mL water, and the reaction mixture was incubated at 80° C. for 30 hours under nitrogen protection. After the reaction was completed, the reaction solution was poured into ice water and stirred vigorously. The solids were collected, dried, and subjected to silica gel column chromatography purification, resulting in isolation of Compounds HPN-01301 to HPN-01311, HPN-01321, and HPN-01322. The structural information of these compounds are as follows:

HPN-01301: methyl 4'-amino-5'-carbamoyl-4"-sulfamoyl-[1,1':3',1"-terphenyl]-4-carboxylate Yield: 61%; $^1$H NMR: (300 MHz, CDCl$_3$) δ: 2.0 (s, 2H), 3.89 (s, 3H), 6.27 (s, 2H), 7.5 (s, 2H), 7.70~7.75 (m, 3H), 7.88-7.94 (m, 6H), 8.31 (s, 1H); MS (m/z): 426.46 (M+1)$^+$;

HPN-01302: ethyl 4'-amino-5'-carbamoyl-4"-sulfamoyl-[1,1':3',1"-terphenyl]-4-carboxylate Yield: 60%; $^1$H NMR: (300 MHz, CDCl$_3$) δ: 1.29 (t, 3H), 2.0 (s, 2H), 4.30 (dd, 2H), 6.27 (s, 2H), 7.50 (s, 2H), 7.70-7.75 (t, 3H), 7.88-7.94 (m, 6H), 8.31 (s, 1H); MS (m/z): 440.48 (M+1)$^+$;

HPN-01303: isopropyl 4'-amino-5'-carbamoyl-4"-sulfamoyl-[1,1':3',1"-terphenyl]-4-carboxylate Yield: 57%; $^1$H NMR: (300 MHz, CDCl$_3$) δ: 1.32 (d, 6H), 2.0 (s, 2H), 5.24 (m, 1H), 6.27 (s, 2H), 7.70-7.75 (t, 3H), 7.88-7.96 (m, 6H), 8.31 (s, 1H); MS (m/z): 454.51 (M+1)$^+$;

HPN-01304: 4'-amino-5'-carbamoyl-4"-sulfamoyl-[1,1':3',1"-terphenyl]-4-yl acetate Yield: 64%; $^1$H NMR: (300 MHz, CDCl$_3$) δ: 2.0 (s, 2H), 2.28 (s, 3H), 6.27 (s, 2H), 7.15 (d, 2H), 7.50 (s, 2H), 7.70-7.76 (t, 3H), 7.88-7.92 (dd, 4H), 8.31 (s, 1H); MS (m/z): 426.46 (M+1)$^+$;

HPN-01305: 4'-amino-5'-carbamoyl-4"-sulfamoyl-[1,1':3',1"-terphenyl]-4-yl propionate Yield: 71%; $^1$H NMR: (300 MHz, CDCl$_3$) δ: 1.09 (t, 3H), 2.0 (s, 2H), 2.27 (dd, 2H), 6.27 (s, 2H), 7.15 (d, 2H), 7.50 (s, 2H), 7.70-7.76 (t, 3H), 7.88-7.92 (dd, 4H), 8.31 (s, 1H); MS (m/z): 455.48 (M+1)$^+$;

HPN-01306: 4'-amino-5'-carbamoyl-4"-sulfamoyl-[1,1':3',1"-terphenyl]-4-yl butyrate Yield: 65%; $^1$H NMR: (300 MHz, CDCl$_3$) δ: 0.90 (t, 3H), 1.67 (m, 2H), 2.0 (s, 2H), 2.59 (t, 2H), 6.27 (s, 2H), 7.15 (d, 2H), 7.50 (s, 2H), 7.70-7.76 (t, 3H), 7.88-7.92 (dd, 4H), 8.31 (s, 1H); MS (m/z): 454.51 (M+1)$^+$;

HPN-01307: 2-amino-5-(6-chloropyridin-3-yl)-4'-sulfamoyl-[1,1'-biphenyl]-3-carboxamide Yield: 66%; $^1$H NMR: (300 MHz, CDCl$_3$) δ: 2.0 (s, 2H), 6.27 (S, 2H), 7.36 (d, 1H), 7.50 (s, 2H), 7.70 (s, 1H), 7.88-7.92 (dd, 4H), 8.26-8.31 (dd, 2H), 9.01 (s, 1H); MS (m/z): 403.85 (M+1)$^+$;

HPN-01308: 2-amino-5-(5-chloropyridin-2-yl)-4'-sulfamoyl-[1,1'-biphenyl]-3-carboxamide Yield: 68%; $^1$H NMR: (300 MHz, CDCl$_3$) δ: 2.0 (s, 2H), 6.27 (s, 2H), 7.50 (s, 2H), 7.58 (d, 3H), 7.88-7.92 (dd, 4H), 8.16-8.21 (t, 2H), 8.49 (s, 1H), 8.82 (s, 1H); MS (m/z): 403.85 (M+1)$^+$;

HPN-01309: 2-amino-5-(4-chloro-1H-pyrrol-2-yl)-4'-sulfamoyl-[1,1'-biphenyl]-3-carboxamide Yield: 77%; $^1$H NMR: (300 MHz, CDCl$_3$) δ: 2.0 (s, 2H), 5.0 (s, 1H), 6.27 (s, 2H), 6.40 (s, 6.40), 6.95 (s, 1H), 7.50 (s, 2H), 7.70 (s, 1H), 7.88-7.92 (dd, 4H), 8.31 (s, 1H); MS (m/z): 391.84 (M+1)$^+$;

HPN-01310: 2-amino-5-(5-chloro-1H-pyrrol-3-yl)-4'-sulfamoyl-[1,1'-biphenyl]-3-carboxamide Yield: 55%; $^1$H NMR: (300 MHz, CDCl$_3$) δ: 2.0 (s, 2H), 5.0 (s, 1H), 6.27 (s, 2H), 6.40 (s, 1H), 6.95 (s, 1H), 7.50 (s, 2H), 7.70 (s, 1H), 7.88-7.92 (dd, 4H), 8.31 (s, 1H), 7.70 (s, 1H), 7.88-7.92 (dd, 4H), 8.31 (s, 1H); MS (m/z): 391.84 (M+1)$^+$;

HPN-01311: 2-amino-5-(5-bromo-1H-pyrrol-3-yl)-4'-sulfamoyl-[1,1'-biphenyl]-3-carboxamide Yield: 61%; $^1$H NMR: (300 MHz, CDCl$_3$) δ: 2.0 (s, 2H), 5.0 (s, 1H), 6.27 (s, 2H), 6.40 (s, 1H), 6.95 (s, 1H), 7.50 (s, 2H), 7.70 (s, 1H), 7.88-7.92 (dd, 4H), 8.31 (s, 1H); MS (m/z): 436.29 (M+1)$^+$;

HPN-01321: 2-amino-5-(3-bromocyclopentyl)-4'-sulfamoyl-[1,1'-biphenyl]-3-carboxamide Yield: 59%; $^1$H NMR: (300 MHz, CDCl$_3$) δ: 1.93 (m, 4H), 1.68-3.45 (m, 10H), 2.79 (m, 1H), 3.45 (m, 1H), 6.27 (s, 2H), 7.50 (m, 2H), 7.86-7.92 (m, 5H); MS (m/z): 439.34 (M+1)$^+$;

HPN-01322: 2-amino-5-(4-bromocyclohexyl)-4'-sulfamoyl-[1,1'-biphenyl]-3-carboxamide Yield: 70%; $^1$H NMR: (300 MHz, CDCl$_3$) δ: 1.61-1.86 (m, 4H), 1.61-2.02 (m, 6H), 2, 72 (m, 5H), 3.38 (m, 1H), 6.27 (s, 2H), 7.50-7.72 (t, 3H), 7.86-7.92 (m, 5H); MS (m/z): 453.37 (M+1)$^+$;

Example 21. Synthesis of Additional HPN-013 Series Compounds

Additional HPN-013 series of compounds were synthesized using the following process:

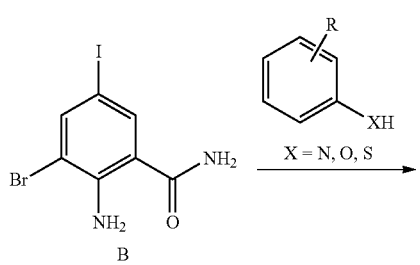

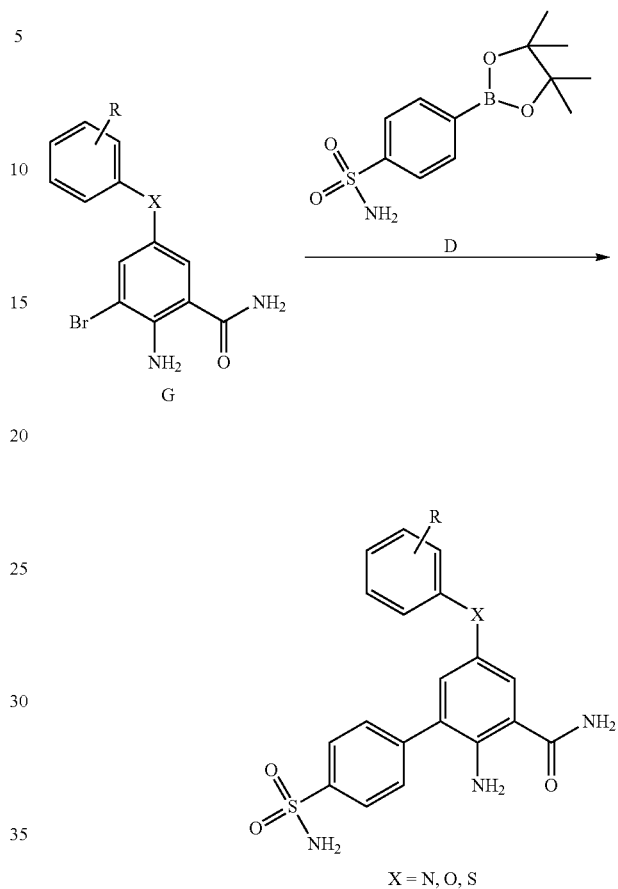

The details of this synthesis are as follows:

Step 1. Synthesis of Compound G 1.2 g Compound B (3 mmol), substituted aniline/substituted phenol/substituted thiophenol (3.3 mmol), and 0.5 g K$_2$CO$_3$ (3.3 mmol) were added to DMF and reacted at room temperature for 16 hours under nitrogen protection. The reaction was stopped, and the reaction solution was poured into 200 mL of ice water. The precipitated solids were collected, dried, and subjected to silica gel column chromatography, resulting in isolation of Compound G. The yield of Compound G was 68 to 79%.

Step 2. Synthesis of HPN-013 Series Compounds 10 mmol of Compound G, 4.2 g Compound D (15 mmol), 0.35 g PdCl$_2$(PPh$_3$)$_2$ (5%) and 2.8 g potassium carbonate (20 mmol) were dissolved in a mixture of 50 mL dioxane and 20 mL water, and the reaction mixture was incubated at 80° C. for 30 hours under nitrogen protection. After the reaction was completed, the reaction solution was poured into ice water and stirred vigorously. The solids were collected, dried, and subjected to silica gel column chromatography, resulting in isolation of Compounds HPN-01312 to HPN-01320. The structural information of these compounds is as follows:

HPN-01312: 2-amino-5-((4-chlorophenyl)amino)-4'-sulfamoyl-[1,1'-biphenyl]-3-carboxamide Yield: 77%; $^1$H NMR: (300 MHz, CDCl$_3$) δ: 2.0 (s, 2H), 4.0 (s, 1H), 6.27 (s, 2H), 6.80 (d, 2H), 7.24 (d, 2H), 7.50 (s, 2H), 7.66 (d, 2H), 7.88-7.92 (dd, 4H); MS (m/z): 417.88 (M+1)$^+$;

HPN-01313: 2-amino-5-(4-chlorophenoxy)-4'-sulfamoyl-[1,1'-biphenyl]-3-carboxamide Yield: 65%; $^1$H NMR: (300 MHz, CDCl$_3$) δ: 2.0 (s, 2H), 6.27 (s, 2H), 7.44-7.57 (m, 8H), 7.88-7.92 (dd, 4H); MS (m/z): 418.87 (M+1)$^+$;

HPN-01314: 2-amino-5-((4-chlorophenyl)thio)-4'-sulfamoyl-[1,1'-biphenyl]-3-carboxamide Yield: 64%; $^1$H NMR: (300 MHz, CDCl$_3$) δ: 2.0 (s, 2H), 6.27 (s, 2H), 7.27-7.50 (t, 6H), 7.42-7.50 (d, 2H), 7.76 (d, 2H), 7.88-7.92 (dd, 4H); MS (m/z): 434.93 (M+1)$^+$;

HPN-01315: 2-amino-5-((3-chlorophenyl)amino)-4'-sulfamoyl-[1,1'-biphenyl]-3-carboxamide Yield: 54%; $^1$H NMR: (300 MHz, CDCl$_3$) δ: 2.0 (s, 2H), 4.0 (s, 1H), 6.27 (s, 2H), 6.81-6.89 (m, 3H), 7.14 (t, 1H), 7.50-7.51 (d, 3H), 7.88-7.92 (dd, 4H); MS (m/z): 417.88 (M+1)$^+$;

HPN-01316: 2-amino-5-(3-chlorophenoxy)-4'-sulfamoyl-[1,1'-biphenyl]-3-carboxamide Yield: 45%; $^1$H NMR: (300 MHz, CDCl$_3$) δ: 2.0 (s, 2H), 6.27 (s, 2H), 7.02 (m, 1H), 7.21 (m, 1H) 7.34-7.35 (m, 2H), 7.44-7.51 (m, 5H), 7.88-7.92 (dd, 4H); MS (m/z): 418.87 (M+1)$^+$;

HPN-01317: 3-((6-amino-5-carbamoyl-4'-sulfamoyl-[1,1'-biphenyl]-3-yl)amino)benzoic Acid Yield: 65%; $^1$H NMR: (300 MHz, CDCl$_3$) δ: 2.0 (s, 2H), 4.0 (s, 1H), 6.27 (s, 2H), 6.80 (d, 2H), 6.89 (d, 2H), 7.27 (m, 1H), 7.41-7.57 (m, 4H), 7.88-7.97 (m, 5H), 11.0 (s, 1H); MS (m/z): 427.45 (M+1)$^+$;

HPN-01318: 3-((6-amino-5-carbamoyl-4'-sulfamoyl-[1,1'-biphenyl]-3-yl)oxy)benzoic Acid Yield: 69%; 1H NMR: (300 MHz, CDCl$_3$) δ: 2.0 (s, 2H), 6.27 (s, 2H), 7.44-7.51 (m, 5H), 7.88-7.93 (m, 7H), 11.0 (s, 1H); MS (m/z): 428.43 (M+1)$^+$;

HPN-01319: methyl 3-((6-amino-5-carbamoyl-4'-sulfamoyl-[1,1'-biphenyl]-3-yl)amino)benzoate Yield: 55%; $^1$H NMR: (300 MHz, CDCl$_3$) δ: 2.0 (s, 2H), 3.89 (s, 4H), 4.0 (s, 1H), 6.27 (s, 2H), 6.80 (d, 2H) 6.89 (d, 2H), 7.11 (t, 1H), 7.31 (m, 2H), 7.41-7.50 (m, 3H), 7.84-7.92 (m, 8H); MS (m/z): 441.47 (M+1)$^+$;

HPN-01320: methyl 3-((6-amino-5-carbamoyl-4'-sulfamoyl-[1,1'-biphenyl]-3-yl)oxy)benzoate Yield: 57%; $^1$H NMR: (300 MHz, CDCl$_3$) δ: 2.0 (s, 2H), 3.89 (s, 4H), 6.27 (s, 2H), 7.35 (m, 2H) 7.44-7.51 (m, 5H), 7.75-7.92 (m, 6H); MS (m/z): 442.46 (M+1)$^+$;

Example 22. Synthesis of HPN-014 Series Compounds

Additional HPN-01 derivatives were synthesized using the following process:

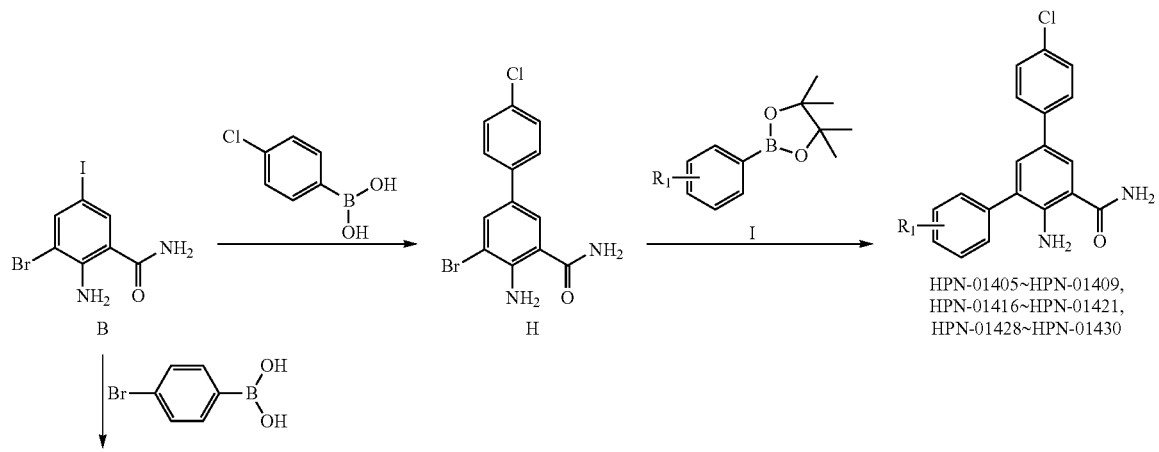

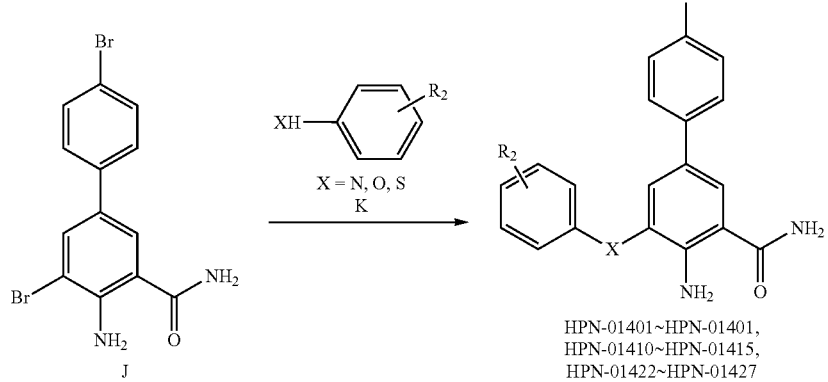

Details of this synthesis are as follows:

Step 1. Synthesis of Compound H 1.2 g Compound B (3 mmol), 0.553 g p-chlorophenylboronic acid (3.3 mmol), 0.03 g PdCl$_2$(Ph$_3$P)$_2$ (3%) and 1.95 g CsCO$_3$ (6 mmol) were added to a THF/water mixed solvent (THF:H2O=30 mL:20 mL) and heated to reflux for 24 hours under nitrogen protection. The reaction was stopped, and the reaction solution was poured into 200 mL ice water and stirred continuously. The precipitated solids were collected, dried, and subjected to silica gel column chromatography, resulting in isolation of Compound H. The yield of Compound H was 78%.

Step 2. Synthesis of HPN-01406 Compound 3.25 g Compound H (10 mmol), 3.93 g 4-tetramethyldioxaborolyl urea (15 mmol), 0.35 g PdCl2(PPh3)2 (5%) and 2.8 g potassium carbonate (20 mmol) were dissolved in and mixture of 50 ml dioxane and 20 ml water, and the mixture incubated at 80° C. for 30 hours under nitrogen protection. After the reaction was completed, the reaction solution was poured into ice water and stirred vigorously. The solids were collected, dried, and subjected to silica gel column chromatography, resulting in isolation of Compound HPN-01406. The yield of Compound HPN-01406 was 45%. Structural information for this compound is as follows: 1H NMR: (300 MHz, CDCl3) δ: 6.0 (s, 3H), 6.27 (s, 2H), 7.50-7.55 (t, 4H), 7.70-7.77 (m, 4H), 7.87 (d, 4H), 8.10 (d, 2H), 8.31 (s, 1H); MS (m/z): 381.83 (M+1)+$_o$

Step 3. Synthesis of Compound J 1.2 g of Compound B (3 mmol), 0.66 g p-bromophenylboronic acid (3.3 mmol), 0.03 g PdCl2(Ph3P)$_2$ (3%) and 1.95 g CsCO3 (6 mmol) were added to a THF/water mixed solvent. (THF:H2O=30 mL:20 mL) and heated to reflux for 24 hours under nitrogen protection. The reaction was stopped, the reaction solution was poured into 200 mL ice water and stirred continuously. The precipitated solids were collected, dried, and subjected to silica gel column chromatography, resulting in isolation of Compound J. The yield of Compound J was 69%.

Step 4. Synthesis of Compound HPN-01401

3.67 g of Compound J (10 mmol), 2.6 g 4-hydroxybenzenesulfonamide (15 mmol) and 2.8 g potassium carbonate (20 mmol) were dissolved in 50 mL of DMF and reacted at 60° C. for 24 hours under nitrogen protection. After the reaction was completed, the reaction solution was poured into ice water and stirred vigorously. The solids were collected, dried, and subjected to silica gel column chromatography, resulting in isolation of Compound HPN-01401. The yield of Compound HPN-01401 was 75%. Structural information for this compound is as follows: 1H NMR: (300 MHz, CDCl3) S: 2.0 (s, 2H), 6.27 (s, 2H), 7.35 (d, 2H), 7.50-7.55 (m, 5H), 7.71 (d, 2H), 8.07-8.10 (t, 3H); MS (m/z): 418.87 (M+1)+$_o$ The HPN-014 series compounds were synthesized using Step 2 and Step 4 respectively. The structural information of the HPN-014 series compounds is as follows:

HPN-01402: 4-amino-4'-chloro-5-((4-sulfamoylphenyl)amino)-[1,1'-biphenyl]-3-carboxamide Yield: 51%; $^1$H NMR: (300 MHz, CDCl$_3$) δ: 2.0 (s, 2H), 4.0 (s, 1H), 6.27 (s, 2H), 6.89 (s, 1H), 7.24 (d, 2H), 7.50-7.61 (m, 6H), 8.10 (d, 2H); MS (m/z): 417.88 (M+1)$^+$;

HPN-01403: 4-amino-4'-chloro-5-((4-sulfamoylphenyl)thio)-[1,1'-biphenyl]-3-carboxamide Yield: 44%; $^1$H NMR: (300 MHz, CDCl$_3$) δ: 2.0 (s, 2H), 6.27 (s, 2H), 7.50-7.55 (m, 5H), 7.66-7.69 (dd, 4H), 8.09-8.10 (t, 3H); MS (m/z): 434.93 (M+1)$^+$;

HPN-01404: 4-amino-4'-bromo-5-((4-sulfamoylphenyl)amino)-[1,1'-biphenyl]-3-carboxamide Yield: 50%; $^1$H NMR: (300 MHz, CDCl$_3$) δ: 2.0 (s, 2H), 4.0 (s, 1H), 6.27 (s, 2H), 6.89 (s, 1H), 7.24 (d, 2H), 7.50-7.71 (m, 9H); MS (m/z): 462.33 (M+1)$^+$;

HPN-01405: 6'-amino-5'-carbamoyl-4"-chloro-[1,1': 3',1"-terphenyl]-4-yl Dihydrogen Phosphate Yield: 45%; $^1$H NMR: (300 MHz, CDCl$_3$) δ: 6.27 (s, 2H), 7.01 (d, 2H), 7.507.70 (m, 8H), 8.10 (d, 2H), 8.31 (s, 1H); MS (m/z): 419.77 (M+1)$^+$;

HPN-01407: 4"-acetamido-4'-amino-4-chloro-[1,1': 3',1"-terphenyl]-5'-carboxamide Yield: 45%; $^1$H NMR: (300 MHz, CDCl$_3$) δ: 2.04 (s, 3H), 6.27 (s, 2H), 7.23 (s, 1H), 7.50-7.55 (t, 4H), 7.70-7.77 (m, 4H), 7.87 (d, 4H), 8.10 (d, 2H), 8.31 (s, 1H); MS (m/z): 380.84 (M+1)$^+$;

HPN-01408: 4'-amino-4-chloro-4"-propionamido-[1,1':3',1"-terphenyl]-5'-carboxamide Yield: 38%; ¹H NMR: (300 MHz, CDCl₃) δ: 1.02 (dd, 3H), 2.45 (dd, 2H), 6.27 (s, 2H), 7.23 (s, 1H), 7.50-7.55 (t, 4H), 7.70-7.87 (m, 6H), 8.10 (d, 2H), 8.31 (s, 1H); MS (m/z): 394.87 (M+1)⁺;

HPN-01409: 4'-amino-4"-butyramido-4-chloro-[1,1':3',1"-terphenyl]-5'-carboxamide Yield: 47%; ¹H NMR: (300 MHz, CDCl₃) δ: 0.90 (t, 3H), 1.78 (m, 2H), 2.39 (t, 2H), 6.27 (s, 2H), 7.23 (s, 1H), 7.50-7.55 (t, 4H), 7.70-7.87 (m, 6H), 8.10 (d, 2H), 8.31 (s, 1H); MS (m/z): 408.89 (M+1)⁺;

HPN-01410: 5-(3-(2H-tetrazol-5-yl)phenoxy)-4-amino-4'-chloro-[1,1'-biphenyl]-3-carboxamide Yield: 50%; ¹H NMR: (300 MHz, CDCl₃) δ: 6.27 (s, 2H), 7.10 (m, 1H), 7.47-7.55 (m, 6H), 8.0 (m, 4H), 8.07-8.10 (m, 3H); MS (m/z): 407.83 (M+1)⁺;

HPN-01411: 4-amino-4'-chloro-5-(3-(N-propylsulfamoyl)phenoxy)-[1,1'-biphenyl]-3-carboxamide Yield: 57%; ¹H NMR: (300 MHz, CDCl₃) δ: 0.90 (t, 3H), 1.60 (m, 2H), 3.38 (t, 2H), 6.27 (s, 2H), 7.14 (d, 1H), 7.50-7.55 (m, 4H), 7.69-7.71 (t, 4H), 8.07-8.10 (m, 3H); MS (m/z): 460.95 (M+1)⁺;

HPN-01412: 4-amino-4'-chloro-5-(3-sulfamoylphenoxy)-[1,1'-biphenyl]-3-carboxamide Yield: 48%; ¹H NMR: (300 MHz, CDCl₃) δ: 2.0 (s, 2H), 6.27 (s, 2H), 7.14 (d, 1H), 7.50-7.55 (m, 5H), 7.69-7.71 (t, 4H), 8.07-8.10 (m, 3H); MS (m/z): 418.87 (M+1)⁺;

HPN-01413: 4-amino-4'-chloro-5-((3-sulfamoylphenyl)amino)-[1,1'-biphenyl]-3-carboxamide Yield: 47%; ¹H NMR: (300 MHz, CDCl₃) δ: 2.0 (s, 2H), 4, 0 (s, 1H), 6.27 (s, 2H), 6.89 (s, 1H), 7.12 (s, 2H), 7.22 (d, 2H), 7.48-7.63 (m, 6H), 7.71 (d, 1H), 8.10 (d, 2H); MS (m/z): 417.88 (M+1)⁺;

HPN-01414: 4-amino-4'-chloro-5-((3-sulfamoylphenyl)thio)-[1,1'-biphenyl]-3-carboxamide Yield: 37%; ¹H NMR: (300 MHz, CDCl₃) δ: 2.0 (s, 2H), 6.27 (s, 2H), 7.41-7.60 (m, 8H), 7.87 (s, 1H), 8.09-8.10 (t, 3H); MS (m/z): 434.93 (M+1)⁺;

HPN-01415: 4-amino-4'-bromo-5-(3-sulfamoylphenoxy)-[1, 1'-biphenyl]-3-carboxamide Yield: 56%; ¹H NMR: (300 MHz, CDCl₃) δ: 2.0 (s, 2H), 6.27 (s, 2H), 6.89 (s, 1H), 7.12 (s, 2H), 7.22 (s, 2H), 7.48-7.66 (m, 8H); MS (m/z): 463.32 (M+1)⁺;

HPN-014016: 6'-amino-4"-bromo-5'-carbamoyl-[1,1':3',1"-terphenyl]-4-yl dihydrogen phosphate Yield: 49%; ¹H NMR: (300 MHz, CDCl₃) δ: 6.27 (s, 2H), 7.01 (d, 2H), 7.53-7.70 (m, 7H), 8.31 (s, 1H); MS (m/z): 464.22 (M+1)⁺;

HPN-01417: 4'-amino-4-chloro-4"-guanidino-[1,1':3',1"-terphenyl]-5'-carboxamide

Yield: 67%; ¹H NMR: (300 MHz, CDCl₃) δ: 4.0 (s, 1H), 6.27 (s, 1H), 6.69 (d, 2H), 7.50-7.55 (m, 6H), 8.10 (d, 2H), 8.31 (d, 1H), 8.56 (s, 2H); MS (m/z): 380.84 (M+1)⁺;

HPN-01418: 4'-amino-4-chloro-4"-thioureido-[1,1':3',1"-terphenyl]-5'-carboxamide Yield: 59%; ¹H NMR: (300 MHz, CDCl₃) δ: 4.0 (s, 1H), 6.27 (s, 1H), 6.69 (d, 2H), 7.50-7.55 (m, 6H), 8.10 (d, 2H), 8.31 (d, 1H), 8.56 (s, 2H); MS (m/z): 397.89 (M+1)⁺;

HPN-01419: 4'-amino-4-chloro-4"-(2-hydroxyacetamido)-[1,1':3',1"-terphenyl]-5'-carboxamide Yield: 56%; ¹H NMR: (300 MHz, CDCl₃) δ: 3.65 (s, 1H), 4.47 (s, 2H), 6.27 (s, 2H), 7.23 (s, 1H), 7.50-7.55 (t, 4H), 7.70-7.87 (m, 5H), 8.10 (d, 2H), 8.31 (d, 1H); MS (m/z): 396.84 (M+1)⁺;

HPN-01420: 4'-amino-4-chloro-4"-(2-oxo-2,5-dihydro-1H-imidazol-1-yl)-[1,1':3',1"-terphenyl]-5'-carboxamide Yield: 68%; ¹H NMR: (300 MHz, CDCl₃) δ: 3.02 (d, 2H), 6.27 (s, 2H), 7.50-7.55 (m, 6H), 7.70-7.77 (m, 3H), 7, 87 (m, 5H), 8.10 (d, 2H), 8.31 (d, 1H); MS (m/z): 405.85 (M+1)⁺;

HPN-01421: 4'-amino-4-chloro-4"-(1H-1,2,3-triazol-4-yl)-[1,1':3',1"-terphenyl]-5'-carboxamide Yield: 58%; ¹H NMR: (300 MHz, CDCl₃) δ: 6.27 (s, 2H), 7.25 (d, 2H), 7.50-7.55 (m, 4H), 7.70-7.75 (d, 2H), 8.10 (d, 2H), 8.30-8.31 (d, 3H), 12.0 (s, 1H); MS (m/z): 390.84 (M+1)⁺;

HPN-01422: 4-amino-4'-chloro-5-(3-(N-(2-hydroxyethyl)sulfamoyl)phenoxy)-[1, 1'-biphenyl]-3-carboxamide Yield: 58%; ¹H NMR: (300 MHz, CDCl₃) δ: 3.44-3.49 (m, 4H), 3.65 (s, 1H), 6.27 (s, 2H), 7.14 (s, 1H), 7.50-7.58 (m, 6H), 7.69-7.71 (m, 3H), 8.07-8.10 (t, 3H); MS (m/z): 462.92 (M+1)⁺;

HPN-01423: 4-amino-4'-chloro-5-(4-sulfamoylphenethoxy)-[1,1'-biphenyl]-3-carboxamide Yield: 48%; ¹H NMR: (300 MHz, CDCl₃) δ: 3.11 (t, 2H), 4.27 (t, 2H), 6.62 (s, 2H), 7.23 (s, 2H), 7.5~7.61 (m, 2H), 6.62 (d, 2H), 7.77 (d, 2H), 7.90 (s, 2H), 8.10-8.13 (m, 3H); MS (m/z): 446.92 (M+1)⁺;

HPN-01424: 4-amino-4'-chloro-5-((4-sulfamoylbenzyl)oxy)-[1,1'-biphenyl]-3-carboxamide Yield: 52%; ¹H NMR: (300 MHz, CDCl₃) δ: 5.16 (s, 2H), 6.62 (s, 2H), 7.23 (s, 2H), 7.39 (d, 1H), 7.53 (d, 2H), 7.62 (d, 2H), 7.76 (d, 2H), 7.90 (s, 2H), 8.10-8.13 (m, 3H), MS (m/z): 432.89 (M+1)⁺;

HPN-01425: 4-amino-4'-chloro-5-((4-sulfamoylphenethyl)amino)-[1,1'-biphenyl]-3-carboxamide Yield: 55%; ¹H NMR: (300 MHz, CDCl₃) δ: 2.93 (t, 2H), 3.40 (t, 2H), 4.80 (s, 2H), 6.79 (s, 2H), 6.86 (d, 1H), 7.23 (s, 2H), 7.45 (d, 2H), 7.62 (d, 2H), 7.79-7.87 (m, 3H), 7.90 (s, 2H), 8.10 (d, 2H), MS (m/z): 445.93 (M+1)+;

HPN-01426: 4-amino-4'-chloro-5-((4-sulfamoylbenzyl)amino)-[1,1'-biphenyl]-3-carboxamide Yield: 47%; $^1$H NMR: (300 MHz, CDCl$_3$) δ: 4.32 (s, 2H), 4.82 (s, 2H), 6.81 (s, 1H), 6.86 (d, 1H), 7.23 (s, 2H), 7.53-7.62 (m, 4H), 7.76-7.80 (m, 3H), 7.93 (s, 2H), 8.10 (d, 2H), MS (m/z): 431.91 (M+1)+;

HPN-01427: 4-amino-4'-chloro-5-(4-sulfamoylpiperazin-1-yl)-[1,1'-biphenyl]-3-carboxamide Yield: 53%; $^1$H NMR: (300 MHz, CDCl$_3$) δ: 2.58 (t, 4H), 3.19 (t, 4H), 4.82 (s, 2H), 5.5 (s, 2H), 6.92 (d, 1H), 7.62 (d, 2H), 7.80 (d, 1H), 7.90 (s, 2H), 8.12 (d, 2H), MS (m/z): 410.89 (M+1)+;

HPN-01428: 4-amino-4'-chloro-5-(5-sulfamoylpyridin-2-yl)-[1,1'-biphenyl]-3-carboxamide Yield: 51%; $^1$H NMR: (300 MHz, CDCl$_3$) δ: 6.62 (s, 2H), 7.55 (s, 2H), 7.66 (d, 2H), 7.90 (s, 2H), 8.1-8.2 (m, 4H), 8.43 (d, 1H), 8.55 (d, 1H), 8.72 (d, 1H), MS (m/z): 403.85 (M+1)+;

HPN-01429: 4'-amino-4-chloro-4"-(3-(pyridin-3-yl)ureido)-[1,1':3',1"-terphenyl]-5'-carboxamide Yield: 49%; $^1$H NMR: (300 MHz, CDCl$_3$) δ: 5.02 (s, 2H), 7.4 (m, 1H), 7.76-7.85 (m, 4H), 7.95~8.03 (m, 4H), 8.10-8.15 (m, 1H), 8.33 (m, 3H), 8.55 (d, 1H), 8.93 (s, 1H), 9.30 (s, 1H), MS (m/z): 458.92 (M+1)+;

HPN-01430: 4'-amino-4-chloro-4"-(3-isopropylureido)-[1,1':3',1"-terphenyl]-5'-carboxamide Yield: 68%; $^1$H NMR: (300 MHz, CDCl$_3$) δ: 1.20 (d, 6H), 4.18 (m, 1H), 5.02 (s, 2H), 6.51 (s, 1H), 7.62 (d, 2H), 7.80 (d, 2H), 7.90 (s, 2H), 8.10 (m, 3H), 8.26 (s, 1H), 8.55 (d, 1H), MS (m/z): 423.91 (M+1)+;

Example 23. Synthesis of HPN-015 Series Compounds

Additional HPN-01 derivatives were synthesized using the following process:

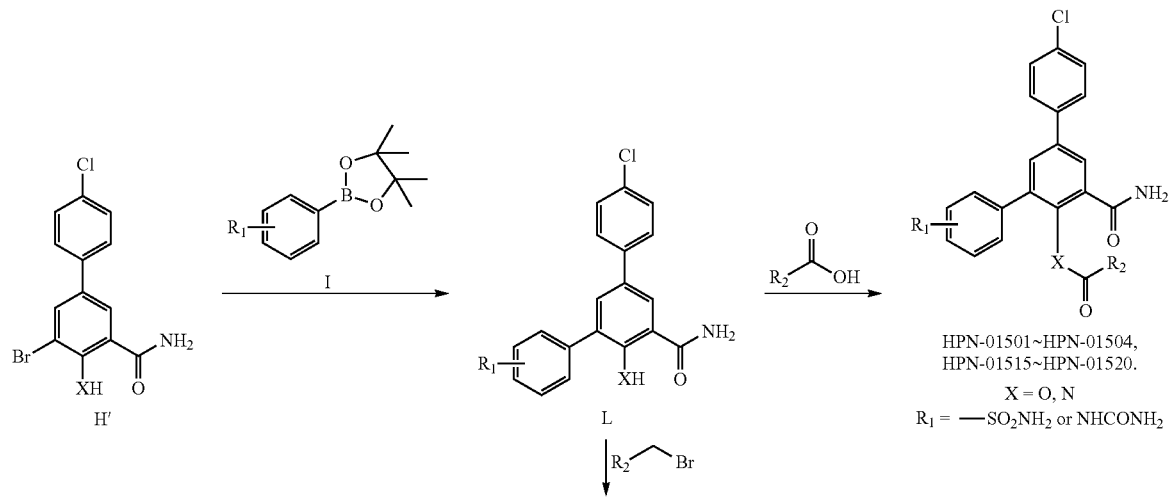

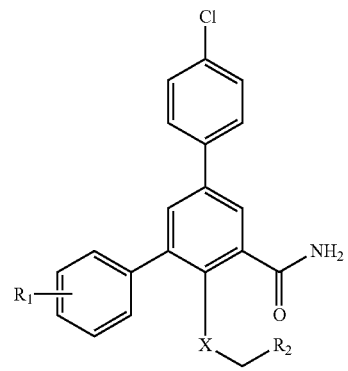

HPN-01531~HPN-01534

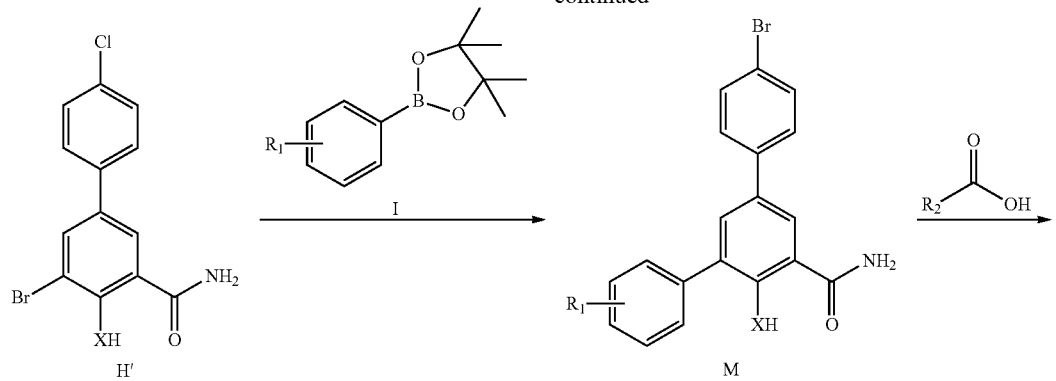

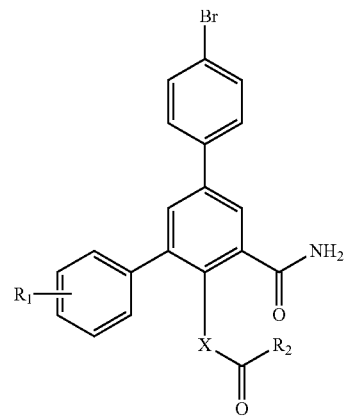

HPN-01513~HPN-01514,
HPN-01525~HPN-01527,
HPN-01529~HPN-01530

X = O, N
$R_1$ = —$SO_2NH_2$ or $NHCONH_2$

Details of the synthesis are as follows:

Step 1. Synthesis of Compounds L & M 10 mmol of Compound H' or J', 15 mmol substituted 4-tetramethyldioxaborolidine, 0.35 g $PdCl_2(PPh_3)_2$ (5%) and 2.8 g potassium carbonate (20 mmol) were dissolved in a mixture of 80 mL dioxane and 30 mL water, and reacted at 80° C. for 30 hours under nitrogen protection. After the reaction was completed, the reaction solution was poured into ice water and stirred vigorously. The solids were collected, dried, and subjected to silica gel column chromatography, resulting in isolation of Compounds L & M. The yield of Compounds L & M was 65-70%.

Step 2. Synthesis of HPN-015 Series Compounds 10 mmol of Compound L & M (10 mmol), 15 mmol substituted alkyl carboxylic acid, dissolved in 50 mL of acetonitrile, 8.8 g BOP (20 mmol) and 3.87 g DIEA (30 mmol) were reacted at 30° C. for 30 hours under nitrogen protection. After the reaction was completed, the reaction solution was poured into ice water and extracted with 20 mL ethyl acetate three times, and the organic phase was washed with acid water, basic water, and saturated saline in that order. HPN-015 series compounds were isolated by silica gel column chromatography purification. The structural information of the HPN-015 series compounds is as follows:

HPN-01501: 4'-acetamido-4-chloro-4"-sulfamoyl-[1,1':3',1"-terphenyl]-5'-carboxamide Yield: 68%; $^1$H NMR: (300 MHz, $CDCl_3$) δ: 2.0-2.04 (d, 5H), 7.23 (s, 1H), 7.50-7.55 (t, 4H), 7.88-7.93 (m, 5H), 8.10 (d, 2H), 8.54 (s, 1H); MS (m/z): 444.9 $(M+1)^+$;

HPN-01502: 4-chloro-4'-(2-hydroxyacetamido)-4"-sulfamoyl-[1,1':3',1"-terphenyl]-5'-carboxamide Yield: 65%; $^1$H NMR: (300 MHz, $CDCl_3$) δ: 2.0 (s, 2H), 3.65 (s, 1H), 4.47 (s, 2H), 7.23 s, 1H), 7.50-7.55 (t, 4H), 7.88-7.93 (m, 5H), 8.10 (d, 2H), 8.54 (s, 1H); MS (m/z): 460.9 $(M+1)^+$;

HPN-01503: 4-chloro-4'-(cyclopropanecarboxamido)-4"-sulfamoyl-[1,1':3',1"-terphenyl]-5'-carboxamide Yield: 71%; $^1$H NMR: (300 MHz, $CDCl_3$) δ: 0.73-0.98 (dd, 4H) 1.16 (m, 1H), 2.0 (s, 2H), 7.23 (s, 1H), 7.50-7.55 (t, 4H), 7.88-7.93 (m, 5H), 8.10 (d, 2H), 8.54 (s, 1H); MS (m/z): 470.94 $(M+1)^+$;

HPN-01504: 4'-(2-aminoacetamido)-4-chloro-4"-sulfamoyl-[1,1':3',1"-terphenyl]-5'-carboxamide Yield: 57%; $^1$H NMR: (300 MHz, CDCl$_3$) δ: 1.53 (s, 2H), 2.0 (s, 2H), 3.85 (s, 2H), 7.23 (s, 1H), 7.50-7.55 (t, 4H), 7.88-7.93 (m, 5H) 8.10 (d, 2H), 8.54 (s, 1H); MS (m/z): 459.92 (M+1)$^+$;

HPN-01505: 4'-acetamido-4-chloro-4"-ureido-[1,1':3',1"-terphenyl]-5'-carboxamide Yield: 50%; $^1$H NMR: (300 MHz, CDCl$_3$) δ: 4.0 (s, 1H), 6.0 (s, 3H), 7.50-7.55 (t, 4H) 7.77-7.93 (m, 5H), 8.10 (d, 2H), 8.54 (s, 1H), 8.70 (s, 1H); MS (m/z): 408.83 (M+1)$^+$;

HPN-01506: 4-chloro-4'-(2-hydroxyacetamido)-4"-ureido-[1,1':3',1"-terphenyl]-5'-carboxamide Yield: 77%; $^1$H NMR: (300 MHz, CDCl$_3$) δ: 3.65 (s, 1H), 4.47 (s, 2H), 6.0 (d, 3H), 7.23 (s, 1H), 7.50-7.55 (t, 4H), 7.77-7.93 (m, 5H), 8.10 (d, 2H), 8.54 (s, 1H); MS (m/z): 439.86M+1)$^+$;

HPN-01513: 4-bromo-4'-(3-hydroxypropanamido)-4"-sulfamoyl-[1, 1':3',1"-terphenyl]-5'-carboxamide Yield: 69%; $^1$H NMR: (300 MHz, CDCl$_3$) δ: 2.0 (s, 2H), 2.42 (t, 2H), 3.65 (s, 1H), 3.91 (t, 2H), 7.23 (s, 1H), 7.50-7.53 (t, 4H) 7.66 (d, 2H), 7.88-7.93 (m, 6H), 8.54 (s, 1H); MS (m/z): 519.38 (M+1)$^+$;

HPN-01514: 4'-(3-aminopropanamido)-4-bromo-4"-sulfamoyl-[1,1':3',1"-terphenyl]-5'-carboxamide Yield: 47%; $^1$H NMR: (300 MHz, CDCl$_3$) δ: 2.0 (s, 2H), 2.71 (t, 2H), 3.03 (t, 2H) 5.11 (s, 2H), 7.23 (s, 1H), 7.50-7.53 (t, 4H) 7.66 (d, 2H), 7.88-7.93 (m, 6H), 8.54 (s, 1H); MS (m/z): 518.4 (M+1)$^+$;

HPN-01515: 4'-butyramido-4-chloro-4"-sulfamoyl-[1,1':3',1"-terphenyl]-5'-carboxamide Yield: 39%; $^1$H NMR: (300 MHz, CDCl$_3$) δ: 0.90 (t, 3H), 1.78 (m, 2H), 2.0 (s, 2H), 2.39 (t, 2H), 7.23 (s, 1H), 7.50-7.55 (t, 4H) 7.88-7.93 (m, 6H), 8.10 (d, 2H), 8.54 (s, 1H); MS (m/z): 488.96 (M+1)$^+$;

HPN-01516: 4-chloro-4'-(3-hydroxypropanamido)-4"-sulfamoyl-[1, 1':3',1"-terphenyl]-5'-carboxamide Yield: 53%; $^1$H NMR: (300 MHz, CDCl$_3$) δ: 2.0 (s, 2H), 2.42 (t, 2H), 3.65 (s, 1H), 3.91 (t, 2H), 7.23 (s, 1H), 7.50-7.55 (t, 4H), 7.88-7.93 (m, 6H), 8.10 (d, 2H), 8.54 (s, 1H); MS (m/z): 474.93 (M+1)$^+$;

HPN-01517: 4'-(3-aminopropanamido)-4-chloro-4"-sulfamoyl-[1, 1':3',1"-terphenyl]-5'-carboxamide Yield: 58%; $^1$H NMR: (300 MHz, CDCl$_3$) δ: 2.0 (s, 2H), 2.71 (t, 2H), 3.03 (t, 2H) 5.11 (s, 2H), 7.50-7.55 (t, 4H), 7.88-7.93 (m, 6H), 8.10 (d, 2H), 8.54 (s, 1H); MS (m/z): 473.94 (M+1)$^+$;

HPN-01518: 4'-(2-aminoacetamido)-4-chloro-4"-ureido-[1, 1':3',1"-terphenyl]-5'-carboxamide Yield: 67%; $^1$H NMR: (300 MHz, CDCl$_3$) δ: 1.53 (s, 2H), 3.85 (s, 2H), 6.0 (d, 3H), 7.23 (s, 1H), 7.50-7.55 (t, 4H), 8.10 (d, 2H), 8.54 (s, 1H); MS (m/z): 454.88 (M+1)$^+$;

HPN-01519: 4'-butyramido-4-chloro-4"-ureido-[1,1':3',1"-terphenyl]-5'-carboxamide Yield: 47%; $^1$H NMR: (300 MHz, CDCl$_3$) δ: 0.90 (t, 3H), 1.78 (m, 2H), 2.0 (s, 2H), 2.39 (t, 2H), 6.0 (s, 3H), 7.23 (s, 1H), 7.50-7.55 (t, 4H), 7.77-7.93 (m, 6H) 8.10 (d, 2H), 8.54 (s, 1H); MS (m/z): 451.92 (M+1)$^+$;

HPN-01520: 4-chloro-4'-(3-hydroxypropanamido)-4"-ureido-[1,1':3',1"-terphenyl]-5'-carboxamide Yield: 77%; $^1$H NMR: (300 MHz, CDCl$_3$) δ: 2.42 (t, 2H), 3.65 (s, 1H), 3.91 (s, 1H), 7.50-7.55 (t, 4H), 7.77-7.93 (m, 6H), 8.10 (d, 2H), 8.54 (s, 1H); MS (m/z): 453.89 (M+1)$^+$;

HPN-01525: 4-bromo-4'-(cyclopropanecarboxamido)-4"-sulfamoyl-[1,1':3',1"-terphenyl]-5'-carboxamide Yield: 57%; $^1$H NMR: (300 MHz, CDCl$_3$) δ: 0.73-0.98 (dd, 4H) 1.16 (m, 1H), 2.0 (s, 2H), 7.23 (s, 1H), 7.50-7.53 (t, 4H), 7.66 (d, 2H), 7.88-7.93 (m, 6H), 8.54 (s, 1H); MS (m/z): 515.39 (M+1)$^+$;

HPN-01526: 4-bromo-5'-carbamoyl-4"-ureido-[1,1':3',1"-terphenyl]-4'-yl 3-aminopropanoate Yield: 55%; $^1$H NMR: (300 MHz, CDCl$_3$) δ: 2.63 (t, 2H), 2.92 (t, 2H), 5.11 (s, 2H), 6.0 (s, 3H), 7.50-7.53 (t, 4H), 7.66 (d, 2H), 7.77-7.92 (m, 6H), 8.53 (s, 1H); MS (m/z): 498.34 (M+1)$^+$;

HPN-01527: 4'-(2-aminoacetamido)-4-bromo-4"-sulfamoyl-[1,1':3',1"-terphenyl]-5'-carboxamide Yield: 49%; $^1$H NMR: (300 MHz, CDCl$_3$) δ: 1.53 (s, 2H), 2.0 (s, 2H), 3.85 (s, 2H), 7.23 (s, 1H), 7.50-7.53 (t, 4H), 7.66 (d, 2H), 7.88-7.93 (m, 6H), 8.54 (s, 1H); MS (m/z): 504.37 (M+1)$^+$;

HPN-01529: N-(5'-carbamoyl-4-chloro-4"-sulfamoyl-[1,1':3',1"-terphenyl]-4'-yl)nicotinamide Yield: 68%; $^1$H NMR: (300 MHz, CDCl$_3$) δ: 7.23 (s, 2H), 7.59-7.62 (m, 3H), 7.88-7.91 (m, 6H), 8.10 (d, 2H), 8.28-8.30 (m, 2H), 8.76-8.80 (m, 2H), 9.14 (s, 1H), 10.10 (s, 2H), MS (m/z): 507.96 (M+1)$^+$;

HPN-01530: 4'-(3-aminopropanamido)-4-chloro-4"-sulfamoyl-[1,1':3',1"-terphenyl]-5'-carboxamide Yield: 48%; $^1$H NMR: (300 MHz, CDCl$_3$) δ: 1.5 (s, 2H), 2.71 (t, 2H), 3.02 (t, 2H), 7.23 (s, 2H), 7.62 (d, 2H), 7.88-7.92 (m, 6H), 8.10 (d, 2H), 8.29 (d, 1H), 8.80 (s, 1H), 10.10 (s, 2H), MS (m/z): 473.94 (M+1)$^+$;

HPN-01531: 4-chloro-4'-((2-hydroxyethyl)amino)-4"-sulfamoyl-[1,1':3',1"-terphenyl]-5'-carboxamide Yield: 52%; $^1$H NMR: (300 MHz, CDCl$_3$) δ: 3.55 (t, 2H), 3.67 (t, 2H), 4.92 (s, 1H), 7.22 (s, 2H), 7.62 (d, 2H), 7.88-7.92 (m, 6H), 8.10 (d, 2H), 8.29 (d, 1H), 8.80 (s, 1H), 10.10 (s, 1H), MS (m/z): 446.92 (M+1)⁺;

HPN-01532: 4-chloro-4'-((3-chlorobenzyl)amino)-4''-sulfamoyl-[1,1':3',1''-terphenyl]-5'-carboxamide Yield: 50%; ¹H NMR: (300 MHz, CDCl₃) δ: 4.32 (s, 2H), 7.88 (s, 1H), 7.23 (m, 2H), 7.35 (d, 2H), 7.43 (d, 1H), 7.62 (d, 2H), 7.88~7.92 (m, 6H), 8.10 (m, 3H), 8.60 (d, 1H), MS (m/z): 527.43 (M+1)⁺;

HPN-01533: 4'-(butylamino)-4-chloro-4''-sulfamoyl-[1,1':3',1''-terphenyl]-5'-carboxamide Yield: 57%; ¹H NMR: (300 MHz, CDCl₃) δ: 0.89 (t, 3H), 1.32 (m, 2H), 1.47 (m, 2H), 3.30 (t, 2H), 7.88 (s, 1H), 7.23 (s, 2H), 7.62 (d, 2H), 7.88-7.92 (m, 6H), 8.12 (m, 3H), 8.66 (d, 1H), MS (m/z): 458.97 (M+1)⁺;

HPN-01534: 4-chloro-4'-(phenethylamino)-4''-sulfamoyl-[1,1':3',1''-terphenyl]-5'-carboxamide Yield: 43%; ¹H NMR: (300 MHz, CDCl₃) δ: 2.93 (t, 2H), 3.40 (t, 2H), 7.88 (s, 1H), 7.23~7.26 (m, 7H), 7.62 (d, 2H), 7.88-7.92 (m, 6H), 8.12 (m, 3H), 8.66 (d, 1H), MS (m/z): 507.02 (M+1)⁺;

Example 24. Synthesis of HPN-016 Series Compounds

Additional HPN-01 derivatives were synthesized using the following process:

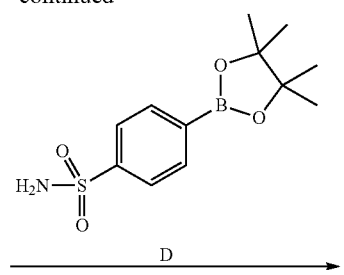

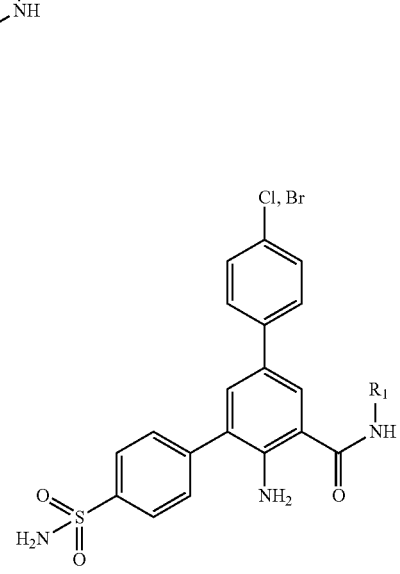

HPN-01601~HPN-01608,
HPN-01611~HPN-01620

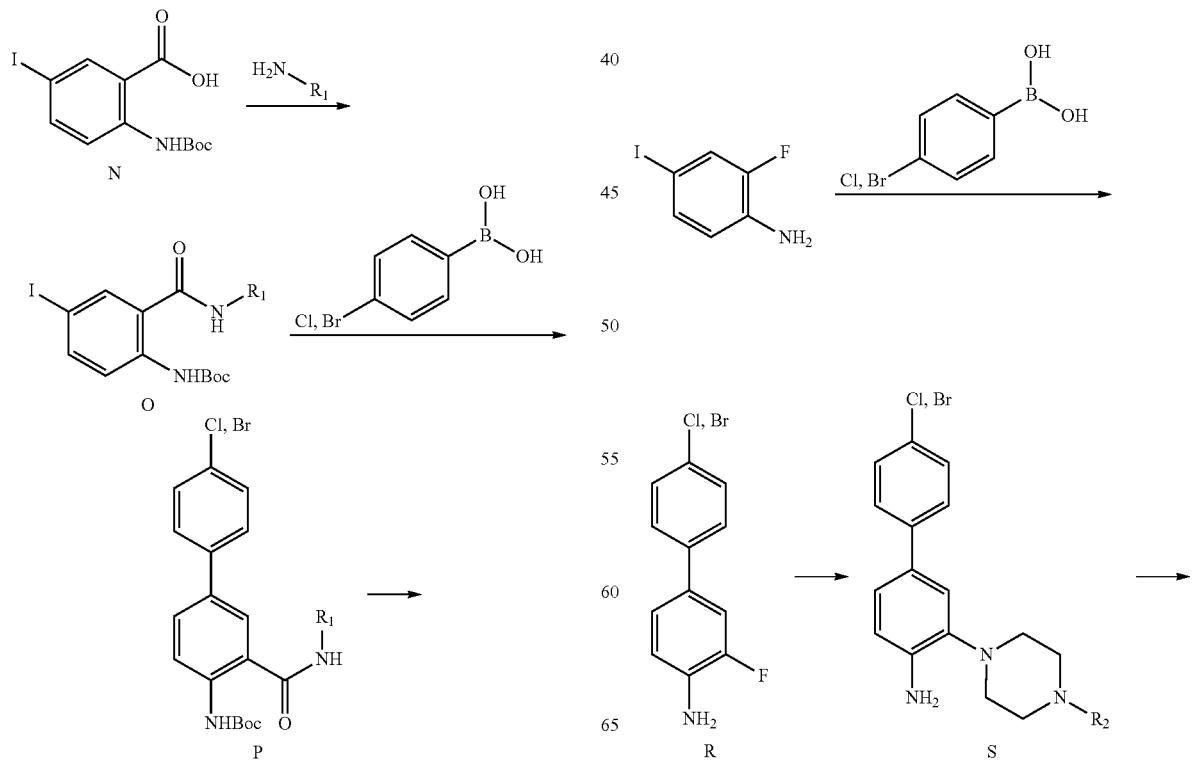

-continued

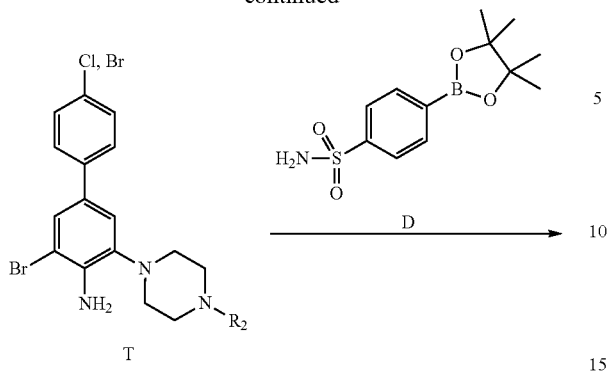

T

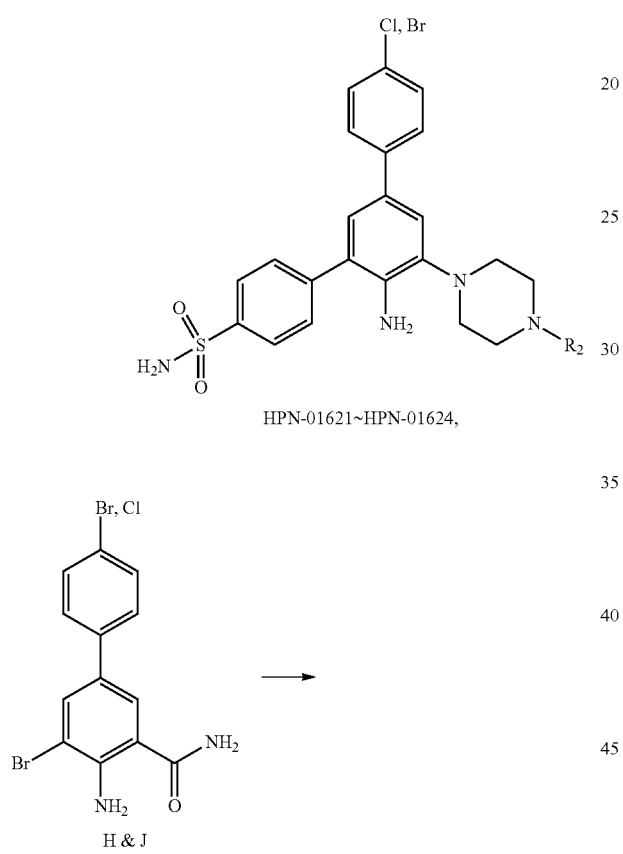

HPN-01621~HPN-01624,

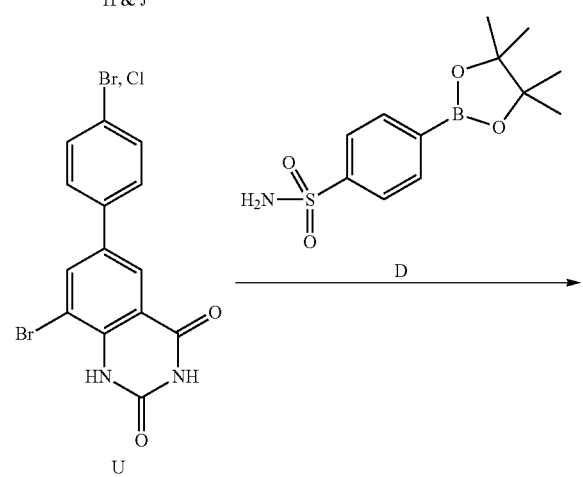

H & J

U

-continued

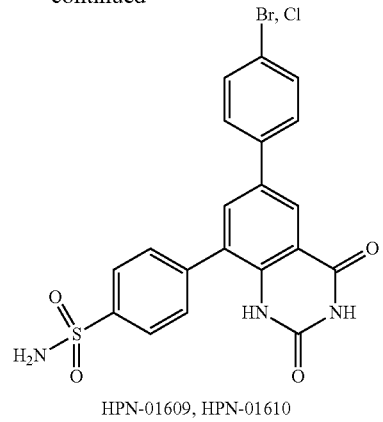

HPN-01609, HPN-01610

Details of the synthesis are as follows:

Step 1. Synthesis of Compound O 3.6 g of Compound N (10 mmol), 10 mmol substituted aliphatic amine, dissolved in 50 mL of acetonitrile, 8.8 g BOP (20 mmol), and 3.87 g DIEA (30 mmol) were reacted at room temperature for 30 hours under nitrogen protection. After the reaction was completed, the reaction solution was poured into ice water and extracted with 20 mL ethyl acetate for three times. The organic phase was washed with acid water, basic water and saturated saline in that order, and Compound 0 was obtained by silica gel column chromatography. The yield of Compound 0 was 88-94%.

Step 2. Synthesis of Compound P 3 mmol of Compound O, 3.3. mmol substituted phenyl-boronic acid, 0.03 g PdCl2(Ph3P)2 (3%) and 1.95 g CsCO3 (6 mmol) were added to a THF/water mixed solvent (THF: H2O=30 mL:20 mL) and heated to reflux for 24 hours under nitrogen protection. The reaction was stopped, and the reaction solution was poured into 200 ml ice water and stirred continuously. The precipitated solids were collected, dried, and subjected to silica gel column chromatography, resulting in isolation of Compound P. The yield of Compound P was 75%.

Step 3. Synthesis of Compound Q 5 mmol of Compound P and 0.9 g NBS (5.25 mmol) were dissolved in 100 mL glacial acetic acid and stirred at room temperature for 1 hour. After the reaction was completed, the reaction solution was partially concentrated and poured into ice water and stirred vigorously. The solids were collected, dried, and subjected to silica gel column chromatography, resulting in isolation of Compound Q. The yield of Compound Q was >90%.

Step 4. Synthesis of HPN-01601

10 mmol of Compound Q, 4.2 g compound D (15 mmol), 0.35 g $PdCl_2(PPh_3)_2$ (5%) and 2.8 g potassium carbonate (20 mmol) were dissolved in a mixture of 50 mL dioxane and 20 mL water. The reaction was carried out at 80° C. for 30 hours under nitrogen protection. After the reaction was completed, the reaction solution was poured into ice water and stirred vigorously. The solids were collected, dried, and subjected to silica gel column chromatography, resulting in isolation of Compound HPN-01601. The yield of Compound HPN-01601 was 75%. Structural information for this compound is as follows: $^1$H NMR: (300 MHz, CDCl$_3$) δ: 2.0 (s, 2H), 2.85 (s, 3H), 6.27 (s, 2H), 7.55-7.61 (t, 3H), 7.70 (d, 2H), 7.88-7.92 (dd, 4H), 8.10 (d, 2H), 8.31 (d, 1H); MS (m/z): 416.89 (M+1)$^+$;

Step 5. Synthesis of Compound R 0.7 g of compound 2-fluoro-4-iodoaniline (3 mmol), 3.3 mmol substituted phenylboronic acid, 0.03 g PdCl$_2$(Ph$_3$P)$_2$ (3%) and 1.95 g CsCO$_3$ (6 mmol) were added to a THF/water mixed solvent (THF:H2O=30 mL:20 mL) and heated to reflux for 24 hours under nitrogen protection. The reaction was stopped, and the reaction solution was poured into 200 mL ice water and stirred. The precipitated solids were collected, dried, and subjected to silica gel column chromatography, resulting in isolation of Compound R. The yield of Compound R was 65%.

Step 6. Synthesis of Compound S 2 mmol of Compound R and 2 mmol of substituted piperazine were dissolved in 20 mL of acetonitrile. 0.4 g of TEA (4 mmol) was added, and the reaction was stirred at room temperature for 16 hours. The reaction was poured into ice water and extracted with 20 mL ethyl acetate for three times. The purified Compound S had a yield of 80%.

Step 7. Synthesis of Compound T 2 mmol Compound T and 0.45 g NBS (2.6 mmol) were dissolved in 50 mL glacial acetic acid and stirred at room temperature for 1 hour. After the reaction was completed, the reaction solution was partially concentrated and poured into ice water and stirred vigorously. The solids were collected, dried, and subjected to silica gel column chromatography, resulting in isolation of Compound Q. The yield of Compound Q was >90%.

Step 8. Synthesis of Compound HPN-01621

1 mmol Compound T, 0.4 g compound D (1.5 mmol), 0.04 g PdCl$_2$(PPh$_3$)$_2$ (5%) and 0.3 g potassium carbonate (2 mmol) were dissolved in a mixture of 5 mL dioxane and 2 mL water and reacted at 80° C. for 24 hours under nitrogen protection. After the reaction was completed, the reaction solution was poured into ice water and stirred vigorously. The solids were collected, and subjected silica gel column chromatography, resulting in isolation Compound HPN-01621. The yield of Compound HPN-01621 was 45%. Structural information for this compound is as follows: $^1$H NMR: (300 MHz, CDCl$_3$) δ: 1.91-2.0 (d, 3H), 2.78 (t, 4H), 3.46 (t, 4H), 6.27 (s, 2H), 6.79 (d, 2H), 7.55 (d, 2H), 7.88-7.92 (dd, 4H), 8.10 (d, 2H); MS (m/z): 443.96 (M+1)$^+$.

Step 9. Synthesis of Compound U 2 mmol of Compound H&J and 0.2 g triphosgene (0.7 mmol) were dissolved in 15 mL dichloromethane at low temperature. 0.5 g TEA (5 mmol) was slowly added and the mixture was stirred at room temperature for 16 hours. After the reaction was completed, the reaction solution was partially concentrated and poured into ice water and stirred vigorously. The solids were collected, dried, and subjected to silica gel column chromatography, resulting in isolation of Compound U. The yield of Compound U was 44%.

Step 10. Synthesis of Compound HPN-01609

1 mmol of Compound U, 0.4 g Compound D (1.5 mmol), 0.04 g PdCl$_2$(PPh$_3$)$_2$ (5%) and 0.3 g potassium carbonate (2 mmol) were dissolved in a mixture of 5 mL dioxane and 2 mL water, and reacted at 80° C. for 24 hours under nitrogen protection. After the reaction was completed, the reaction solution was poured into ice water and stirred vigorously. The solids were collected, dried, and subjected to silica gel column chromatography, resulting in isolation of Compound HPN-01609. The yield of Compound HPN-01609 was 45%. Structural information for this compound is as follows: $^1$H NMR: (300 MHz, CDCl$_3$) δ: 2.0 (s, 2H), 7.88 (s, 4H), 7.55 (d, 2H), 7.88-7.93 (m, 5H), 8.10 (d, 2H), 8.54 (d, 1H), 10.0 (s, 1H); MS (m/z): 428.86 (M+1)$^+$. According to the above steps, the synthesis of the series of compounds is completed, and the structural information is summarized as follows:

HPN-01602: 4'-amino-4-bromo-N-methyl-4"-sulfamoyl-[1,1':3',1"-terphenyl]-5'-carboxamide Yield: 53%; $^1$H NMR: (300 MHz, CDCl$_3$) δ: 2.0 (s, 2H), 2.85 (s, 3H), 6.27 (s, 2H), 7.3-7.70 (m, 7H) 7.88-7.92 (dd, 4H), 8.31 (d, 1H); MS (m/z): 461.34 (M+1)$^+$;

HPN-01603: 4'-amino-4-chloro-N-propyl-4"-sulfamoyl-[1,1':3',1"-terphenyl]-5'-carboxamide Yield: 58%; $^1$H NMR: (300 MHz, CDCl$_3$) δ: 0.90 (t, 3H), 1.64 (m, 2H), 2.0 (s, 2H), 3.42 (t, 2H), 6.27 (s, 2H), 7.55 (d, 2H), 7.70 (d, 1H), 8.10-8.03 (t, 3H), 8.31 (d, 1H); MS (m/z): 444.95 (M+1)$^+$;

HPN-01604: 4'-amino-4-bromo-N-propyl-4"-sulfamoyl-[1, 1':3',1"-terphenyl]-5'-carboxamide Yield: 66%; $^1$H NMR: (300 MHz, CDCl$_3$) δ: 0.90 (t, 3H), 1.64 (m, 2H), 2.0 (s, 2H), 3.42 (t, 2H), 6.27 (s, 2H), 7.53 (d, 2H), 7.70-7.66 (t, 3H), 7.88-7.92 (dd, 4H), 8.03 (s, 1H), 8.31 (d, 1H); MS (m/z): 489.4 (M+1)$^+$;

HPN-01605: 4'-amino-4-chloro-N-cyclopropyl-4"-sulfamoyl-[1,1':3',1"-terphenyl]-5'-carboxamide Yield: 64%; $^1$H NMR: (300 MHz, CDCl$_3$) δ: 1H-NMR: 0.61-0.86 (m, 4H), 2.0 (s, 2H), 2.75 (m, 1H), 6.27 (s, 2H), 7.55 (d, 2H), 7.70 (d, 1H), 7.88-7.92 (dd, 4H) 8.10 (d, 2H), 8.31 (d, 1H); MS (m/z): 442.93 (M+1)$^+$;

HPN-01606: 4'-amino-4-bromo-N-cyclopropyl-4"-sulfamoyl-[1,1':3',1"-terphenyl]-5'-carboxamide Yield: 54%; $^1$H NMR: (300 MHz, CDCl$_3$) δ: 0.61-0.86 (m, 4H), 2.0 (s, 2H), 2.75 (m, 1H), 6.27 (s, 2H), 7.53 (d, 2H), 7.66-7.70 (t, 3H), 7.88-7.92 (dd, 4H), 8.03 (s, 1H), 8.31 (d, 1H); MS (m/z): 487.38 (M+1)$^+$;

HPN-01607: 4'-amino-4-chloro-N-(2-hydroxyethyl)-4"-sulfamoyl-[1,1':3',1"-terphenyl]-5'-carboxamide Yield: 55%; $^1$H NMR: (300 MHz, CDCl$_3$) δ: 2.0 (s, 2H), 3.30 (t, 2H), 3.65 (t, 3H), 6.27 (s, 2H), 7.55 (d, 2H), 7.70 (d, 1H), 7.88-7.92 (dd, 4H) 8.10 (d, 2H), 8.31 (d, 1H); MS (m/z): 446.92 (M+1)$^+$;

HPN-01608: 4'-amino-4-bromo-N-(2-hydroxyethyl)-4"-sulfamoyl-[1,1':3',1"-terphenyl]-5'-carboxamide Yield: 54%; ¹H NMR: (300 MHz, CDCl₃) δ: 2.0 (s, 2H), 3.30 (t, 2H), 3.65 (t, 3H), 6.27 (s, 2H), 7.53 (d, 2H), 7.66-7.70 (t, 3H), 7.88-7.92 (dd, 4H), 8.03 (s, 1H), 8.31 (d, 1H); MS (m/z): 491.37 (M+1)⁺;

HPN-01610: 4-(6-(4-bromophenyl)-2,4-dioxo-1,2,3,4-tetrahydroquinazolin-8-yl)benzene sulfonamide Yield: 51%; ¹H NMR: (300 MHz, CDCl₃) δ: 2.0 (s, 2H), 7.88 (s, 4H), 7.53 (d, 2H) 7.66 (d, 2H), 7.88-7.92 (dd, 4H), 8.54 (d, 1H), 10.0 (s, 1H); MS (m/z): 473.31 (M+1)⁺;

HPN-01611: 4'-amino-4-chloro-N-phenyl-4"-sulfamoyl-[1,1':3',1"-terphenyl]-5'-carboxamide Yield: 54%; ¹H NMR: (300 MHz, CDCl₃) δ: 5.02 (s, 2H), 7.07 (m, 1H), 7.23-7.32 (dd, 4H), 7.70 (m, 2H), 8.10-8.04 (m, 3H), 8.55 (d, 1H), 10.32 (s, 1H), MS (m/z): 478.96 (M+1)⁺;

HPN-01612: 4'-amino-4-bromo-N-phenyl-4"-sulfamoyl-[1,1':3',1"-terphenyl]-5'-carboxamide Yield: 67%; ¹H NMR: (300 MHz, CDCl₃) δ: 5.02 (s, 2H), 7.07 (m, 1H), 7.23-7.32 (dd, 4H), 7.65 (dd, 4H), 7.88 (s, 4H), 8.04 (d, 1H), 8.55 (s, 1H) 10.32 (s, 1H); MS (m/z): 523.42 (M+1)⁺;

HPN-01613 4'-amino-4-chloro-N-(3-fluorophenyl)-4"-sulfamoyl-[1,1':3',1"-terphenyl]-5'-carboxamide Yield: 54%; ¹H NMR: (300 MHz, CDCl₃) δ: 5.02 (s, 2H), 6.96 (t, 1H), 7.23 (s, 1H), 7.40 (t, 1H), 7.56-7.62 (M, 3H), 7.88 (s, 4H), 8.04-8.10 (dd, 3H) 8.55 (d, 1H), 10.32 (s, 1H); MS (m/z): 496.95 (M+1)⁺;

HPN-01614: 4'-amino-4-bromo-N-(3-fluorophenyl)-4"-sulfamoyl-[1,1':3',1"-terphenyl]-5'-carboxamide Yield: 64%; ¹H NMR: (300 MHz, CDCl₃) δ: 5.02 (s, 2H), 6.96 (t, 1H), 7.23 (s, 1H), 7.40 (t, 1H), 7.65-7.72 (M, 5H), 7.88 (s, 4H), 8.04 (d, 1H) 8.55 (d, 1H), 10.32 (s, 1H); MS (m/z): 541.41 (M+1)⁺;

HPN-01615: 4'-amino-4-chloro-N-(3,4-difluorophenyl)-4"-sulfamoyl-[1,1':3',1"-terphenyl]-5'-carboxamide Yield: 54%; ¹H NMR: (300 MHz, CDCl₃) δ: 5.02 (s, 2H), 7.23 (s, 2H), 7.37 (t, 1H), 7.58-7.62 (dd, 3H), 7.73 (d, 1H), 7.80-8.10 (t, 3H), 8.55 (d, 1H), 10.32 (s, 1H); MS (m/z): 514.94 (M+1)⁺;

HPN-01616: 4'-amino-4-bromo-N-(3,4-difluorophenyl)-4"-sulfamoyl-[1,1':3',1"-terphenyl]-5'-carboxamide Yield: 64%; ¹H NMR: (300 MHz, CDCl₃) δ: 5.02 (s, 2H), 7.23 (s, 2H), 7.37 (t, 1H) 7.73 (m, 6H), 7.88 (s, 4H) 8.04 (d, 1H), 8.55 (d, 1H), 10.32 (s, 1H); MS (m/z): 559.4 (M+1)⁺;

HPN-01617: 4'-amino-4-chloro-N-(3,4-dihydroxyphenyl)-4"-sulfamoyl-[1,1':3',1"-terphenyl]-5'-carboxamide Yield: 54%; ¹H NMR: (300 MHz, CDCl₃) δ: 2.0 (s, 2H), 5.35 (d, 2H), 6.27 (s, 2H), 6.76 (d, 1H), 7.01 (d, 1H), 7.15 (d, 2H), 7.45-7.63 (m, 6H), 8.10 (d, 2H), 8.31 (d, 1H), 9.15 (s, 1H); MS (m/z): 510.96 (M+1)⁺;

HPN-01618: 4'-amino-4-bromo-N-(3,4-dihydroxyphenyl)-4"-sulfamoyl-[1,1':3',1"-terphenyl]-5'-carboxamide Yield: 59%; ¹H NMR: (300 MHz, CDCl₃) δ: 2.0 (s, 2H), 5.35 (d, 2H), 6.27 (s, 2H), 6.76 (d, 1H), 7.01 (d, 1H), 7.15 (d, 2H), 7.45-7.53 (dd, 4H) 7.63-7.66 (dd, 4H), 8.10 (d, 2H), 8.31 (d, 1H), 9.15 (s, 1H); MS (m/z): 555.41 (M+1)⁺;

HPN-01619: 4'-amino-4-chloro-N-(3-methoxyphenyl)-4"-sulfamoyl-[1,1':3',1"-terphenyl]-5'-carboxamide Yield: 54%; ¹H NMR: (300 MHz, CDCl₃) δ: 3.74 (s, 3H), 5.02 (s, 2H), 6.67 (d, 1H), 7.20-7.23 (dd, 4H), 7.47 (d, 1H), 7.62 (d, 2H), 7.88 (s, 4H), 8.04-8.10 (dd, 3H), 8.55 (d, 1H), 10.32 (s, 1H); MS (m/z): 508.99 (M+1)⁺;

HPN-01620: 4'-amino-4-bromo-N-(3-methoxyphenyl)-4"-sulfamoyl-[1,1':3',1"-terphenyl]-5'-carboxamide Yield: 57%; ¹H NMR: (300 MHz, CDCl₃) δ: 3.74 (s, 3H), 5.02 (s, 2H), 6.67 (d, 1H), 7.20-7.23 (dd, 4H), 7.47 (d, 1H), 7.65 (s, 4H), 7.88 (s, 4H), 8.04 (d, 1H), 8.55 (d, 1H), 10.32 (s, 1H); MS (m/z): 553.44 (M+1)⁺;

HPN-01622: 6'-amino-4"-bromo-5'-(piperazin-1-yl)-[1,1':3',1"-terphenyl]-4-sulfonamide Yield: 54%; ¹H NMR: (300 MHz, CDCl₃) δ: 1.91-2.0 (d, 3H), 2.78 (t, 4H), 3.46 (t, 4H), 6.27 (s, 2H) 6.79 (d, 2H), 7.53 (d, 2H), 7.66 (d, 2H), 7.88-7.92 (dd, 4H); MS (m/z): 488.41 (M+1)⁺;

HPN-01623: 4-(4'-amino-4-chloro-4"-sulfamoyl-[1,1':3',1"-terphenyl]-5'-yl)piperazine-1-carboxamide Yield: 54%; ¹H NMR: (300 MHz, CDCl₃) δ: 3.29 (t, 4H), 3.52 (t, 4H), 5.02 (s, 2H), 6.20 (s, 2H), 6.77 (s, 1H), 7.13 (s, 1H), 7.23 (s, 2H), 7.62 (d, 2H) 7.88 (s, 4H), 8.10 (d, 0.2H); MS (m/z): 586.99 (M+1)⁺;

HPN-01624: 4-(4'-amino-4-bromo-4"-sulfamoyl-[1,1':3',1"-terphenyl]-5'-yl)piperazine-1-carboxamide Yield: 66%; ¹H NMR: (300 MHz, CDCl₃) δ: 2.78 (t, 4H), 3.46 (t, 4H), 5.02 (s, 2H), 6.77 (s, 1H), 7.13 (s, 1H), 7.23 (s, 2H), 7.65 (s, 4H), 7.88 (s, 4H); MS (m/z): 488.42 (M+1)⁺;

HPN-01625: 4'-amino-4-chloro-N-(pyridin-3-yl)-4"-sulfamoyl-[1,1':3',1"-terphenyl]-5'-carboxamide Yield: 57%; 1H NMR: (300 MHz, CDCl₃) δ: 5.02 (s, 2H), 7.23 (s, 2H), 7.40 (d, 1H), 7.62 (d, 2H), 7.88 (d, 4H), 8.10-8.17 (m, 4H), 8.33 (d, 1H), 8.55 (d, 1H), 8.93 (d, 1H), 10.33 (s, 1H), MS (m/z): 479.95 (M+1)⁺;

HPN-01626: 4'-amino-4-chloro-N-(1H-pyrrol-2-yl)-4"-sulfamoyl-[1,1':3',1"-terphenyl]-5'-carboxamide Yield: 58%; ¹H NMR: (300 MHz, CDCl₃) δ: 5.02 (s, 2H), 6.25 (d, 1H), 6.38 (d, 1H), 6.95 (d, 1H), 7.23 (s, 2H), 7.62

(d, 2H), 7.88 (d, 4H), 8.10-8.12 (m, 3H), 8.55 (d, 1H), 11.17 (s, 1H), 12.00 (s, 1H), MS (m/z): 467.94 (M+1)$^+$;

HPN-01627: 4'-amino-4-chloro-4"-sulfamoyl-N-(thiophen-3-yl)-[1,1':3',1"-terphenyl]-5'-carboxamide Yield: 53%; $^1$H NMR: (300 MHz, CDCl$_3$) δ: 5.02 (s, 2H), 6.43 (d, 1H), 7.23 (s, 2H), 7.48 (d, 1H), 7.59~7.62 (m, 3H), 7.88 (d, 4H), 8.10-8.12 (m, 3H), 8.55 (d, 1H), 10.21 (s, 1H), MS (m/z): 484.99 (M+1)$^+$;

HPN-01628: 4'-amino-4-chloro-N-(1H-pyrrol-3-yl)-4"-sulfamoyl-[1,1':3',1"-terphenyl]-5'-carboxamide Yield: 48%; $^1$H NMR: (300 MHz, CDCl$_3$) δ: 5.02 (s, 2H), 6.23 (d, 1H), 6.86 (d, 1H), 7.23 (s, 2H), 7.62 (d, 2H), 7.88 (d, 4H), 8.10-8.12 (m, 3H), 8.55 (d, 1H), 9.05 (s, 1H), 10.21 (s, 1H), MS (m/z): 467.94 (M+1)$^+$;

HPN-01629: N-((1H-pyrrol-2-yl)methyl)-4'-amino-4-chloro-4"-sulfamoyl-[1,1':3',1"-terphenyl]-5'-carboxamide Yield: 55%; $^1$H NMR: (300 MHz, CDCl$_3$) δ: 4.32 (s, 2H), 5.02 (s, 2H), 5.88 (d, 1H), 6.11 (d, 1H), 6.64 (d, 1H), 7.23 (s, 2H), 7.62 (d, 2H), 7.88 (d, 4H), 8.10-8.12 (m, 3H), 8.55 (d, 1H), 8.77 (s, 1H), 11.86 (s, 1H), MS (m/z): 481.97 (M+1)$^+$;

HPN-01630 4'-amino-4-chloro-N-(pyridin-3-ylmethyl)-4"-sulfamoyl-[1,1':3',1"-terphenyl]-5'-carboxamide Yield: 68%; $^1$H NMR: (300 MHz, CDCl$_3$) δ: 4.47 (s, 2H), 5.02 (s, 2H), 7.23 (s, 2H), 7.37 (d, 1H), 7.62 (d, 2H), 7.88 (m, 5H), 8.05~8.10 (m, 3H), 8.37 (d, 1H), 8.58-8.60 (m, 2H), 8.73 (s, 1H), MS (m/z): 493.98 (M+1)$^+$;

Example 25. Effects of HPN-01 Variants on Lipid Droplet (LD) Formation in Hepatocytes The ability of each HPN-01 derivative obtained from the synthesis methods described above, to inhibit LD formation in hepatocytes, was tested using the procedure outlined in Example 3. The results of this analysis are shown below in Table 6 (second column).

Example 26. Effects of HPN-01 Variants on the Expression of SREBP-1 and SREBP-2 in Primary Human Hepatocytes The ability of each HPN-01 derivative obtained from the synthesis methods described above, to inhibit SREBP-1 and SREBP-2 mRNA expression in primary hepatocytes, was tested using the procedure outlined in Example 6. The results of this analysis are shown in Table 6 (third and fourth columns).

TABLE 6

Inhibitory Effects of HPN-01 Variants

| Compound No. | LD content inhibition (EC$_{50}$, μM) | SREBP-1 mRNA inhibition (EC$_{50}$, μM) | SREBP-2 mRNA inhibition (EC$_{50}$, μM) |
|---|---|---|---|
| HPN-01101 | 0.57 | 2.96 | 6.98 |
| HPN-01102 | 0.46 | 1.61 | 3.37 |
| HPN-01103 | 0.99 | 2.14 | 3.08 |
| HPN-01104 | 0.67 | 2.08 | 3.26 |
| HPN-01105 | 1.09 | 3.24 | 5.26 |
| HPN-01106 | 2.85 | 6.35 | 6.45 |
| HPN-01107 | 1.17 | 5.66 | 7.37 |
| HPN-01108 | 0.55 | 2.59 | 4.67 |
| HPN-01109 | 1.37 | 2.71 | 4.46 |
| HPN-01110 | 0.81 | 2.26 | 3.60 |
| HPN-01111 | 0.75 | 2.08 | 2.44 |
| HPN-01112 | 0.65 | 2.03 | 1.36 |
| HPN-01113 | 0.33 | 0.69 | 0.97 |
| HPN-01114 | 0.21 | 1.27 | 2.47 |
| HPN-01115 | 2.35 | 6.42 | 5.99 |
| HPN-01116 | 1.01 | 3.74 | 5.01 |
| HPN-01117 | 1.15 | 6.99 | 8.24 |
| HPN-01118 | 0.84 | 2.34 | 2.51 |
| HPN-01119 | 1.08 | 2.71 | 4.17 |
| HPN-01120 | 0.68 | 6.44 | 5.10 |
| HPN-01121 | 2.14 | 6.59 | 8.04 |
| HPN-01122 | 2.44 | 9.61 | 7.29 |
| HPN-01123 | 0.89 | 3.45 | 4.45 |
| HPN-01124 | 0.67 | 1.86 | 3.25 |
| HPN-01125 | 0.38 | 2.80 | 4.27 |
| HPN-01126 | 0.83 | 2.43 | 4.54 |
| HPN-01127 | 0.33 | 1.17 | 3.37 |
| HPN-01128 | 0.89 | 2.40 | 3.47 |
| HPN-01129 | 0.29 | 1.69 | 3.10 |
| HPN-01130 | 0.06 | 0.97 | 1.80 |
| HPN-01131 | 0.38 | 1.28 | 2.26 |
| HPN-01132 | 0.07 | 0.36 | 1.55 |
| HPN-01133 | 0.70 | 2.55 | 3.07 |
| HPN-01201 | 1.20 | 3.16 | 6.85 |
| HPN-01202 | 0.29 | 0.64 | 0.90 |
| HPN-01203 | 0.55 | 1.70 | 2.10 |
| HPN-01204 | 1.01 | 4.18 | 4.59 |
| HPN-01205 | 0.52 | 1.75 | 2.09 |
| HPN-01206 | 0.90 | 1.68 | 1.07 |
| HPN-01207 | 0.98 | 1.94 | 2.73 |
| HPN-01208 | 1.69 | 3.25 | 5.77 |
| HPN-01209 | 0.82 | 2.33 | 1.98 |
| HPN-01210 | 0.53 | 1.92 | 2.97 |
| HPN-01211 | 0.78 | 3.79 | 7.14 |
| HPN-01212 | 0.75 | 2.27 | 1.85 |
| HPN-01213 | 1.29 | 4.55 | 4.88 |
| HPN-01214 | 0.52 | 3.42 | 6.32 |
| HPN-01215 | 0.61 | 3.72 | 6.78 |
| HPN-01216 | 0.96 | 4.35 | 7.93 |
| HPN-01217 | 0.18 | 1.03 | 2.07 |
| HPN-01218 | 0.99 | 4.54 | 6.51 |
| HPN-01219 | 0.96 | 4.71 | 6.91 |
| HPN-01220 | 0.46 | 1.59 | 3.21 |
| HPN-01221 | 0.77 | 1.67 | 3.47 |
| HPN-01222 | 1.36 | 7.31 | 12.84 |
| HPN-01223 | 1.03 | 2.64 | 4.20 |
| HPN-01224 | 0.58 | 1.58 | 2.57 |
| HPN-01301 | 1.19 | 3.44 | 5.35 |
| HPN-01302 | 1.03 | 3.16 | 4.52 |
| HPN-01303 | 1.30 | 6.62 | 10.54 |
| HPN-01304 | 0.83 | 1.54 | 2.77 |
| HPN-01305 | 0.82 | 1.74 | 3.90 |
| HPN-01306 | 1.33 | 1.76 | 3.26 |
| HPN-01307 | 1.36 | 5.68 | 4.59 |
| HPN-01308 | 1.90 | 6.36 | 11.15 |
| HPN-01309 | 3.50 | 8.16 | 8.96 |
| HPN-01310 | 10.49 | 13.02 | 23.94 |
| HPN-01311 | 2.02 | 3.09 | 5.59 |
| HPN-01312 | 1.45 | 7.53 | 10.32 |
| HPN-01313 | 1.76 | 5.51 | 9.41 |
| HPN-01314 | 1.18 | 4.57 | 7.71 |
| HPN-01315 | 2.61 | 7.72 | 14.04 |
| HPN-01316 | 5.92 | 8.02 | 11.21 |
| HPN-01317 | 0.58 | 3.35 | 4.32 |
| HPN-01318 | 0.31 | 0.77 | 1.16 |
| HPN-01319 | 0.63 | 4.80 | 3.42 |

TABLE 6-continued

Inhibitory Effects of HPN-01 Variants

| Compound No. | LD content inhibition (EC$_{50}$, μM) | SREBP-1 mRNA inhibition (EC$_{50}$, μM) | SREBP-2 mRNA inhibition (EC$_{50}$, μM) |
|---|---|---|---|
| HPN-01320 | 0.69 | 1.10 | 2.16 |
| HPN-01321 | 1.76 | 3.06 | 5.31 |
| HPN-01322 | 0.83 | 1.62 | 2.55 |
| HPN-01401 | 1.38 | 1.97 | 3.53 |
| HPN-01402 | 0.60 | 1.18 | 2.50 |
| HPN-01403 | 0.36 | 1.96 | 3.09 |
| HPN-01404 | 0.64 | 1.97 | 3.39 |
| HPN-01405 | 0.76 | 2.50 | 3.98 |
| HPN-01406 | 0.68 | 1.53 | 2.79 |
| HPN-01407 | 1.07 | 5.41 | 9.69 |
| HPN-01408 | 1.50 | 2.55 | 4.37 |
| HPN-01409 | 0.50 | 1.05 | 1.42 |
| HPN-01410 | 0.58 | 2.09 | 4.08 |
| HPN-01411 | 0.94 | 1.59 | 2.84 |
| HPN-01412 | 2.07 | 3.09 | 6.11 |
| HPN-01413 | 0.74 | 1.52 | 2.70 |
| HPN-01414 | 1.57 | 3.94 | 9.86 |
| HPN-01415 | 0.66 | 2.35 | 6.45 |
| HPN-01416 | 1.51 | 3.02 | 4.01 |
| HPN-01417 | 1.26 | 3.15 | 4.92 |
| HPN-01418 | 0.98 | 2.69 | 2.45 |
| HPN-01419 | 0.50 | 1.82 | 3.53 |
| HPN-01420 | 0.42 | 2.14 | 2.37 |
| HPN-01421 | 0.75 | 1.51 | 2.22 |
| HPN-01422 | 1.44 | 1.52 | 3.93 |
| HPN-01423 | 0.81 | 1.36 | 2.37 |
| HPN-01424 | 1.45 | 2.69 | 4.31 |
| HPN-01425 | 6.48 | 2.83 | 3.44 |
| HPN-01426 | 1.15 | 11.03 | 9.40 |
| HPN-01427 | 1.11 | 3.32 | 3.83 |
| HPN-01428 | 1.14 | 5.65 | 18.82 |
| HPN-01429 | 0.14 | 6:69 | 3.98 |
| HPN-01430 | 5.36 | 1.88 | 4.37 |
| HPN-01501 | 1.67 | 5.04 | 8.55 |
| HPN-01502 | 0.79 | 1.65 | 2.30 |
| HPN-01503 | 0.70 | 3.94 | 6.48 |
| HPN-01504 | 0.46 | 0.73 | 1.11 |
| HPN-01505 | 0.59 | 1.36 | 2.41 |
| HPN-01506 | 6.48 | 7.31 | 17.13 |
| HPN-01513 | 0.68 | 1.63 | 2.88 |
| HPN-01514 | 1.15 | 2.83 | 5.10 |
| HPN-01515 | 0.48 | 0.95 | 1.32 |
| HPN-01516 | 1.10 | 1.91 | 2.07 |
| I IPN-01517 | 0.48 | 1.96 | 2.94 |
| HPN-01518 | 1.11 | 2.92 | 4.86 |
| HPN-01519 | 0.81 | 1.51 | 2.75 |
| HPN-01520 | 2.51 | 3.01 | 4.45 |
| HPN-01525 | 1.45 | 5.61 | 10.03 |
| HPN-01526 | 1.15 | 1.63 | 3.83 |
| HPN-01527 | 2.60 | 5.25 | 5.69 |
| HPN-01529 | 1.67 | 3.09 | 18.82 |
| HPN-01530 | 0.46 | 3.94 | 9.40 |
| HPN-01531 | 6.48 | 3.15 | 5.71 |
| HPN-01532 | 1.15 | 2.69 | 8.60 |
| HPN-01533 | 0.48 | 2.83 | 11.73 |
| HPN-01534 | 1.11 | 2.92 | 6.79 |
| HPN-01601 | 7.50 | 11.03 | 18.82 |
| HPN-01602 | 2.32 | 3.32 | 4.73 |
| HPN-01603 | 2.39 | 7.22 | 9.40 |
| HPN-01604 | 1.14 | 1.95 | 5.71 |
| HPN-01605 | 0.69 | 1.78 | 2.35 |
| HPN-01606 | 0.14 | 1.13 | 2.75 |
| HPN-01607 | 3.05 | 6.73 | 12.47 |
| HPN-01608 | 1.20 | 2.39 | 4.31 |
| HPN-01609 | 1.18 | 5.45 | 8.36 |
| HPN-01610 | 1.16 | 2.00 | 3.44 |
| HPN-01611 | 0.79 | 1.37 | 2.24 |
| HPN-01612 | 0.64 | 3.11 | 5.48 |
| HPN-01613 | 1.37 | 1.55 | 2.20 |
| HPN-01614 | 0.82 | 5.65 | 8.60 |
| HPN-01615 | 1.15 | 6.69 | 11.73 |
| HPN-01616 | 1.07 | 3.57 | 6.79 |
| HPN-01617 | 0.32 | 1.88 | 3.68 |
| HPN-01618 | 1.43 | 3.57 | 6.37 |
| HPN-01619 | 1.33 | 4.18 | 7.95 |
| HPN-01620 | 5.36 | 5.76 | 9.22 |
| HPN-01621 | 1.40 | 2.52 | 3.87 |
| HPN-01622 | 22.76 | 37.11 | 50.78 |
| HPN-01623 | 15.29 | 38.14 | 50.05 |
| HPN-01624 | 1.30 | 7.54 | 13.51 |
| HPN-01625 | 2.32 | 3.32 | 18.82 |
| HPN-01626 | 3.05 | 7.22 | 12.47 |
| HPN-01627 | 1.20 | 1.95 | 4.31 |
| HPN-01628 | 1.16 | 2.39 | 5.48 |
| HPN-01629 | 1.37 | 2.00 | 8.60 |
| HPN-01630 | 2.39 | 3.57 | 3.87 |

Figure 27:
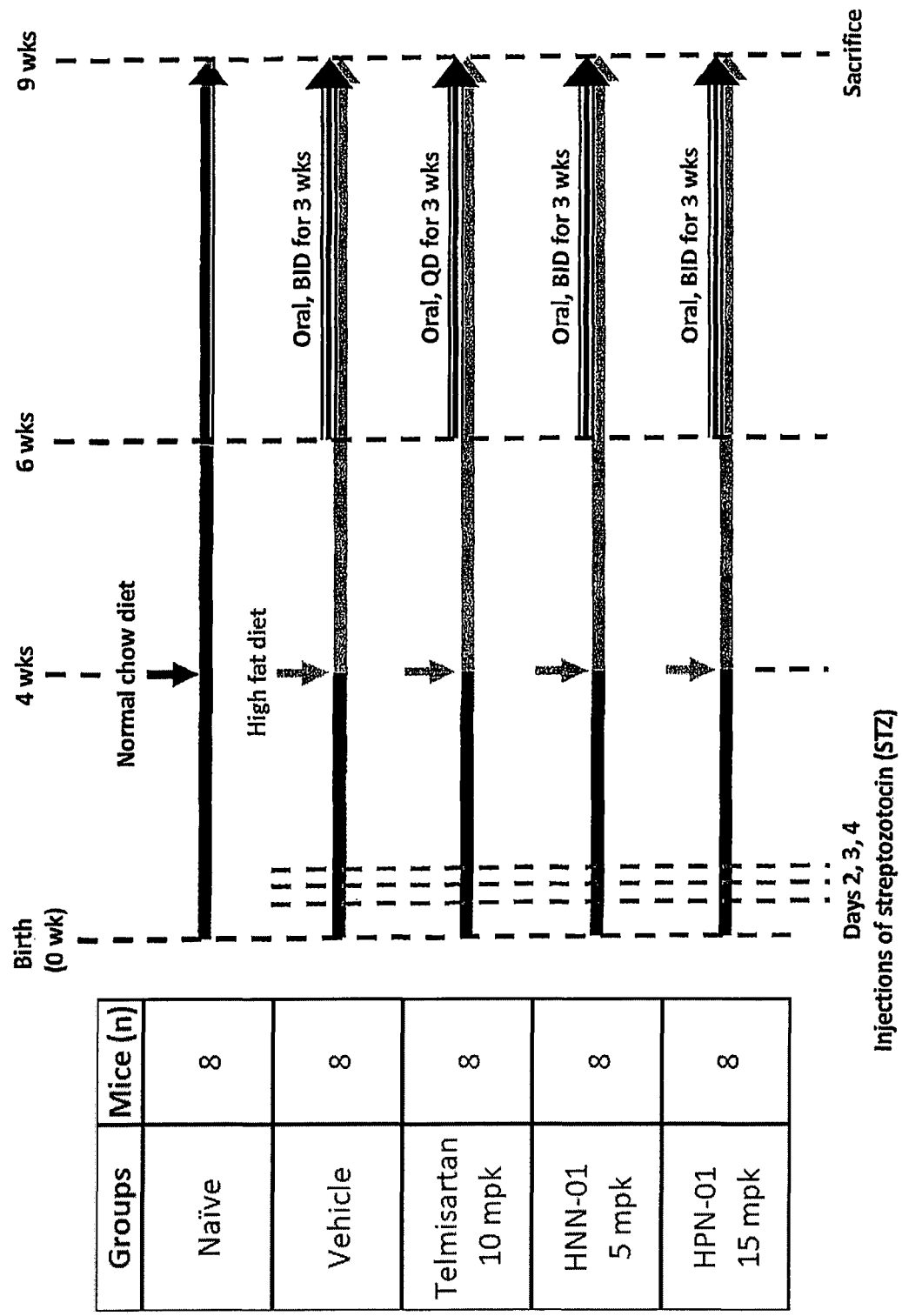
FIG. 27. Design of study to test in vivo HPN-01 efficacy on streptozotocin (STZ) and high fat diet-induced (nSTZ+ HFD) NASH mice.
Figure 28A:
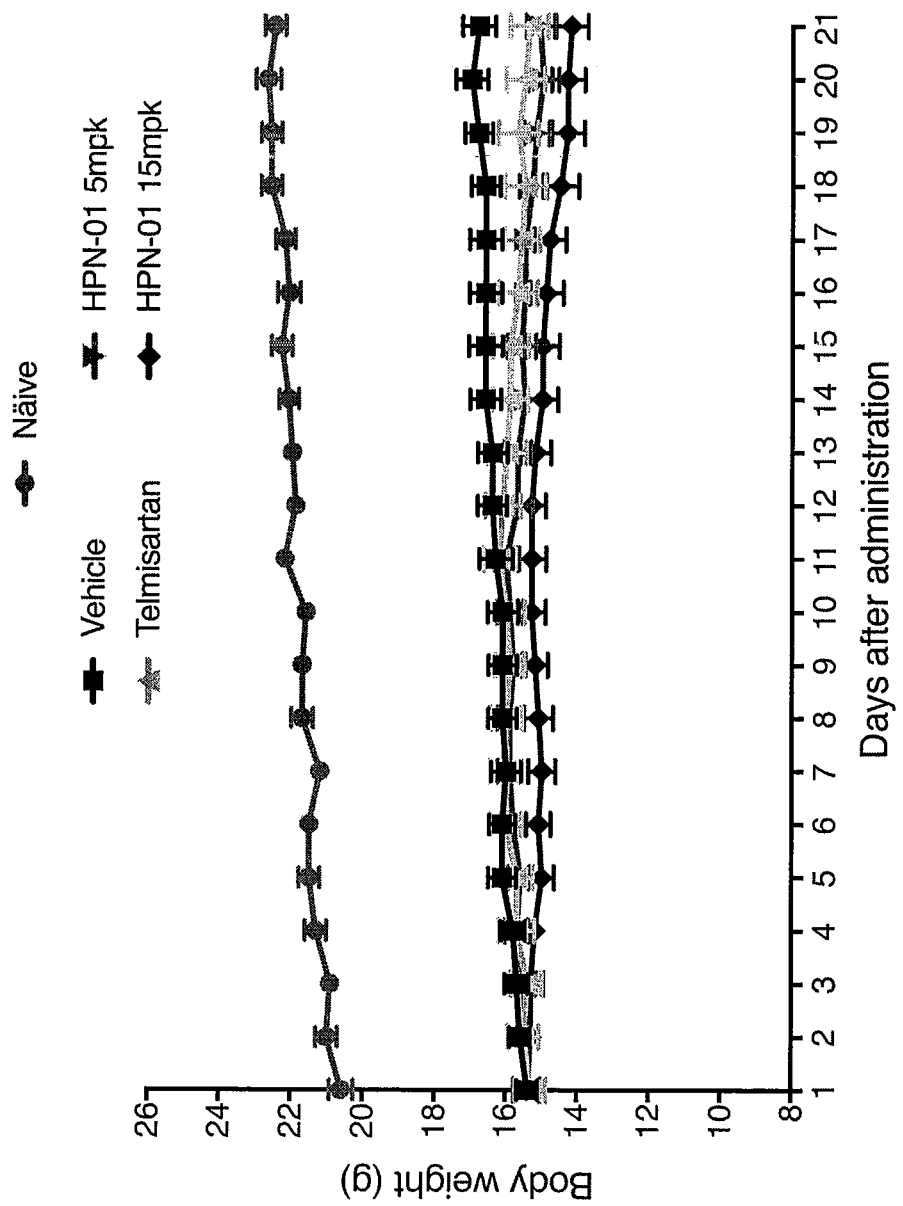
FIGS. 28A and 28B. Effect of HPN-01 on nSTZ+HFD NASH mice body weight and daily food intake.
Figure 28B:
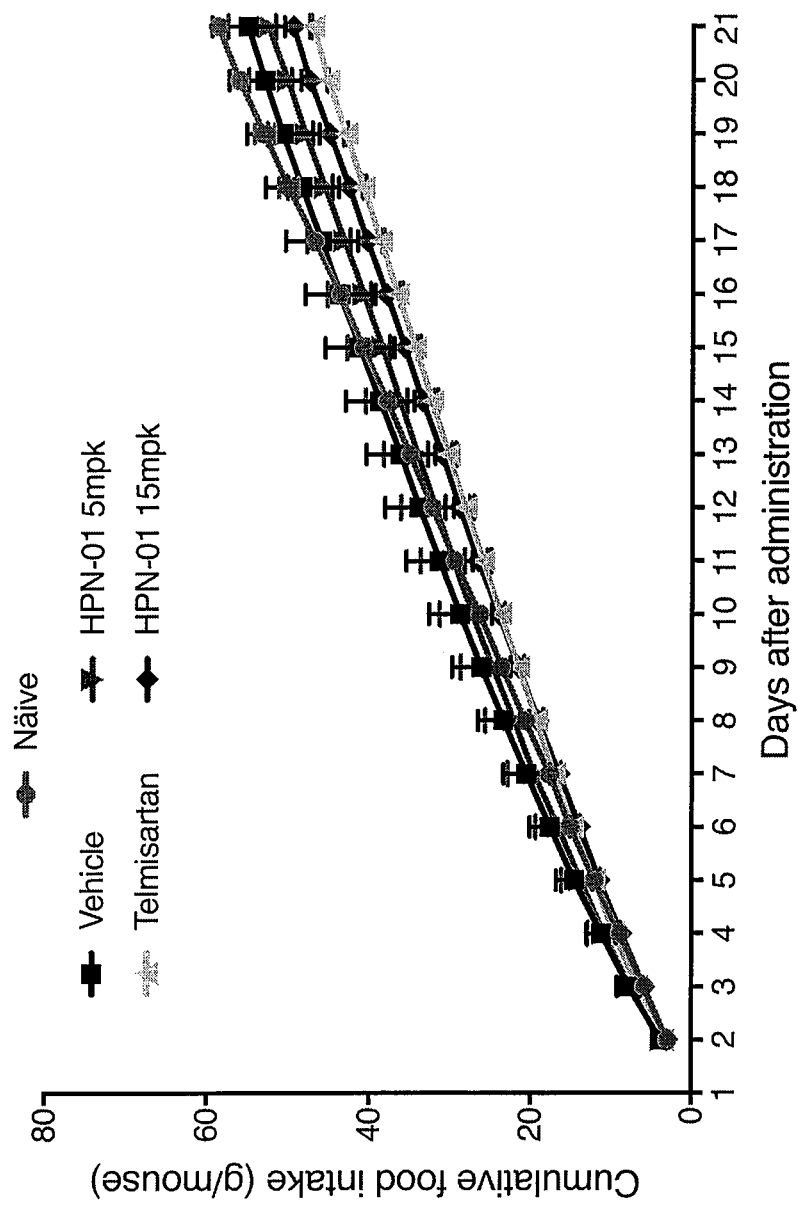

Example 27. Efficacy of HPN-01 on Streptozotocin (STZ) and High Fat Diet-Induced NASH Mice The effect of HPN-01 on various physical and biochemical parameters in mice induced to develop NASH was tested. The overall study design is shown in FIG. 27. Briefly, newborn C57/BL6J mice were divided into 5 groups, with 8 animals per group. One group (naïve) was fed normal chow diet throughout the study, and did not receive drug treatment of any kind. The remaining four groups were injected on days 2, 3 and 4, with Vehicle (Vehicle consists of 40% PEG400:10% Cremophor EL:50% water) containing 90 μg of streptozotocin (STZ), and fed a high fat diet (HFD) from week 4 through week 9 to establish NASH hallmarks in the liver. One of the groups (Vehicle group) that received STZ was not given any further drug treatment. The remaining three groups received either orally administered Telmisartan or orally administered HPN-01 starting at week 6 and continuing for 3 weeks. Telmisartan was orally administered once per day (QD) at a dosage of 10 mpk (mg/kg weight); this group served as a positive control. HPN-01 was administrated orally twice a day (BID) with either a lower (5 mpk) or a higher (15 mpk) dose. For each group, body weight and food intake were recorded daily. FIG. 28A shows body weight changes in untreated mice fed a normal chow diet (Naïve; gray circles), vehicle-treated mice fed a high fat diet (Vehicle; black squares), telmisartan-treated mice fed a high fat diet (Telmisartan; gray upper arrow triangles), low-dose HPN-01-treated mice fed a high fat diet (HPN-01 5mpk; gray lower arrow triangles), and high-dose HPN-01-treated mice fed a high fat diet (HPN-01 15mpk; black diamonds). FIG. 28B shows the daily, cumulative food intake recorded for each study group. The results show that treatment with HPN-01 had no effect on nSTZ+HFD NASH mice body weight or on daily food intake.

Figure 29:
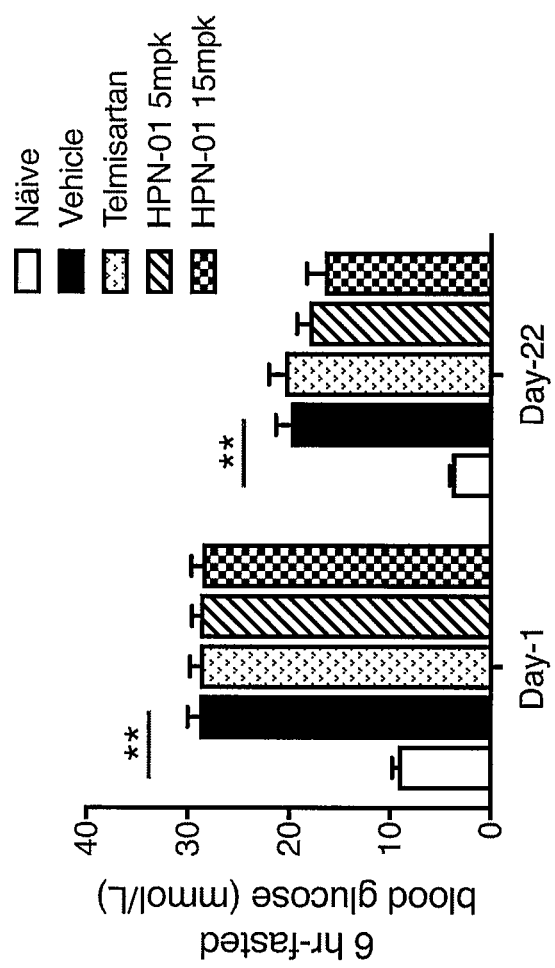
FIG. 29. Fasted blood glucose levels in untreated and HPN-01 treated nSTZ+HFD NASH mice. Blood glucose levels were measured at the start (Day-1) and the end (Day-22) of drug administration.

At the end of the study, animals were fasted overnight, and fasted blood glucose levels measured and compared with a fasted glucose level obtained on Day 1 of the study. FIG. 29 shows that HPN-01 treatment with HPN-01 had no effect on nSTZ+HFD NASH mice fasted blood glucose levels.

Mice were then euthanized, and whole blood drawn by cardiac puncture. Sera were prepared and stored at −80° C. for alanine aminotransferase (ALT), aspartate aminotransferase (AST), triglyceride (TG) and total cholesterol (TC) detection. Livers were isolated and liver weights were recorded. Liver tissues were stored at −80° C. for TG, TC detection, measurement of various inflammatory and fibrotic markers, and pathological studies.

Figure 30A:
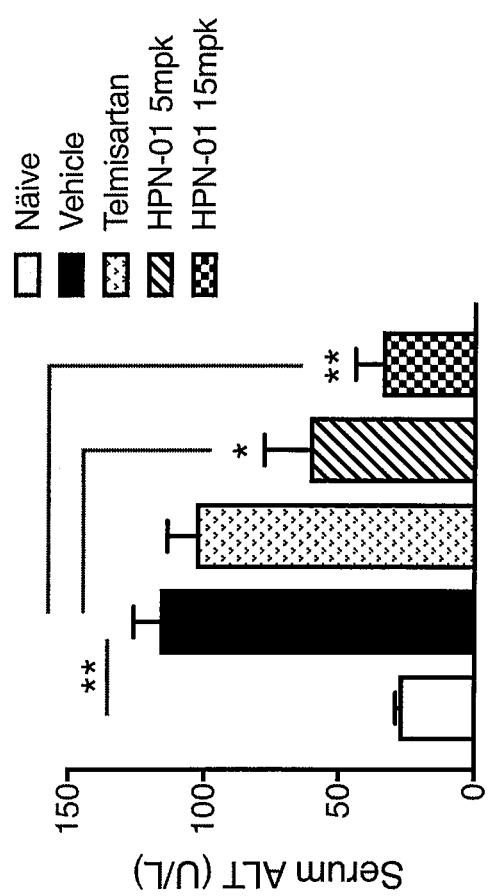
FIGS. 30A and 30B. Effects of HPN-01 treatment on Serum alanine aminotransferase (ALT) and serum aspartate aminotransferase (AST) levels in untreated and treated mice.
Figure 30B:
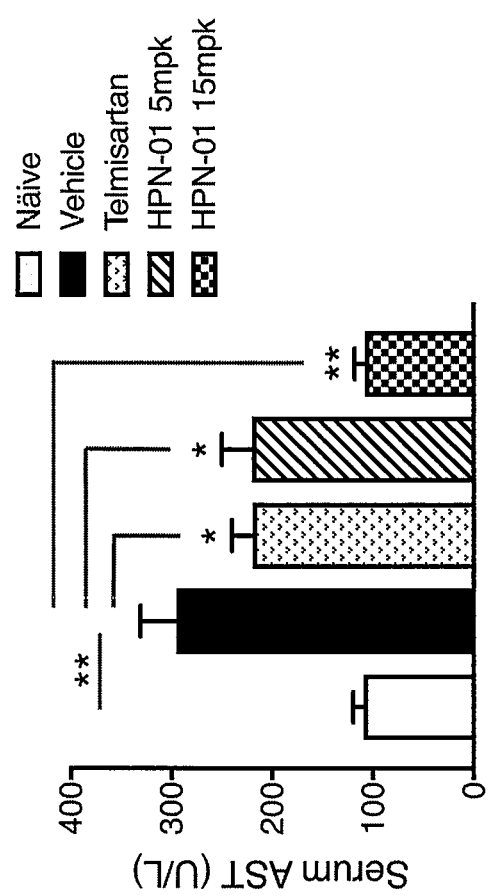

Serum alanine aminotransferase (ALT) and aspartate aminotransferase (AST) levels are shown in FIGS. 30A and 30B, respectively. The data show that HPN-01 significantly reversed the elevation of serum ALT (FIG. 30A) and AST (FIG. 30B) levels in nSTZ+HFD NASH mice, in a dose-dependent manner.

Figure 31A:
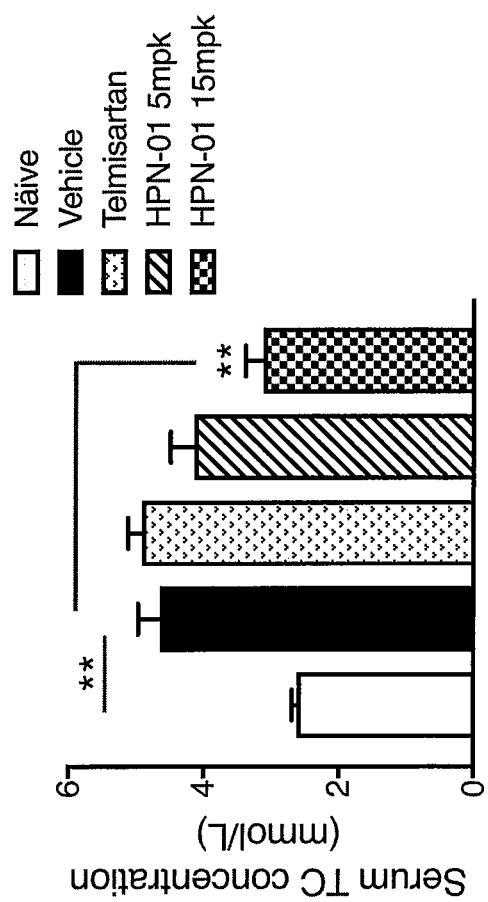
FIGS. 31A and 31B. Effects of HPN-01 treatment on serum total cholesterol (TC) and serum triglyceride (TG) levels in nSTZ+HFD NASH mice.
Figure 31B:
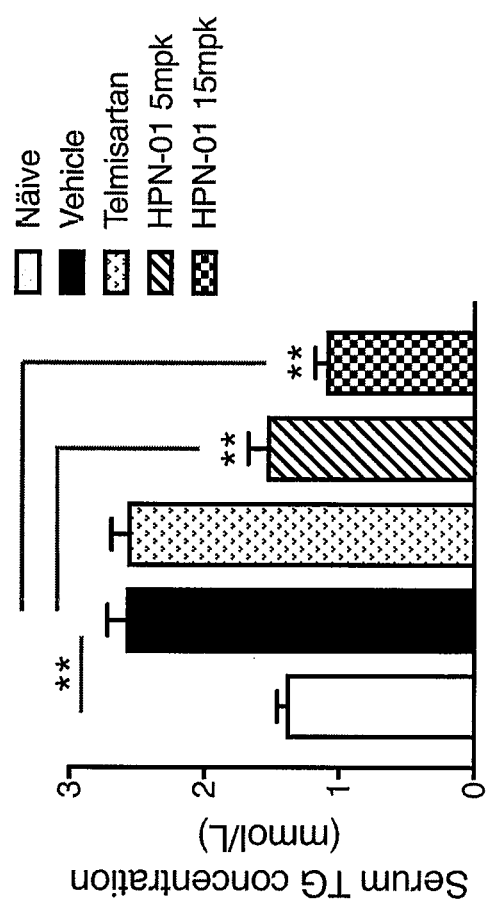

Serum total cholesterol (TC) and triglyceride (TG) levels in nSTZ+HFD NASH mice, are shown in FIGS. 31A and 31B, respectively. The data show that HPN-01 significantly abated the increase of serum TC (FIG. 31A) and TG (FIG. 31B) levels in NASH mice, in a dose-dependent manner.

Figure 32A:
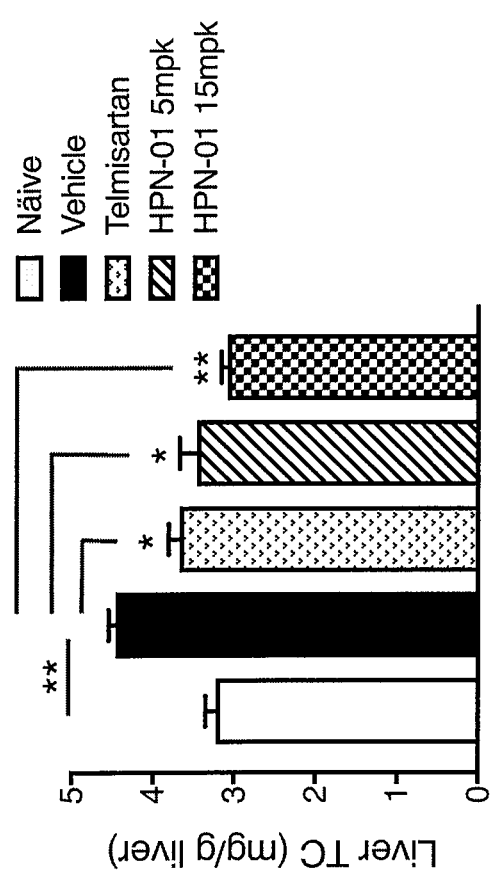
FIGS. 32A and 32B. Effects of HPN-01 treatment on nSTZ+HFD NASH mice liver total cholesterol (TC) and liver triglyceride (TG) levels.
Figure 32B:
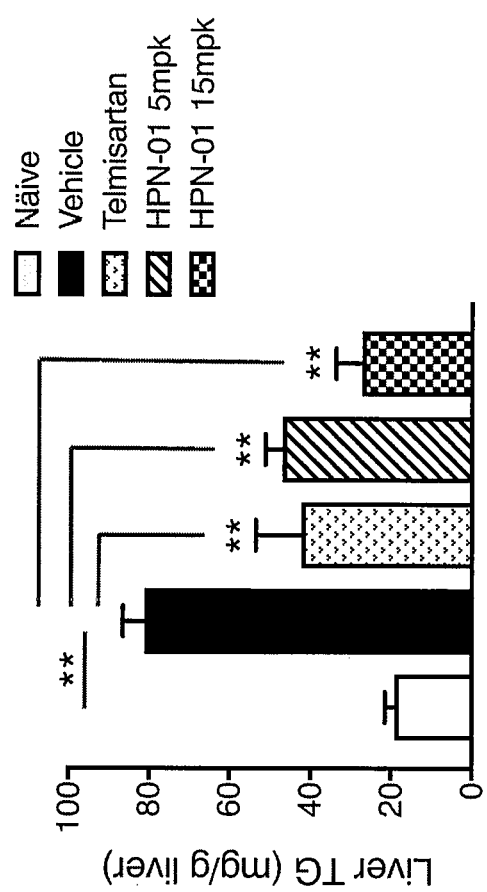

Total cholesterol (TC) and triglyceride (TG) levels from nSTZ+HFD NASH mouse livers is shown in FIGS. 32A and 32 B, respectively. The data show that HPN-01 administration significantly reversed the elevation of hepatic TC (FIG. 32A) and TG (FIG. 32B) levels, in a dose-dependent manner.

Figure 33A:
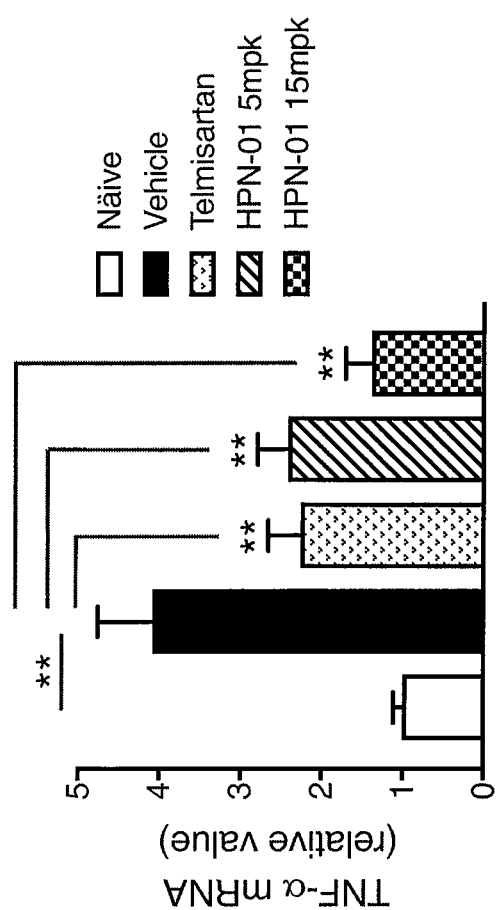
FIGS. 33A and 33B. Effect of HPN-01 treatment on inflammatory cytokine expression levels in mouse livers.
Figure 33B:
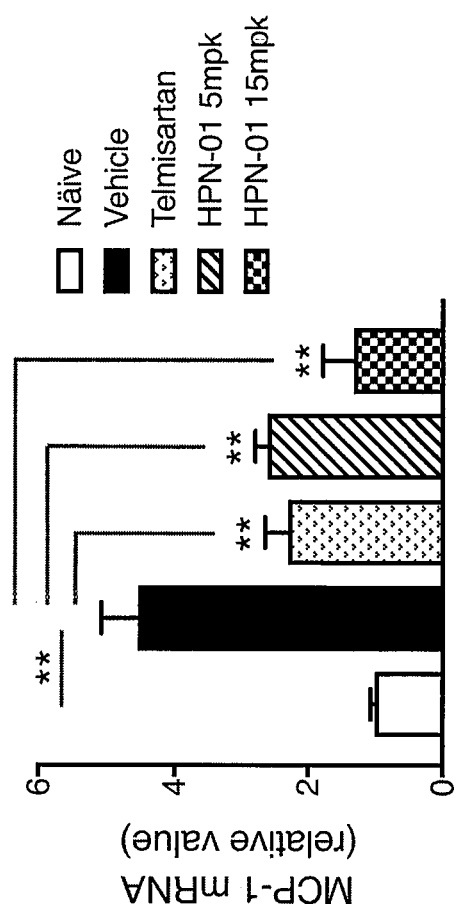
Figure 34A:
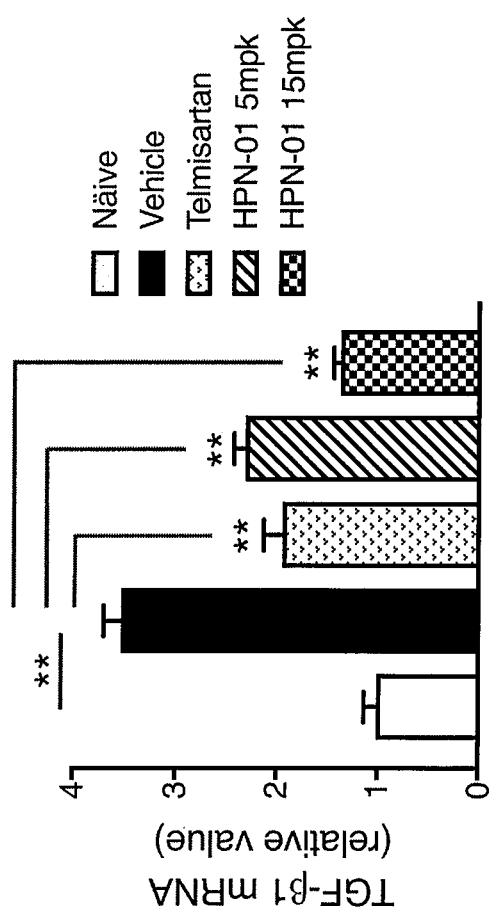
FIGS. 34A-C. Effect of HPN-01 treatment on the expression levels of various fibrotic markers.
Figure 34B:
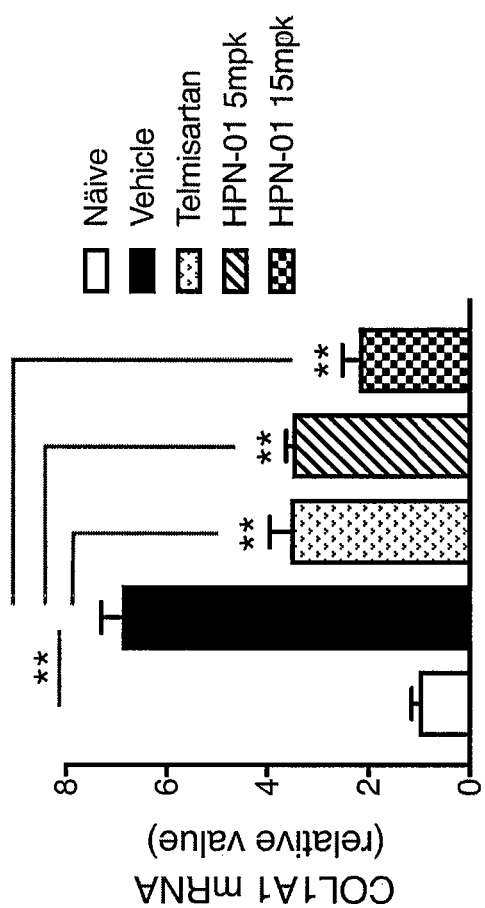
Figure 34C:
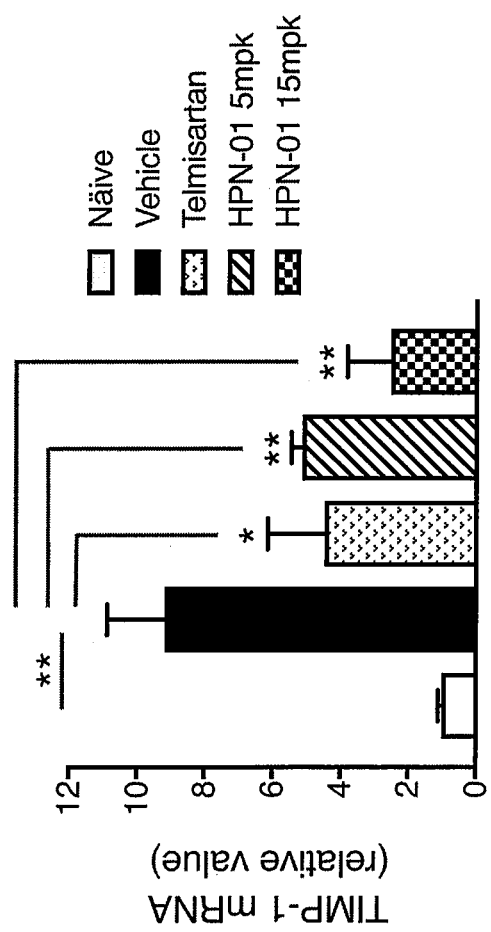

The level of TNF-α and MCP-1 mRNAs in the livers of mice treated as described above, is shown in FIGS. 33A and 33B, respectively. The data show that both TNF-α (FIG. 33A) and MCP-1 (FIG. 33B) were significantly suppressed by HPN-01 treatment, in a dose-dependent manner. Likewise, FIGS. 34A-34C show that HPN-01 treatment reduced the levels of transforming growth factor beta 1 (TGF-β1) (FIG. 34A), collagen type 1 alpha 1 (COL1A1) (FIG. 34B) and tissue inhibitor of metalloproteinase-1 (TIMP-1) (FIG. 34C), in a dose-dependent manner.

Figure 35A:
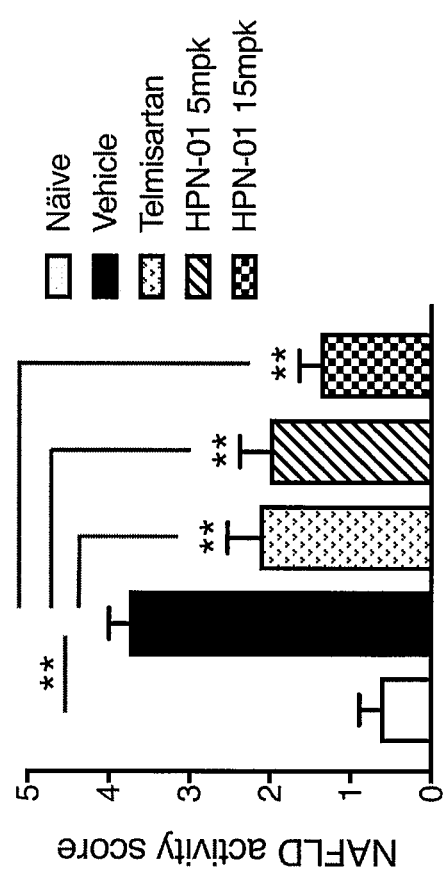
FIGS. 35A-D. Effect of HPN-01 treatment on NAFLD activity score. Liver tissues from various groups from the study outlined in FIG. 27 were observed under a microscope upon Hematoxylin and Eosin (H&E) stain and Oil-red-O staining. Evaluation of multiple NAFLD/NASH pathological hallmarks including NAFLD activity, hepatic steatosis (FIG. 35B), ballooning (FIG. 35C) and inflammation (FIG. 35D) was conducted.
Figure 35B:
Figure 35C:
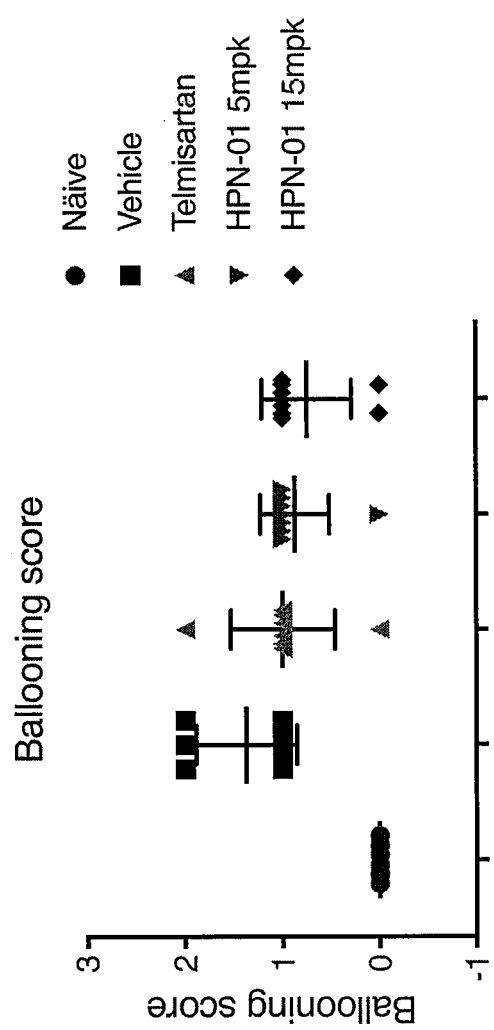
Figure 35D:
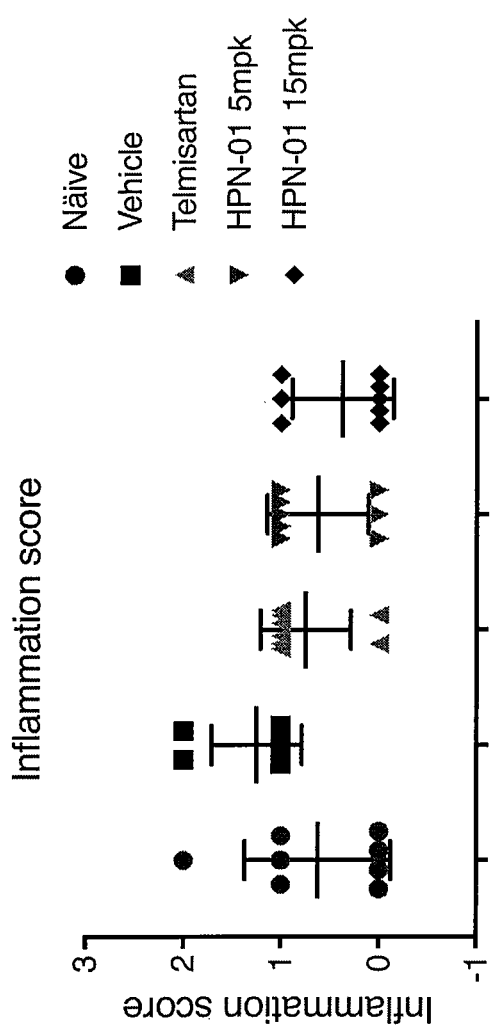
Figure 36:
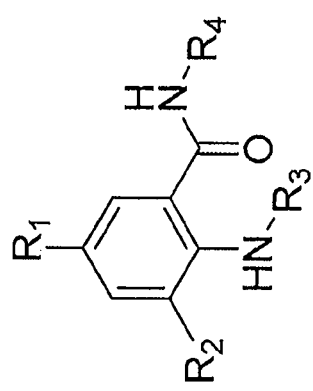
FIG. 36. Structure of HPN-01 variants.

Liver tissues from various groups from the study shown in FIG. 27 were observed under a microscope following Hematoxylin and Eosin (H&E) stain and Oil-red-O staining, and an NAFLD activity score determined. The result is shown in FIG. 35A. Additional NAFLD/NASH pathology scores were also determined, including a hepatic steatosis score (FIG. 35B), a ballooning score (FIG. 35C) and an inflammation score (FIG. 35D).

While this invention has been described in conjunction with specific embodiment and examples, it should be apparent to a person of ordinary skill in the art, having regard to that skill and this disclosure, that equivalents of the specifically disclosed materials and methods will also be applicable to this invention; and such equivalents are included within the following claims.

We claim:

1. A method of treating nonalcoholic steatohepatitis in a subject, comprising administering to the subject a pharmaceutical composition comprising a therapeutically effective amount of a compound selected from the group consisting of: methyl (E)-3-(6-amino-4'-(amino-(methylene)sulfinyl)-5-carbamoyl- [1,1'-biphenyl]-3-yl) acrylate (HPN-01114), (E)-2-amino-5-(3-((4-chlorophenyl)amino)-3- oxoprop-1-en-1-yl)-4'-sulfamoyl-[1,1-biphenyl]-3-carboxamide (HPN-01130), (E)-2-amino-5- (3-((4-fluorophenethyl)amino)-3-oxoprop-1-en-1-yl)-4'-sulfamoyl-[1,1'-biphenyl]-3-carboxamide (HPN-01132), 3-(6-amino-5-carbamoyl-4'-sulfamoyl-[1,1'-biphenyl]-3-yl)prop-2-yn-1-yl 2-methoxybenzoate (HPN-01217), and 4'-amino-4-bromo-N-cyclopropyl-4"-sulfamoyl-[1,1':3',1"-terphenyl]-5'-carboxamide (HPN-01606), or hydrate, solvate, or pharmaceutically acceptable salt thereof.

2. The method of claim 1, wherein the compound is administered in a dose of between about 0.1 mg/kg to about 100 mg/kg body weight of the subject.

3. The method of claim 1, wherein the pharmaceutical composition is administered at a frequency selected from the group consisting of once in a 24-hour period, once every 24 hours, once every 12 hours, once every 6 hours, once every 4 hours, once every 3 hours, once every 2 hours, once every hour, and continuously.

4. The method of claim 1, wherein the compound is administered in a dose of between about 0.1 mg/kg to about 100 mg/kg body weight of the subject/day.

5. The method of claim 1, wherein the pharmaceutical composition further comprises a carrier.

6. The method of claim 5, wherein the carrier is selected from the group consisting of a buffer, an antioxidant, low molecular weight polypeptide, a protein, a hydrophilic polymer, an amino acid, a carbohydrate, a chelating agent, a sugar alcohol, a salt-forming counterion, and a nonionic surfactant.

7. The method of claim 6, wherein the buffer is selected from the group consisting of phosphate buffer, citrate buffer, Hanks' balanced salt solution, and Ringer's solution.

8. The method of claim 6, wherein the protein is selected from the group consisting of serum albumin, gelatin, and immunoglobulin.

9. The method of claim 6, wherein the amino acid is selected from the group consisting of glycine, glutamine, asparagine, arginine, and lysine.

10. The method of claim 6, wherein the carbohydrate is selected from the group consisting of a monosaccharide, a disaccharide, and a dextrin.

11. The method of claim 6, wherein the sugar alcohol is mannitol or sorbitol.

12. The method of claim 6, wherein the nonionic surfactant is selected from the group consisting of a polysorbate, a polyethylene glycol, and a poloxamer.

13. The method of claim 1, wherein the pharmaceutical composition further comprises an additional agent selected from the group consisting of a flavoring agent, a coloring agent, a sweetening agent, and a thickening agent.

14. The method of claim 1, wherein the pharmaceutical composition is formulated for administration in a form selected from the group consisting of a tablet, a capsule, a powder, a troche, a lozenge, a suspension, a gel, a paste, a slurry, a liquid composition, a soft-gel capsule, and a syrup.

15. The method of claim 1, wherein the pharmaceutical composition is administered by a route selected from the group consisting of administration by injection, oral administration, transmucosal administration, transdermal administration, topical administration, nasal administration, ocular administration, and administration by suppository.

16. The method of claim 15, wherein the type of injection is selected from the group consisting of intravenous injection, intraperitoneal injection, intramuscular injection, and subcutaneous injection.

17. The method of claim 6, wherein the antioxidant is ascorbic acid, the hydrophilic polymer is polyvinylpyrrolidone, the chelating agent is EDTA, or the salt-forming counterion is sodium.

18. The method of claim 10, wherein the monosaccharide is glucose or mannose.

* * * * *